(12) United States Patent
Sumi

(10) Patent No.: US 9,084,559 B2
(45) Date of Patent: Jul. 21, 2015

(54) IMAGING METHOD, DISPLACEMENT MEASUREMENT METHOD AND APPARATUS

(76) Inventor: Chikayoshi Sumi, Tokorozawa (JP)

(*) Notice: Subject to any disclaimer, the term of this patent is extended or adjusted under 35 U.S.C. 154(b) by 467 days.

(21) Appl. No.: 13/424,660

(22) Filed: Mar. 20, 2012

(65) Prior Publication Data

US 2013/0046175 A1    Feb. 21, 2013

(30) Foreign Application Priority Data

Jun. 16, 2011 (JP) ................. 2011-134573

(51) Int. Cl.
*A61B 8/00* (2006.01)
*A61B 8/08* (2006.01)

(52) U.S. Cl.
CPC . *A61B 8/08* (2013.01); *A61B 8/483* (2013.01); *A61B 8/485* (2013.01)

(58) Field of Classification Search
USPC ................................. 600/437, 438
See application file for complete search history.

(56) References Cited

U.S. PATENT DOCUMENTS

| 7,690,838 | B2 | 4/2010 | Sumi |
| 7,775,980 | B2 | 8/2010 | Sumi |
| 7,868,824 | B2 | 1/2011 | Sumi |
| 7,946,180 | B2 | 5/2011 | Sumi |
| 2006/0173319 | A1 | 8/2006 | Sumi |
| 2011/0172538 | A1 | 7/2011 | Sumi |

FOREIGN PATENT DOCUMENTS

| JP | 2007-152074 A | 6/2007 |
| JP | 2011-078744 A | 4/2011 |

OTHER PUBLICATIONS

C. Sumi et al.: "Phantom Experiment on Estimation of Shear Modulus Distribution in Soft Tissue fromUltrasonic Measurement of Displacement Vector Field": IEICE Trans. Fundamentals, vol. E78-A, No. 12: Dec. 1995: pp. 1655-1664. (in English).
C. Sumi: "Fine Elasticity Imaging Utilizing the Iterative RF-echo Phase Matching Method": IEEE Transactions on Ultrasonics, Ferroelectrics, and Frequency Control: vol. 46, No. 1: Jan. 1999: pp. 158-166. (in English).

(Continued)

*Primary Examiner* — Peter Luong
(74) *Attorney, Agent, or Firm* — Holtz, Holtz, Goodman & Chick PC

(57) ABSTRACT

A displacement measurement method for achieving, at each position of interest, high accuracy measurement of a displacement, a velocity and a strain in an actually generated beam direction by measuring the beam direction angle from ultrasound echo data. The method includes the steps of: generating an ultrasound echo data frame through scanning an object in a lateral direction with an ultrasound steered beam having one steering angle; calculating both a beam direction and a frequency in the beam direction based on an azimuth angle $\phi = \tan^{-1}(fy/fx)$, a polar angle $\theta = \cos^{-1}[fz/(fx^2+fy^2+fz^2)^{1/2}]$, and a frequency $(fx^2+fy^2+fz^2)^{1/2}$ in the case where first spectral moments calculated from local ultrasound echo data at plural different temporal phases are expressed by a three-dimensional frequency vector (fx, fy, fz); and calculating a displacement component in the beam direction at each position of interest generated between plural different temporal phases.

40 Claims, 12 Drawing Sheets

(56) References Cited

OTHER PUBLICATIONS

C. Sumi: Displacement Vector Measurement Using Instaneous Ultrasound Signal Phase—Multidimensional Autocorrelation and Doppler Methods: IEEE Transactions on Ultrasonics, Ferroelectrics, and Frequency Control: vol. 55, No. 1: Jan. 2008: pp. 24-43. (in English).

C. Sumi: "3D Imaging of Shear Modulus Distribution in Living Soft Tissues": Sep. 1999: pp. 1201-1202.

C. Sumi et al.: "Phantom experiments of axial strain measurements using multidimensional autocorrelation method, multidimensional Doppler method and direct strain measurement method": Acoustical Science & Technology: vol. 30, No. 2: 2009: pp. 117-123. (in English).

C. Sumi et al.: "Effective Lateral Modulations With Applications to Shear Modulus Reconstruction Using Displacement Vector Measurement": IEEE Transactions on Ultrasonics, Ferroelectrics, and Frequency Control: vol. 55, No. 12: Dec. 2008: pp. 2607-2625. (in English).

C. Sumi et al.: "Comparison of Parabolic and Gaussian Lateral Cosine Modulations in Ultrasound Imaging, Displacement Vector Measurement, and Elasticity Measurement": Japanese Journal of Applied Physics: vol. 47, No. 5: 2008: pp. 4137-4144. (in English).

J.A. Jensen: "A New Method for Estimation of Velocity Vectors": IEEE Transactions on Ultrasonics, Ferroelectrics, and Frequency Control: vol. 45, No. 3: May 1998: pp. 837-851. (in English).

M.E. Anderson: "Multi-Dimensional Velocity Estimation with Ultrasound Using Spatial Quadrature": IEEE Transactions on Ultrasonics, Ferroelectrics, and Frequency Control: vol. 45, No. 3: May 1998: pp. 852-861. (in English).

C. Sumi et al.: "A Demonstration of Optimal Apodization Determination for Proper Lateral Modulation": Japanese Journal of Applied Physics: vol. 48 (7B), 07GJ06: Jul. 2010: pp. 07GJ06-1-07GJ06-10. (in English).

C. Sumi et al.: "Proper Analytic Point Spread Function for Lateral Modulation": Japanese Journal of Applied.Physics: vol. 49 (7B), 07HF07: Jul. 2010: pp. 07HF07-1-07HF07-2. (in English).

C. Sumi: "Increasing Accuracy of Tissue Shear Modulus Reconstruction using Ultrasonic Strain Tensor Measurement—Lateral Modulation and Regularization": Acoustical Imaging: vol. 29: 2008: pp. 59-68. (in English).

C. Sumi et al.: "Ultrasonic agar phantom experiment for comparison of the measurement accuracy of tissue elasticity obtained by displacement vector measurement using lateral modulation with multidimensional autocorrelation and Doppler methods and corresponding one-dimensional methods": Journal of Reports in Medical Imaging: vol. 4 (2011): pp. 39-46. (in English).

J.A. Jensen: "A New Estimator for Vector Velocity Estimation": IEEE Transactions on Ultrasonics, Ferroelectrics, and Frequency Control: vol. 48, No. 4: Jul. 2001: pp. 886-894. (in English).

M.E. Anderson: "A Heterodyning Demodulation Technique for Spatial Quadrature": 2000 IEEE Ultrasonics Symposium: pp. 1487-1490. (in English).

C. Sumi et al.: "Increase in measurement accuracy of tissue displacement vector using rotation of coordinate system": IEICE Technical Report US2010-82: pp. 25-32.

C. Sumi: "Usefulness of Ultrasonic Strain Measurement-Based Shear Modulus Reconstruction for Diagnosis and Thermal Treatment": IEEE Transactions on Ultrasonics, Ferroelectrics, and Frequency Control: vol. 52, No. 10: Oct. 2005: pp. 1670-1689. (in English).

C. Sumi et al.: "Reconstruction of thermal property distributions of tissue phantoms from temperature measurements—thermal conductivity, thermal capacity and thermal diffusivity": Physics in Medicine and Biology: vol. 52: No. 10 (2007): pp. 2845-2863. (in English).

Y. Yamakoshi et al.: "Ultrasonic Imaging of Internal Vibration of Soft Tissue under Forced Vibration": IEEE Transactions on Ultrasonics, Ferroelectrics, and Frequency Control: vol. 37, No. 2: Mar. 1990: pp. 45-53. (in English).

C. Sumi.: "Relative shear modulus reconstruction for visualization with no geometrical artifact": Acoustical Science & Technology: vol. 31, No. 5: 2010: pp. 347-359. (in English).

C. Sumi: "Utilization of an ultrasound beam steering angle for measurements of tissue displacement vector and lateral displacement": Reports in Medical Imaging: vol. 3 (2010): pp. 61-81. (in English).

A. Manduca et al.: "Spatio-temporal directional filtering for improved inversion of MR elastography images": Medical Image Analysis vol. 7, No. 4 (2003): pp. 465-473.

Jeremy Bercoff: "Supersonic Shear Imaging: A New Technique for Soft Tissue Elasticity Mapping": IEEE Transactions on Ultrasonics, Ferroelectrics, and Frequency Control: vol. 51, No. 4: Apr. 2004: pp. 396-409. (in English).

Y.C. Fung: "Foundations of Solid Mechanics—Chapter 2—Tensor Analysis:": Prentice Hall Inc.: 1965: pp. 31-57. (in English).

ULTRASOUND BEAM

SERIES OF ELECTRIC VOLTAGE SIGNAL FOR ONE BEAM ↓ ↑ ELECTRIC PULSE

ULTRASOUND OSCILLATOR (a)

1D ARRAYED ULTRASOUND OSCILLATORS (b)

2D ARRAYED ULTRASOUND OSCILLATORS (c)

(A) ULTRASOUND BEAM (B) SYMMETRIC / SYMMETRIC / LATERAL DIRECTION / DEPTH DIRECTION / FREQUENCY DOMAIN (A) ULTRASOUND BEAM (B) LATERAL DIRECTION / DEPTH DIRECTION / FREQUENCY DOMAIN (a)

(b)

(c)

(a) SPACE DOMAIN    (b) FREQUENCY DOMAIN (a) SPACE DOMAIN    (b) FREQUENCY DOMAIN

FREQUENCY DOMAIN (a)

(b)

(c)

(d)

IMAGING METHOD, DISPLACEMENT MEASUREMENT METHOD AND APPARATUS

CROSS-REFERENCE TO RELATED APPLICATION

The present application claims priority from Japanese Patent Application No. 2011-134573 filed on Jun. 16, 2011, the contents of which are incorporated herein by reference in their entirety.

BACKGROUND OF THE INVENTION

1. Field of the Invention

The present invention is related to the measurement methods and measurement apparatuses for non-invasively and quantitatively measuring internal mechanical properties and physical quantities such as a displacement, a strain, a velocity, an acceleration etc. of target objects, substances, materials, living things etc. For instance, the present invention is related to new measurement methods and measurement apparatuses for generating an internal displacement vector distribution, an internal strain tensor distribution, an internal strain rate tensor distribution, an internal acceleration vector distribution etc. by applying a mechanical source such as a compression, a vibration, a radiated force etc. to a target, and generating echo data and imaging data by properly performing beamforming for measuring the physical quantities. Alternatively, the present invention also permits the measurement of spontaneous tissue motion such as of a heart, a lung wall etc., and tissue motion generated by body motion, respiratory, heartbeat, blood pulsation etc. The present invention also permits the measurement of a blood flow vector in a heart and a blood vessel. Such measurements can also be performed simultaneously. The measurement results also permit the measurements of mechanical properties and thermal properties etc. The applications are various.

The typical applications of the present invention in a medical field is to ultrasound (US) diagnosis apparatuses, nuclear magnetic resonance imaging (NMRI) apparatuses, optical diagnosis apparatuses etc. for observing internal tissues (diagnosis of cancerous diseases, infarctions, scleroses, thrombi, hemodynamics, blood oxygen saturations etc.) and radiation therapy apparatuses including a high intensity focus ultrasound (HIFU) apparatus. That is, the present invention permits obtaining a safety and a confidence for such various treatments, and an improvement in treatment effectiveness by tracking tissue displacements in treatment parts etc. as well as for such diagnoses by observing target tissue motions/deformations, hemodynamics and various dynamics. Tissue degenerations can also be monitored for the evaluation of the treatment effectiveness. The applications of the present invention is not limited to these mentioned above. As the non-destructive measurement methods, such evaluations, examinations and diagnoses can also be performed on various objects.

2. Description of a Related Art

For instance, in a medical field, treatment of diseases is performed using a radiation therapy, a high intensity ultrasound radiation, a laser radiation, a radio-frequency (rf) electromagnetic radiation, a microwave electromagnetic radiation, a cryotherapy, a cooling therapy etc. For such treatments, the above-mentioned tissue tracking and monitoring of the treatment effectiveness is proposed to be performed. Alternatively, non-invasive observing of treatment effectiveness is also performed on the use of medicine such as an anti-cancer drug etc. For instance, because the temperature of a disease part changes when such a radiation therapy etc. is performed, the treatment effectiveness can be monitored by non-invasively measuring the generated degeneration (including a temperature change). Otherwise, the evaluation of blood flow in a disease part also permits differential diagnosis on a disease progress etc. Measurement of a displacement, a strain, and changes in displacements and strains etc. generated in a region of interest (ROI) in living tissues such as a disease part and a treatment part by a force applied to the ROI is proposed to be used for diagnosis and observing a treatment effectiveness etc. on the basis of the evaluation of a difference in tissue characteristics (elastic constants etc.) between the part and the surrounding tissues. Such observing is permitted by using the US apparatuses, MRI apparatuses, various optical diagnosis apparatuses including radiation diagnosis apparatuses such as an X-ray diagnosis apparatus, various temperature measurement apparatuses etc., in which features of a wave propagation such as of mechanical waves, electromagnetic waves, thermal waves etc. are used.

It is known that the temperature of the ROI in the target has correlations with elastic constants, visco-elastic constants, delay times and relaxation times determined by elastic constants and visco-elastic constants, density, viscosities etc. Thus, the non-destructive measurement of elastic constants such as shear modulus, Poisson's ratio etc., visco-elastic constants such as visco-shear modulus, visco Poisson's ratio etc., delay times and relaxation times determined by the respective elastic constants and corresponding visco-elastic constants, density, viscosities etc. (e.g., patent documents 2 and 6; non-patent document 20) permits the measurement of a temperature or a temperature distribution in the ROI (e.g., patent document 2). The temperature distribution can also be measured directly by measuring a strain distribution generated by the temperature change. These temperature measurement methods permit the monitoring of various thermal treatments; and an additional calculation of thermal property distributions permit planning of the thermal treatment (e.g., patent document 5).

Alternatively, for instance, US apparatuses used in a medical field transmit ultrasounds from a US transducer to internal target tissues; and receive US echo signals reflected from the internal tissues using the US transducer; and measure a distribution of the tissues etc. on the basis of the conversion of the received echo signals into an observational image etc. The US transducer to be used in the present invention can have various aperture geometries and can employ various type US vibrators. By measuring displacements generated by an arbitrary mechanical source or by calculating distributions of strain tensor or elastic constants from the measured displacement data, differences between diseases such as liver cancers etc. and normal tissues can be observed non-invasively. When using other apparatuses such as NMRI apparatuses, various optical diagnosis apparatuses, various temperature measurement apparatuses, the similar measurement, calculation and imaging can be performed.

Alternatively, measurement and imaging of shear modulus is also performed on the basis of the measurement of shear wave propagation speed, in which the shear wave is generated by using mechanical sources such as a low frequency vibrator and a radiated force (e.g., non-patent document 19). For the measurement of the shear wave propagation speed, the calculation method for measuring a displacement is used (measurement of an instantaneous phase change). An instantaneous phase change between frames can be detected to measure the position where a displacement (strain) wave reaches. In such a case, high measurement accuracy may not be required for the measurement of the instantaneous phase change. This is also for the use of incoherent signals obtained from the coherent echo signals. In contrast, a high measurement accuracy of a tissue displacement is required to achieve a specific and high accuracy measurement of the shear wave. It is valuable to measure the propagation direction of the shear wave with a high accuracy, and if mechanical sources or thermal sources generated using radiated forces can be controlled, the propagation direction of the shear wave can be controlled and the target tissue can be deformed in a proper direction; and anisotropic elastic constant (shear modulus) distributions can be determined. However, a proper method has not been developed yet. However, another method has been developed for the measurement of the shear wave propagation speed particularly useful when using a low frequency vibration, i.e., although generally the measurement becomes difficult when a stationary wave is generated by a reflection phenomenon, it is possible to distinguish the transmission wave and the reflection wave. For a one-dimensional wave propagating in a lateral direction, the method is disclosed in non-patent document 22 etc.; and for a multi-dimensional wave, it is also possible in a similar fashion. However, because the wavelength of the shear wave is long, the spatial resolution achievable for the shear wave propagation speed measurement is low. This is an inherent limitation.

Thus, it is proposed that ultrasounds are transmitted plural times with a temporal interval, and the internal displacement is measured using the change in echo signals obtained at the successive US transmissions. Moreover, it is proposed that internal mechanical quantities such as strains etc. are calculated from the displacements measured at respective positions, and furthermore the tissue characteristics are diagnosed non-invasively. For a three-dimensional (3D), two-dimensional (2D) or one-dimensional (1D) ROI set in the target, the distribution of three, two or one component of a 3D displacement vector generated is measured. The measured displacement data and correspondingly calculated strain data are used to calculate elastic constant distributions etc. in the ROI.

The US transducer has functions of sensors for measuring the displacements and strains generated. Instead of the transducer, other type sensors can also be used such as detectors of a magnetic field, lights, temperature, laser and among others (a contact or non-contact type). For the mechanical source, the US transducer body is used as a compressor or is used as a vibrator by vibrating the body. Other mechanical sources from the US transducer can also be used (i.e., a compressor or a vibrator). Cardiac motion or blood pulsation can also be used as a mechanical source. Otherwise, an internal mechanical source can also be generated by radiating a force. When using a US transducer for radiating the force to generate deformations in the ROI as well as for the sensors for measuring the displacements or strains, other mechanical sources may not be used. For tissue characterization, changes in elastic constants and a temperature due to the thermal treatments and thermal properties as well as the elastic constants can also be used.

However, classical displacement measurement methods yield an only axial displacement measurement by performing 1D signal processing of the US echo signals in the axial (beam) direction (i.e., an axial direction is set in the direction of a beam direction) under the assumption that the target displacement directs in the axial direction. Hereafter, US echo signals include raw signals, quadrature- or envelope-detected signals, analytic signals etc. Because a practically generated displacement vector has displacement components with directions orthogonal to the axial (beam) direction, when using such classical methods, the measured axial displacement has a low accuracy (non-patent document 1). Furthermore, it is also impossible to measure the displacement components with directions orthogonal to the axial direction. For instance, it is difficult to accurately measure a blood flow (vector) in a heart and a blood vessel running parallel to the body surface and a tissue motion/deformation for tissues of which deformations cannot be controlled externally or the deformations are generated by cardiac motion or blood pulsation such as deeply situated tissues (e.g., liver).

In contrast, the present inventor proposes measurement methods of the displacement vector, i.e., methods using a multidimensional (i.e., 3D or 2D) cross-correlation or a phase gradient of a multidimensional cross-spectrum of echo signals (non-patent documents 1, 2 etc., i.e., one of high accuracy block matching methods together with the cross-correlation method). For the displacement vector measurement, the present inventor also proposes the multidimensional autocorrelation method and multidimensional Doppler method using multidimensional analytic signals etc. (patent documents 2, 4; non-patent document 3 etc.). From the viewpoints of a measurement accuracy and a calculation time required for the measurement purposes, these methods can be properly used, respectively. Otherwise, proper combinations of the methods can also be used.

In addition to the multidimensional measurement methods, the multidimensional phase matching method that the present inventor previously developed is effective (non-patent documents 1 to 5). The multidimensional phase matching prevents the measurement from phase aliasing due to a large displacement in the beam direction, and increases the measurement accuracy in all displacement vector components by increasing a correlation or a coherency between the pre- and post-deformed echo signals obtained from target tissues by performing a coarse matching of the echo signals in a multidimensional space (i.e., including lateral and/or elevational direction) using the coarse displacement estimates obtained using a multidimensional method such as the multidimensional cross-correlation method or multidimensional cross-spectrum phase gradient method before performing fine measurement of the target displacement vector with respect to the same echo signals using the multidimensional cross-spectrum phase gradient method, multidimensional autocorrelation method or multidimensional autocorrelation method (non-patent documents 1 to 3). Otherwise, although the measurement accuracy decreases, only the axial displacement is measured using low dimensional signal processing such as 1D signal processing instead of the multidimensional methods after the coarse measurement (non-patent documents 4, 5 etc.). For the coarse measurement, 1D signal processing etc. can also be performed in the respective directions.

When using the phase gradient of cross-spectrum, particularly for the coarse measurement, echo signals thinned out can be processed, i.e., with a coarse sampling interval (non-patent document 3). Although the phase matching can be performed in a frequency domain using phase rotation with complex exponential multiplication (non-patent documents 1 to 5), because the method requires a long calculation time, echo data in a searching region or a target local region can also be spatially shifted in a space (non-patent documents 1 to 5). When calculating the coarse displacement components from the phase gradient of cross-spectrum, because the original calculation results are analogue, the results are approximated by multiplications of integers and sampling intervals to permit the spatial shifting of echo signals. When using the cross-correlation method, calculation results of displacements are originally the multiplications of integers and sampling intervals. Because the cross-spectrum phase gradient method requires fewer calculations to achieve the measurement than the cross-correlation method, the cross-spectrum phase gradient method is more proper for real-time measurement.

For instance, by using these measurement methods, a displacement vector and an axial displacement can also be measured when uncontrollable mechanical sources exist (for living tissues, for instance, hear motion, respiratory, blood vessel pulsation, body motion etc.; lung, air, blood vessel, blood etc. are included in the ROI) as well as when using a compressor or a vibrator (US transducer may be used), a radiated force (US transducer may generate the force), etc. Thus, the multidimensional phase matching prevents the measurement from acquiring improper echo data. Similarly to the classical 1D measurement methods, these multidimensional displacement vector measurement methods also achieve real-time display of the measurement results through high speed calculation.

However, if displacements with the directions orthogonal to the axial (beam) direction remain after the phase matching, the measurement accuracy of the displacement vector and axial displacement decreases. That is, the measurement accuracy depends on the degree of the fineness of phase matching. Particularly when performing displacement vector measurement using conventional diagnosis apparatuses, because there are no carrier frequencies in the lateral and elevational directions; and lateral and elevational bandwidths are smaller than axial bandwidth, correspondingly measurement accuracies and spatial resolutions of the lateral and elevational displacement components decrease. Thus, being dependent on a measurement accuracy of lateral and elevational displacements, the measurement accuracy of the multidimensional displacement vector and strain tensor becomes low.

For such measurements, the present inventor has already realized a high accuracy measurement using generation method of echo data with lateral and elevational carrier frequencies together with above-mentioned displacement vector measurement methods. The accuracy of not only lateral and elevational displacement components but also an axial displacement component increased. It is a lateral modulation (LM) (for instance, non-patent documents 3, 6, 7 etc.). Jensen et al. determined an apodization function using the Fraunhofer approximation to generate a desired point spread function (PSF) (non-patent documents 8 and 9); the present inventor determined apodization functions on the basis of an optimization theory (patent document 3; non-patent documents 10, 11 etc.). The present inventor also determines the apodization function using the knowledge about the ultrasound propagation properties (for instance, non-patent documents 6, 7, 12 etc.). The present inventor also confirmed that power functions are proper functions for the apodization. The above-mentioned LM which the present inventor developed can also be used for echo imaging, in which almost the same high frequency can be obtained for the lateral direction as that for the axial direction. Thus, it is expected that LM beamforming becomes one of operation modes of general US diagnosis apparatuses.

For the transmission and reception beamforming, monostatic or multistatic synthesizing apertures can be performed for respective sets of received echo data. Simultaneously plural beams spatially crossed can be transmitted and received; simultaneously plural plane waves spatially crossed can be transmitted in order to superpose echo data received from a wide region (a high speed beamforming); plural crossed beams generated using plural physical apertures can be superposed; plural crossed beams obtained at different times can be superposed. Thus, the present inventor have developed various LM methods (patent documents 6 and 7; non-patent documents 3, 6, 7 etc.). Although LM can also be performed without consideration about the apodization (i.e., beam shape), performing above-mentioned optimized apodization permits a wideband echo data generation; US LM imaging can be achieved with a high spatial resolution and furthermore the displacement vector measurement can also be achieved with a considerably high accuracy.

When performing the LM regardless performing such apodization or not, a 3D echo data frame used for 3D displacement vector measurement can be obtained by superposing plural beams, ones steered in four or three directions (i.e., crossed beams); a 2D echo data frame used for 2D displacement vector measurement can be obtained by superposing two-directional steered beams (i.e., crossed beams) (non-patent document 3). Also in the present invention, the respective 3D or 2D echo data frames successively generated are dealt with as temporal series of an echo data frame that exhibits target tissue distribution at a temporal phase approximately. The inverse of the time between the frames is called as a frame rate. In order to deal with such respective 3D or 2D echo data frames at different temporal phases, because the tissue displacement exists between the echo data frames, it is desirable to generate the echo data frames from plural or single echo data received as in a short time as possible. Hereafter, in the present invention, "a temporal phase" is used in this sense.

For the tissue displacement vector measurement, the multidimensional cross-spectrum phase gradient method (non-patent documents 1 and 2), the multidimensional autocorrelation method (patent documents 2 and 4; non-patent document 3), the multidimensional Doppler method (patent documents 2 and 4; non-patent document 3) and the multidimensional cross-correlation method (non-patent documents 1 and 2) etc. can be used. All these measurement methods permit measurement of all displacement vector component distributions simultaneously for a displacement vector distribution generated between echo data frames at plural temporal phases. Because these measurement methods perform all processing such as moving-average processing etc. under the assumption that displacement components in plural directions exist, a considerably high accuracy measurement is achieved (non-patent document 13). On the same LM echo data frame obtained, the demodulation (patent document 1) can be implemented to yield echo data frames with carrier frequencies in the respective directions. In such a case, one-directional displacement measurement methods can be used to yield displacement vector measurement. In order to perform analogue demodulation (non-patent documents 14 and 15), plural echo data frames must be generated by transmission and reception of ultrasounds. However, when using echo data correspondingly obtained for beams physically transmitted at different times, the displacements generated between the transmissions lead to measurement errors. Also rapid motion rather than beam scanning decreases the measurement accuracy. In contrast, the demodulation which the present inventor developed (patent document 1) yields accurate measurements, because the demodulation is achieved through generation of only one echo data frame at a temporal phase and digital signal processing. However, a common problem exists for the analogue and digital methods. That is, because there exits displacements in the directions orthogonal to the direction with a carrier frequency, even if multidimensional moving-average is performed to mitigate the decrease in a measurement accuracy, an achievable accuracy is lower than that achieved using the multidimensional displacement vector measurement methods (non-patent document 13).

In view of a beamforming, these LMs require more beams than conventional beamforming to generate one echo data frame (above-mentioned 3D or 2D echo data). In addition, signal processing for acquiring echo data and generating echo data becomes more (i.e., apodization, switching, delay processing, phase matching, summation processing etc.). These lead to more time consumption for beamforming and a low frame rate. When LM is performed by synthetic aperture (SA) processing, according to a feature of SA, dynamic focusing can be performed at transmission as well as at reception. However, when the transmission powers from respective US vibrators (elements) are small, the signal-to-noise ratio of echo signal to be obtained becomes small. Moreover, a larger physical aperture is required than that required for conventional beamforming. Then, when obstacles such as bones etc. exist in the superficial tissues, deeply situated tissues cannot be dealt with. Moreover, a field of vision becomes small in the lateral and elevational directions as well.

Alternatively, for a high accuracy measurement, plural beams with different directions are realized similarly to the above-mentioned LMs, and however, a displacement vector can also be synthesized using axial displacement measurements obtained with a high accuracy from the echo data with the respective directional beams (i.e., non-superposed echo data). In the present invention, the measurement method is referred to as the multidirectional beamforming method (non-patent document 3). For the respective axial displacement measurement, not the one-directional displacement measurement methods but the above-mentioned multidimensional displacement vector measurement methods should be used similarly to in the LM cases (non-patent document 3). That is, the existence of displacements with the directions orthogonal to the beam direction should be considered. However, similarly to in the LM cases, the frame rate decreases. When using echo data correspondingly obtained for beams physically transmitted at different times, the displacements generated between the transmissions also lead to a measurement error. Also rapid motion rather than beam scanning decreases the measurement accuracy.

Then, the present inventor developed a new beamforming method that allows decreasing the measurement errors caused by the tissue displacements generated during the generation of an echo data frame by decreasing the time required for performing a beamforming. Consequently, real-time and high accuracy measurements of a displacement vector and a one-directional displacement were realized (patent document 1 and non-patent document 16 etc.).

A displacement measurement method exposed in the patent document 1 comprises the steps of:

(a) transmitting ultrasounds to an object using at least one ultrasound vibrator and yielding ultrasound echo data frames with respect to the object in an arbitrary direction using an ultrasound beam steered electrically and/or mechanically with a single steering angle over one of a three-dimensional orthogonal coordinate system having three axes substantially in a depth direction, a lateral direction orthogonal to the depth direction, and an elevational direction orthogonal to the depth direction and the lateral direction, and a two-dimensional orthogonal coordinate system having two axes substantially in a depth direction and a lateral direction orthogonal to the depth direction; and (b) calculating a displacement vector distribution by implementing a predetermined block matching on the ultrasound echo data frames yielded at more than two temporal phases.

For the transmission and reception beamforming, the classical monostatic or multistatic synthetic aperture (SA) method can be used; the scanning with a physically generated, steered beam can also be performed; the reception beamforming can also be performed on echo data obtained with respect to one or plural laterally wide wave transmissions such as non-steered (frontal with respect to an physical effective aperture) or steered plane wave transmissions on a Cartesian coordinate system at the same time or at the same temporal phase (i.e., high speed beamforming: on an arbitrary coordinate system, the transmission of one or plural laterally wide waves are performed at the same time or at the same temporal phase); and among others. Mechanical scanning solo or together with electrical scanning can be performed. That is, a 3D or 2D US echo data frame can be generated using an ultrasound beam electrically and/or mechanically steered with a single steering angle over the object.

A displacement measurement apparatus exposed in the patent document 1 comprises:

a transducer comprising at least one ultrasound vibrator configured to transmit ultrasounds to an object in accordance with at least one drive signal, and to detect ultrasound echo signals generated in the object to output echo signals;

a driving and processing unit configured to supply the at least one drive signal to the vibrator, and processing the echo signals outputted from the vibrator;

a control unit configured to control respective units to yield ultrasound echo data frames with respect to the object in an arbitrary direction using an ultrasound beam steered electrically and/or mechanically with a single steering angle over one of a three-dimensional orthogonal coordinate system having three axes substantially in a depth direction, a lateral direction orthogonal to the depth direction, and an elevational direction orthogonal to the depth direction and the lateral direction, and a two-dimensional orthogonal coordinate system having two axes substantially in a depth direction and a lateral direction orthogonal to the depth direction; and a data processing unit configured to calculate a displacement vector distribution by implementing a predetermined block matching on the ultrasound echo data frames yielded at more than two temporal phases.

For the transmission and reception beamforming, the classical monostatic or multistatic synthetic aperture (SA) method can be used; the scanning with a physically generated, steered beam can also be performed; the reception beamforming can also be performed on echo data obtained with respect to one or plural laterally wide wave transmissions such as non-steered (frontal) or steered plane wave transmissions on a Cartesian coordinate system at the same time or at the same temporal phase (i.e., high speed beamforming: on an arbitrary coordinate system, the transmission of one or plural laterally wide waves are performed at the same time or at the same temporal phase); and among others. Mechanical scanning solo or together with electrical scanning can be performed. That is, a 3D or 2D US echo data frame can be generated using an ultrasound beam electrically and/or mechanically steered with a single steering angle over the object.

The beamforming method exposed in the patent document 1 performs apodization, switching, delay, phase matching, summation processing, and occasionally mechanical scanning, and on the basis of such processing, the beamforming method performs beam steering by transmitting a steered beam with a steering angle in a 3D or 2D ROI, or a 1D ROI in a lateral direction primarily or in a depth direction in the object and receiving a steered beam with the same steered beam with respect to echo signals generated in the object. If necessary, the beamforming method performs scanning with the steered beam with respect to the object to obtain a 3D or 2D echo data frame. On the basis of the phase difference between the steered beams or the echo data frames with the same steering angle obtained at different temporal phases using the beamforming method, the combinational use of the above-mentioned displacement vector measurement method or the above-mentioned one-directional displacement measurement method permits measurement of a local displacement vector or a local one-directional displacement in a lateral direction primarily or in a depth direction, or a distribution of the local displacements. For a displacement vector measurement, the present inventor also developed the spectra frequency division method that divides spectra in a frequency domain and yields plural Doppler equations for the multidimensional autocorrelation method or multidimensional Doppler method from the respective divided spectra (i.e., multidimensional analytic signals obtained from the divided spectra).

For the transmission and reception beamforming, the classical monostatic or multistatic synthetic aperture (SA) method can be used; the scanning with a physically generated, steered beam can also be performed; the reception beamforming can also be performed on echo data obtained with respect to one or plural laterally wide wave transmissions such as non-steered (frontal) or steered plane wave transmissions on a Cartesian coordinate system at the same time or at the same temporal phase (i.e., high speed beamforming: on an arbitrary coordinate system, the transmission of one or plural laterally wide waves are performed at the same time or at the same temporal phase); and among others. Mechanical scanning solo or together with electrical scanning can be performed. That is, a 3D or 2D US echo data frame can be generated using an ultrasound beam electrically and/or mechanically steered with a single steering angle over the object. In the present invention, the beamforming is referred to as a steering angle (ASTA) beamforming method.

As disclosed in the non-patent document 6, the ASTA beamforming method does not require the generation of plural beams, and the possibly decreases the measurement errors or affections caused by the tissue displacements during the generation of one echo data frame by performing beam scanning. Because the ASTA beamforming does not always yield the best measurement and imaging, other beamforming such as the LM beamforming (patent document 1: virtual source or virtual receiver can also be used), non-steered (frontal) beamforming with respect to the physical aperture and among others that are permitted by the same hardware components that permits the ASTA beamforming can also be selected together with displacement measurement methods. The US diagnosis apparatus disclosed in the patent document 1 is equipped with the function for selecting their beamforming methods and displacement measurement methods. Moreover, a transmission can also be performed with respect to an arbitrary direction over a laterally wide ROI at the same time or at the same temporal phase. Synthetic aperture can also be performed. When using a 1D or 2D arrayed-type transducer, independent various beamforming can also be performed simultaneously at separate positions such that the generated beams do not overlap. Other virtual sources can also be used (see for instance, patent document 1) and for a high speed imaging, other beamforming methods can also be used.

According to the patent document 1, on the basis of the scanning with the ASTA beamforming (i.e., steering with a steering angle) and properly combinational use of the above-mentioned displacement measurement methods allows providing a new real time, high accuracy displacement vector measurement or a new real-time, high accuracy one-directional displacement measurement in a lateral direction primarily and in a depth direction, a new displacement measurement apparatus and a new US diagnosis apparatus.

PATENT DOCUMENT LIST

[PATENT DOCUMENT 1] JP-P2011-78744A, US 2011/0172538 A1
[PATENT DOCUMENT 2] U.S. Pat. No. 7,946,180 B2
[PATENT DOCUMENT 3] U.S. Pat. No. 7,868,824 B2
[PATENT DOCUMENT 4] U.S. Pat. No. 7,775,980 B2
[PATENT DOCUMENT 5] U.S. Pat. No. 7,690,838 B2
[PATENT DOCUMENT 6] US 2006/0173319 A1
[PATENT DOCUMENT 7] JP-P2007-152074A

NONPATENT DOCUMENT LIST

[NONPATENT DOCUMENT 1] C. Sumi et al, "Phantom experiment on estimation of shear modulus distribution in soft tissue from ultrasonic measurement of displacement vector field," IEICE Trans. on Fundamentals, vol. E78-A, no. 12, pp. 1655-1664, December 1995

[NONPATENT DOCUMENT 2] C. Sumi, "Fine elasticity imaging on utilizing the iterative rf-echo phase matching method," IEEE Trans. on Ultrasonics, Ferroelectrics, and Frequency Control, vol. 46, no. 1, pp. 158-166, January 1999

[NONPATENT DOCUMENT 3] C. Sumi, "Displacement vector measurement using instantaneous ultrasound signal phase—multidimensional autocorrelation and Doppler methods," IEEE Trans. on Ultrasonics, Ferroelectrics, and Frequency Control, vol. 55, pp. 24-43, January 2008

[NONPATENT DOCUMENT 4] C. Sumi, T. Kouno, Y. Suzuki, "3D imaging of shear modulus distribution in living soft tissues," Proc. of Autumn Meeting of Acoustical Society of Japan, pp. 1201-1202, September 1999 (in Japanese).

[NONPATENT DOCUMENT 5] C. Sumi, T. Ebisawa, "Phantom experiments of axial strain measurements using multidimensional autocorrelation method, multidimensional Doppler method and direct strain measurement method," Acoustical Science and Technology vol. 30, no. 2, pp. 117-123, 2009

[NONPATENT DOCUMENT 6] C. Sumi et al, "Effective lateral modulations with applications to shear modulus reconstruction using displacement vector measurement," IEEE Trans. on Ultrasonics, Ferroelectrics, and Frequency Control, vol. 55, pp. 2607-2625, December 2008

[NONPATENT DOCUMENT 7] C. Sumi et al, "Comparison of parabolic and Gaussian lateral cosine modulations in ultrasound imaging, displacement vector measurement, and elasticity measurement," Jpn, J. Appl. Phys., vol. 47 (5B), pp. 4137-4144, May 2008

[NONPATENT DOCUMENT 8] J. A. Jensen, "A new method for estimation of velocity vectors," IEEE Trans. on Ultrasonics, Ferroelectrics, and Frequency Control, vol. 45, pp. 837-851, 1998

[NONPATENT DOCUMENT 9] M. E. Anderson, "Multidimensional velocity estimation with ultrasound using spatial quadrature," IEEE Trans. on Ultrasonics, Ferroelectrics, and Frequency Control, vol. 45, pp. 852-861, 1998

[NONPATENT DOCUMENT 10] C. Sumi et al, "A demonstration of optimal apodization determination for proper lateral modulation," Jpn, J. Appl. Phys., vol. 48 (7B), July 2009

[NONPATENT DOCUMENT 11] C. Sumi et al, "Proper Analytic Point Spread Function for Lateral Modulation," Jpn, J. Appl. Phys., vol. 49 (7B), 07HF07, July 2010

[NONPATENT DOCUMENT 12] C. Sumi, "Increasing accuracy of tissue shear modulus reconstruction using ultrasonic strain tensor measurement—Lateral modulation and Regularization," Acoustical Imaging, vol. 29, pp. 59-68, Springer, 2008

[NONPATENT DOCUMENT 13] C. Sumi et al, "Ultrasonic agar phantom experiment for comparison of the measurement accuracy of tissue elasticity obtained by displacement vector measurement using lateral modulation with multidimensional autocorrelation and Doppler methods and corresponding one-dimensional methods," Journal of Reports in Medical Imaging, vol. 4, pp. 39-46, 2011

[NONPATENT DOCUMENT 14] J. A. Jensen, "A new estimator for vector velocity estimation," IEEE Trans. on Ultrasonics, Ferroelectrics, and Frequency Control, vol. 48, pp. 886-894, 2001

[NONPATENT DOCUMENT 15] M. E. Anderson, "A heterodyning demodulation technique for spatial quadrature," Proc. of 2000 IEEE Ultrasonics Symposium, pp. 1487-1490, 2000

[NONPATENT DOCUMENT 16] C. Sumi et al., "Increase in measurement accuracy of tissue displacement vector using rotation of coordinate system," IEICE Technical Report, US2010-82, pp. 25-32, November 2010

[NONPATENT DOCUMENT 17] C. Sumi, "Usefulness of ultrasonic strain measurement-based shear modulus reconstruction for diagnosis and thermal treatment," IEEE Trans. on Ultrasonics, Ferroelectrics, and Frequency Control, vol. 52, pp. 1670-1689, 2005

[NONPATENT DOCUMENT 18] C. Sumi and H. Yanagimura, "Reconstruction of thermal property distributions of tissue phantoms from temperature measurements—thermal conductivity, thermal capacity and thermal diffusivity," Physics in Medicine and Biology, vol. 52, pp. 2845-2863, 2007

[NONPATENT DOCUMENT 19] Y. Yamakoshi, J. Sato, and T. Sato, "Ultrasonic imaging of internal vibration of soft tissue under forced vibration," IEEE Trans. on Ultrasonics, Ferroelectrics, and Frequency Control, vol. 37, pp. 45-53, 1990

[NONPATENT DOCUMENT 20] C. Sumi, "Relative shear modulus reconstruction for visualization with no geometrical artifact," Acoustical Science and Technology, vol. 31, pp. 347-359, 2010

[NONPATENT DOCUMENT 21] C. Sumi, "Utilization of an ultrasound beam steering angle for measurements of tissue displacement vector and lateral displacement," Journal of Reports in Medical Imaging, vol. 3, pp. 61-81, 2010

[NONPATENT DOCUMENT 22] A. Manduca, D. S. Lake, S. A. Kruse, and R. L. Ehman, "Spatio-temporal directional filtering for improved inversion of MR elastography images," Medical Image Analysis, vol. 7, no. 4, pp. 465-473, December 2003

[NONPATENT DOCUMENT 23] J. Bercoff, M. Tanter, and M. Fink, "Supersonic shear imaging: a new technique for soft tissue elasticity mapping," IEEE Trans. on Ultrasonics, Ferroelectrics, and Frequency Control, vol. 51, pp. 396-409, 2004

[NONPATENT DOCUMENT 24] Y. C. Fung, "Foundations of solid mechanics," PRENTICE-HALL, INC. 1965

SUMMARY OF THE INVENTION

However, the present inventor confirmed that because the displacement measurement on the basis of the use of beamforming methods except for the above-mentioned LM beamforming (i.e., the multidirectional beamforming method, ASTA beamforming method, non-steered (frontal) beamforming, steered beamforming with a variable or invariable steering angle and among others) do not accurately use the beam angles actually generated, the measurement accuracy decreases. Usually, the beam angles used for the displacement calculation is determined at performing the beamforming using the delays set to respective arrayed vibrators, the errors in beam angle data caused by the actual directivities of the arrayed vibrators, the directions of scattering and reflection in the object, the attenuation, and their frequency modulations generated by their frequency-dependencies are not considered, and the actually generated beam direction is not used. The fact that the directions of actually generated beams change at positions is also not considered. The problem occurs for all the displacement measurement methods except for the above-mentioned case using the LM beamforming method using the estimates of instantaneous frequencies of all the directions. That is, also for the most conventional Doppler method and autocorrelation method for measurements of a displacement, a velocity and a strain in the beam direction, the same problem occurs. Also when the above-mentioned high intensity ultrasound and radiation force are generated, the same problem occurs. That is, the accuracy in a position of thermal treatment and in a mechanical source decreases (The problem also occurs for the treatments using mechanical waves such as a ballistic wave, an electromagnetic wave, a thermal wave etc.). In the current state of the art, by observing the generated temperature distribution, the achieved treatment effects (change in elastic properties and tissue degeneration), or the generated deformations or shear waves, only the following beamforming parameters are controlled, i.e., a direction of a single aperture or an arrayed-type, physical aperture of a transducer, and for such an arrayed-type transducer, delays or aperture directions set on respective vibrators (elements), an aperture width, an F-number, an apodization, a pulse shape, a pulse sequence (series) and a wavenumber etc. and transducer parameters such as element geometries, element widths, element pitches, element materials etc. such that a desired position is heated with a desired power and with a desired shape, or a desired mechanical source with a desired intensity and a desired power is generated at a desired position (the above-mentioned optimization method can also be used). The steering can also be performed (the above-mentioned optimization method can also be used). When dealing with a large region, foci are simultaneously or successively generated at plural positions. Otherwise, for applying a heat to the target, non-focusing may also be performed at transmission. For these cases, high accuracy measurement of generated beams or sound pressures is required. For imaging of a shear wave using a radiation force, in order to set the propagation direction of the shear wave in the lateral direction with respect to the depth direction, foci are temporally, successively generated at plural different depths (nonpatent document 23). Also for the high intensity ultrasound treatment and the generation of a mechanical source for generating deformations and shear waves, the present inventor proposed to perform not only beam steering but also LM beamforming (LM can also be performed in the lateral direction with respect to the set beam direction such as a steering direction) in order to achieve a high spatial resolution and a control for the generation of mechanical source and accordingly the directions of the deformations and shear wave propagations (non-patent document 6). For instance, the high intensity ultrasound treatment and the generation of the mechanical source can also be used for other plural functions such as echo imaging, tissue displacement measurement, radiation force imaging, shear wave imaging etc. This is similar for the use of other wave energies. However, the same problem occurs when using plural crossed beams. For instance, errors in crossing and focus positions occur. Thus, also when performing these high intensity ultrasound treatments and when generating a radiation force, in addition to the LM beamforming, the multidirectional beamforming, the ASTA beamforming, non-steered (frontal) beamforming, steered beamforming with a variable or invariable steering angle and other beamforming can be performed. However, also for such beamforming methods, the actually generated beams are not considered. When these beamforming methods are also used, although the echo imaging and tissue displacement measurement can be performed, the actually generated beams are not considered. This is similar for the echo imaging and displacement measurement using all the beamforming methods mentioned above. This is similar for the echo imaging and the displacement measurement on the basis of beamforming methods non-described here.

Because the direction of the shear wave propagation cannot be accurately measured, and further neither a proper propagation direction of shear wave nor a proper deformation direction cannot be obtained by the control of a mechanical or thermal source, it is impossible to estimate an anisotropic shear modulus (distribution) using measurement of a shear wave speed and it is difficult to obtain a high accuracy of the estimate using strain-tensor-measurement-based shear modulus reconstruction (for instance, patent documents 2 and 6; non-patent document 20).

Before using the present invention, when performing beam steering for displacement measurement and echo imaging, the inaccurately set steering angle data must be used for rotating the coordinate system at performing the beamforming or after performing the beamforming with time consumption such that the generated beam direction coincides with an axis of the coordinate system. For the coordinate rotation, the phase rotation can be performed using a complex exponential in a frequency domain (patent document 1). The method yields no errors during the coordinate rotation. However, conventionally the calculation time is decreased by performing interpolation such as a linear interpolation etc. The interpolation can be performed in a space or in a frequency domain. These calculations for the coordinate rotation can permit realization of non-real-time measurement and further lead to measurement errors due to the use of inaccurate steering angle data and approximate calculations if performed.

In addition, requiring the measurement accuracy increases a calculation time. Then, for a steered beam, plural beam angle data have not been used. That is, the meaningful use of spatial resolution on a beam direction (angle) has not been clarified. For the generation of above-mentioned high intensity ultrasound and radiation force, the same problem occurs. That is, for a generated beam, the beam direction and focus position etc. have not been accurately estimated. Neither the spatial resolution of the beam direction nor that of the focus position has not also been required (These are similar for other waves).

The rotation processing is performed to generate echo data for an arbitrary coordinate system (i.e., the Cartesian coordinate system or an arbitrary curvilinear orthogonal coordinate system such as a polar coordinate system etc.), after which a displacement measurement is performed through 1D, 2D or 3D signal processing. Then the processing is referred to as not a rotation processing but simply an interpolation processing. This kind of interpolation processing is used to interpolate measurement results, i.e., echo imaging (at beamforming or after beamforming) and measurements of displacement and others. Because the results are usually imaged on the Cartesian coordinate system, the interpolation is used to convert the result data exhibited on an arbitrary coordinate system into those exhibited on the Cartesian coordinate system. The coordinate system and vision of field to be used depend on the aperture geometry of a transducer. However, the generation of echo data (i.e., beamforming) can also be performed on the Cartesian coordinate system at the initial stage, and in such a case, the echo imaging can be achieved simply. The measurement can also be performed on the Cartesian coordinate system obtained in such ways, and in such cases, the displaying of the measurement results is also simple. However, when performing the measurement on an arbitrary orthogonal coordinate system (for instance, an arbitrary curvilinear orthogonal coordinate system such as a polar coordinate system), the measurement results obtained are converted into those exhibited on the Cartesian coordinate system through interpolation. In addition, after converting echo data obtained on an arbitrary orthogonal coordinate system into those exhibited on the Cartesian coordinate system through the interpolation as mentioned above, the measurement can also be performed.

Regarding echo imaging, when employing the LM beamforming as an operation mode, the above-mentioned several methods can be used for generating an echo data frame. However, it takes a long time to complete the echo data frame generation except for the use of the synthetic aperture method and simultaneous transmissions/receptions of plural crossed beams. The LM beamforming requires more processing than the conventional beamforming, and when obtaining the crossed beams from beams generated at different times, the displacement generated between the time difference leads to degradation of an echo image to be generated in addition to that of the measurement accuracy of displacement. Then, the present inventor developed the mirror setting method for the ASTA beamforming (patent document 1). However, the image to be obtained by generating locally mirrored echo data is a quasi-LM echo image that looks like to exhibit a LM image. Consequently, for an ultrasound wave as well as other waves, the present inventor reached the consideration about the meaningful generation of LM on the basis of the conventional non-steered (frontal) beamforming or the ASTA beamforming. These are similar for other waves.

In view of these points, the displacement measurement method related to a viewpoint yields for a displacement measurement on the basis of the ASTA beamforming method, the non-steered (frontal) beamforming method, the beam steering method with a variable or invariable steering angle, the LM beamforming method, the multidirectional beamforming method or other beamforming methods, high accuracy measurement of a displacement component, a velocity component or a strain tensor component in a beam direction by considering the directivities of US vibrators (elements), directions of scattering and reflection, attenuation and their frequency modulations due to the physical phenomena, i.e., by calculating an actually generated beam direction at each position of interest with a high accuracy from echo data generated. The displacement measurement method includes the present inventor's developed multidimensional autocorrelation method, multidimensional Doppler method (i.e., moving-average processing is performed in a multidimensional space), spectra frequency division method (patent document 1 and non-patent document 16 etc.: the multidimensional autocorrelation method or the multidimensional Doppler method is applied to beams with the same zero or non-zero steering angle on an arbitrary orthogonal coordinate system used) or coherent superposition method that permits the generation of new beam properties (for instance, patent documents 6 and 7, non-patent documents 3, 6, 7 etc.) etc.

When the system of equations of which number of equations are larger than that of unknown displacement components, the least squares method can be used to solve the system of equations; otherwise, additional averaging can also be performed on the results obtained from a single equation or systems of equations with more than two equations (for instance, patent documents 1 and 6 etc.). When using the least squares method, to obtain a stable measurement result, the regularizations can be performed (for instance, patent documents 2, 4, 6 and 7 etc.). Other regularizations from ones disclosed in the documents can also be performed. As above-mentioned, the present inventor proposed to perform the high intensity ultrasound treatment and/or the radiation force imaging on the basis of the use of apparatuses that permit displacement measurement. Then, the transducer works as either a high intensity ultrasound applicator or a radiation force applicator, or both of the high intensity ultrasound and radiation force applicators (there is also a case where a thermal source and a mechanical source are generated simultaneously by the same transmission of ultrasounds). Then, the apparatuses proposed by the present inventor permit reception of echo signals and echo imaging with respect to the transmission of a high intensity ultrasound and/or a radiation force; and also permit measurement of displacements generated by the transmission (patent document 2 etc.). Therefore, the use of the present invention for such apparatuses permits measurement of generated beams with a high accuracy and with a high spatial resolution if required, and then permits high accuracy control of a treatment (thermal source) and a mechanical source (deformation or shear wave propagation). The thermal and mechanical sources can be respectively plural. Even if a high intensity ultrasound or radiation force imaging apparatus does not employ any displacement measurement methods, permitting reception of echo signals and using of the present invention also allows the high accuracy control of treatment and/or shear wave and deformation.

As will be disclosed in detail below, the present invention permits for these applications, high accuracy measurement and with a high spatial resolution if necessary, of the beam direction, the direction to a focus, the focus position, the crossing position of beams, the sound pressure shape distribution (1D, 2D or 3D distribution), the beam shape etc. The present invention can also be used for echo imaging.

If a distribution of shear waves can be measured, the directions and the distribution of directions of shear waves can be measured with a high accuracy. If temporal series data of the shear wave distributions can be obtained, high accuracy measurement of shear wave propagation is permitted. If the control of the mechanical or thermal source is permitted, shear waves with proper propagation directions can be generated; and permitting measurement of shear wave propagation speeds in various plural directions allows estimating an anisotropic shear modulus (distribution). Also permitting generation of deformations in proper directions allows high accuracy measurement of an isotropic or anisotropic shear modulus through the use of strain-tensor-measurement-based shear modulus reconstruction method, because strain tensor data can be obtained with respect to variously directional deformations.

These are similar when other waves are used.

Moreover, the present invention uses the sense that the lateral frequency also exists, and then the present invention includes the uses of the present inventor's developed multidimensional autocorrelation method, multidimensional Doppler method (the moving-average is multidimensional), spectra frequency division method (patent document 1 and non-patent document 16 etc.: the multidimensional autocorrelation method or the multidimensional Doppler method is applied to beams with the same zero or non-zero steering angle on an arbitrary orthogonal coordinate system used), coherent superposition method (for instance, patent documents 6 and 7; non-patent documents 3, 6, 7 etc.) etc. (moving-average is performed in a multidimensional space). The one-directional displacement measurement method can also be used (moving-average processing should be performed in a multidimensional space). When the spectra frequency division method is used, although the calculation time is required, the use of high accuracy data of beam angles leads to a high accuracy of displacement measurement. In such a case, the coordinate rotation is also performed for the use of the one-directional displacement measurement method or the multidimensional displacement vector measurement method.

As disclosed below, although the present invention is explained in detail using ultrasound echo signals or wave dynamics of shear waves and apparatuses related to the waves, the present invention can also be used for other arbitrary waves and apparatuses that use the waves. The present invention can also be used for observing not only reflection or scattering waves but also transmission waves.

According to the viewpoint of the present invention, high accuracy measurement of the one-directional displacement is achieved (in almost cases, in lateral, axial or radial direction etc.). When using the multidirectional beamforming method, the present invention can be used for the respective steered beams to yield high accuracy measurements of displacement components in the beam directions, from which an arbitrary directional displacement vector can be synthesized and measured with a considerably high accuracy.

Before performing the present inventions, the coordinate rotation is required to set the beam direction to the direction of one of the coordinate system axes with a calculation time at performing the beamforming or after the beamforming in order to achieve high accuracy measurement of the displacement component in the actually generated beam direction. However, the use of the present invention permits real-time and high accuracy measurement without the coordinate rotation. At first, through the consideration about the requirement of a spatial resolution in the beam angle and the application of the invention exposed in the patent document 1, the present invention leads to a useful coordinate rotation using beam angle data measured with a spatial resolution at respective positions. Furthermore, the present invention achieves real-time and high accuracy measurement of a displacement component in the actually generated beam direction by setting the actually generated beam direction through the high accuracy measurement of a beam angle at each position of interest. That is, the real-time and high accuracy measurement is achieved through calculation of the displacement component in the beam direction using the instantaneous phase change and instantaneous frequency in the beam direction at each position of interest without the coordinate rotation processing. This can also be used for echo imaging. Specifically, not only the actually generated beam direction, but also the direction to a focus position, the focus position, the position of beam crossing, the sound pressure shape distribution (1D, 2D or 3D distribution) and the beam shape etc. can be measured with a high accuracy and with a high spatial resolution if necessary. For instance, for echo imaging with the LM beamforming or the multidirectional beamforming, the present invention can also be used to obtain high measurement accuracies of the positions of beam crossing and focus. For instance, when using the coherent superposition method, the present invention can also be used for the estimation or design of not only the beam angles of generated echo signals and those of the respective echo signals superposed. When using the spectra frequency division method, such estimation and design can also be performed for generated quasi-beams. For such estimation and design, the point spread function desirable for displacement measurement (i.e., parameters: envelop, frequencies, bandwidths, wavenumbers etc.; the parameters are desired to be multidimensional.) is obtained through experiments and simulations (optimization can also be performed with respect to the parameters using a signal-to-noise ratio (SNR) of echo data (echo SNR) obtained or to be obtained, measurement errors obtained or to be obtained etc. as a measure.), and beamforming parameters and transducer parameters are optimized through the above-mentioned optimization using experimental displacement measurement data or simulations (the database can be permitted to be made and used.). The experimental data or simulation data can also be used as constraints for the above-mentioned optimization. The optimization can also be performed directly using the echo SNR, measurement accuracy and measurement error. The point spread function desirable for echo imaging (i.e., parameters: envelop, frequencies, bandwidths, wavenumbers etc.; the parameters are desired to be multidimensional.) is also obtained through experiments and simulations (optimization can also be performed with respect to the parameters using an echo SNR obtained or to be obtained, a contrast obtained or to be obtained, an image quality quantitatively evaluated using the present invention or visually confirmed, etc. as a measure.), and beamforming parameters and transducer parameters are optimized through the above-mentioned optimization using experimental displacement measurement data or simulations (the database can be permitted to be made and used.). The experimental data or simulation data can also be used as constraints for the above-mentioned optimization. The optimization can also be performed directly using the echo SNR, contrast, image quality quantitatively evaluated using the present invention or visually confirmed, etc. Regarding the applications, as disclosed in detail below, parameters such as a window used for filtering spectra etc. related to the coherent superposition method and spectra frequency division method are also optimization targets. For the calculation of an SNR, if the S (signal) is unknown or cannot be strictly determined etc., S is assumed; or N is estimated using a standard deviation or a variance etc.; thus the accuracy of the targets can also be estimated. Instead of the SNR, the standard deviation or variance etc. can also be used (as disclosed in detail below, such an accuracy can also be estimated similarly.).

Also with respect to the high intensity ultrasound treatment and radiating a force, the direction of beam and direction to the position of a focus (as mentioned above, plural foci can also be generated by performing simultaneous or successive transmissions.), position of foci, position of beam crossing, sound shape pressure distribution (1D, 2D or 3D distribution), beam shape etc. can also be measured with a high accuracy and with a high spatial resolution if necessary, high accuracy (minimum-invasive) treatment and shear modulus imaging can be performed by controlling a temperature change, a treatment effectiveness, deformations and shear wave propagations using controlled mechanical sources and thermal sources. When performing the high intensity ultrasound treatment and radiating a force, imaging using correspondingly obtained echo signals and tissue displacement measurement can also be performed. Measuring a shear wave distribution permits a distribution of the propagation directions of shear waves being measured with a high accuracy; and then measuring temporal series data of the shear wave distribution permits high accuracy measurement of shear wave propagation speed. Permitting the control of a mechanical or thermal source allows the generation of shear waves with proper propagating directions; and then measurement of the propagation speeds in plural various directions permits measurement of an anisotropic shear modulus (distribution). Permitting measurement of deformation in a proper direction also allows high accuracy measurement of an isotropic or anisotropic shear modulus through the measurement of strain tensors for variously directional deformations and the use of the strain-tensor-measurement-based shear modulus reconstruction. Also with respect to generated or arrived arbitrary waves (mechanical wave, electromagnetic wave, thermal wave etc.), the propagation direction, propagation speed, related material properties can also be measured.

For such applications, on the basis of the specific evaluation of the present invention, a thermal or mechanical source (specifically, single or plural sources) or a sound pressure (parameters: sound pressure shape or intensity etc.; and the parameters are desired to be multidimensional) desirable for allowing the control of heating, deformation direction or shear wave propagation direction is obtained through experiments and simulations (optimization can also be performed using the heating efficiency, temperature rising, heating effectiveness (degeneration), deformation, strain tensor, strain rate tensor, acceleration vector, displacement vector, velocity vector, propagation direction or propagation speed of shear wave etc. as a measure), and beamforming parameters and transducer parameters are optimized through the above-mentioned optimization using experimental measurement data on the heating efficiency, temperature rising, heating effectiveness (degeneration), deformation, strain tensor, strain rate tensor, acceleration vector, displacement vector, velocity vector, propagation direction or propagation speed of shear wave etc. or simulations (the database can be permitted to be made and used.). When the mechanical or thermal sources are plural, the respective sources can be independently or simultaneously optimized. The experimental data or simulation data can also be used as constraints for the above-mentioned optimization. The optimization can also be performed directly using the heating efficiency, temperature rising, heating effectiveness (degeneration), deformation, strain tensor, strain rate tensor, acceleration vector, displacement vector, velocity vector, propagation direction or propagation speed of shear wave etc. instead of the parameters related to the sound pressure, thermal source or radiation force.

The above-mentioned designs for the respective uses (that can also be performed with trial and error) can also be performed with respect to the same measure with proper control or not; otherwise, the respective measures for the uses are simultaneously used to achieve a design. Thus, the same beamforming can also be performed for plural uses. Also the above-mentioned desirable point spread functions to be used for the respective optimizations (uses) can also be set to the same point spread function with proper control or not; otherwise, respective measures for the optimizations (uses) are simultaneously used to obtain an optimized point spread function. Through such optimizations, the same beamforming can also be performed for plural uses.

Regarding echo imaging, when employing the LM beamforming as an operation mode, the above-mentioned several methods can be used for generating an echo data frame. However, when performing the conventional non-steered (frontal) beamforming or the ASTA beamforming, the present invention yields the LM beamforming simply in a short time. In this case in addition to the cases where the original LM beamforming is performed (non-patent document 3, 6, 7 etc.), after completing the respective beamforming, lateral cosine modulation and lateral sine modulation are exchangeable for each other. That is, echo imaging and displacement measurement can be performed properly. Instead of echo signals, transmission waves can also be detected and used.

DESCRIPTION OF THE PREFERRED EMBODIMENTS

The following is explanation in detail of conduct forms of the present invention with referring to figures.

Figure 1:
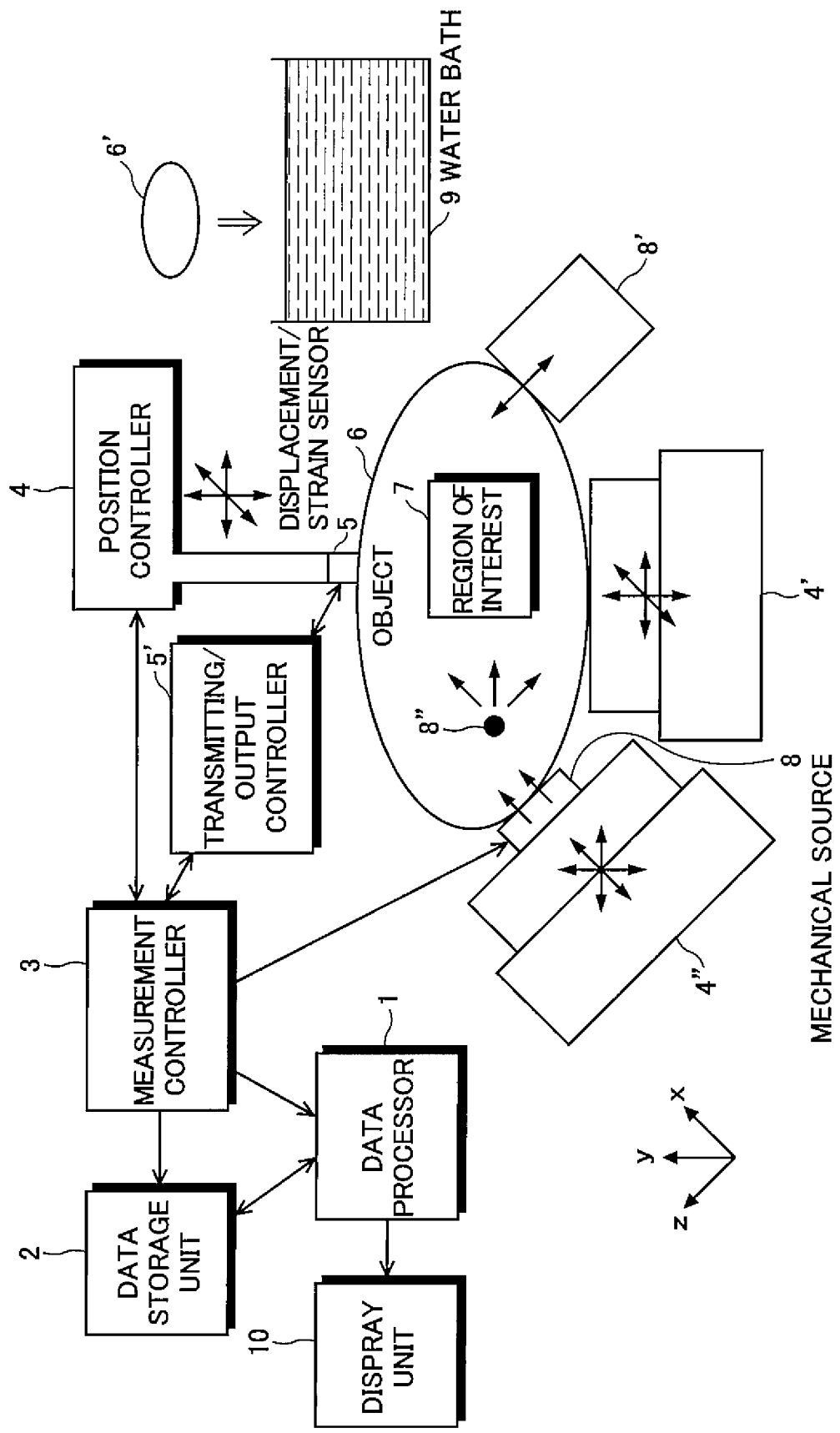
FIG. 1 shows schematic representation (block map) of a global frame of apparatus of echo imaging and displacement measurement related to one of conduct forms of the present invention.

FIG. 1 shows a schematic representation of a global frame of the imaging and displacement measurement apparatus, related to one of conduct forms of the present invention. This apparatus measures in 3D, 2D or 1D (primarily in the lateral direction) ROI 7 set in the measurement object 6 the displacement vector component (distributions or temporal series), strain tensor component (distributions or temporal series), instantaneous phase change (distribution or temporal series), shear wave propagation speed or propagation direction (distributions or temporal series), shear wave vibration displacement (or velocity or acceleration), shear wave vibration amplitude, shear wave vibration frequency, shear wave vibration direction, shear wave phase (distributions or temporal series), their temporal or spatial partial derivative distributions, etc. to obtain the strain tensor field, strain rate tensor field, acceleration vector etc., of which results are used by this apparatus to measure distributions of shear modulus, Poisson's ratio, visco shear modulus, visco Poisson's ratio, delay times or relaxation times, density, viscosities etc. This apparatus performs the imaging and displacement measurement methods related to one of conduct forms of the present invention. This apparatus composes the ultrasound diagnosis apparatus related to one of conduct forms of the present invention.

As shown in FIG. 1, the displacement/strain sensor 5 can be permitted to be directly contacted onto the object surface, or proper medium can be permitted to be put between the sensor and the object. On this conduct form, as the displacement/strain sensor 5, a US transducer can be permitted to be used. The transducer can have a 1D or 2D array of plural US vibrators (elements). A US transducer with a single vibrator can also be permitted to be used. A single or plural US vibrators transmit ultrasounds with respect to a single or plural driving signals, and the single or plural US vibrators also receive US echoes to output a single or plural received signals. Through transmission beamforming processing, ultrasounds transmitted from the single or plural US vibrators form a US transmission beam, and through reception beamforming processing, ultrasounds received by the single or plural US vibrators form a US reception beam.

The distance between the object 6 and displacement/strain sensor 5 can be permitted to be mechanically controlled by the position control unit 4. Otherwise, the relative distance between the object 6 and displacement/strain sensor 5 can also be permitted to be mechanically controlled by the position control unit 4'. Moreover, the ultrasound transmitter and ultrasound pulser (driving control unit) 5' is equipped with to generate the single or plural driving signals for driving the displacement/strain sensor 5, and 5' also serves as the output control unit, i.e., the receiver and amplifiers of the single or plural received signals (echo signals) outputted from the displacement/strain sensor 5. Furthermore, the mechanical source such as a compressor/a vibrator etc. or source of a radiation force (i.e., 8 or 8') can be permitted to be equipped with in order to apply deformation to the object 6, and the mechanical position control unit 4" can also be permitted to be equipped with. The US transducer body can also be permitted to be used a mechanical source (i.e., a compressor or a vibrator) or a radiation force can also be permitted to be generated (radiated) from the US transducer. Such a radiated force, or internal heartbeat or blood pulsation can also be permitted to be used as a mechanical source 8".

The echo signals outputted from the driving/output control unit 5' are stored at the data storage unit 2 via the measurement control unit 3. Then, the driving/output control unit 5' can be permitted to be internally equipped with analogue-to-digital (AD) convertors, or the AD converters can also be permitted to be externally equipped with. As mentioned below, the driving/output control unit 5' performs the transmission beamforming; and additionally the driving/output control unit 5' can also permit to perform the reception beamforming. In such a case, a US echo data frame generated from the reception-beamformed echo signals can be permitted to be stored at the data storage unit 2. Otherwise, plural received signals outputted from the US vibrators (elements) can be permitted to be stored at the data storage unit 2 before the reception beamforming is performed. In such a case, the data processing unit 1 reads, out the plural received signals and also performs the reception beamforming to generate a US echo data frame. Over a laterally large ROI with an arbitrary direction, ultrasounds can be permitted to be transmitted using plural US vibrators (elements) at the same time or at the same temporal phase; and SA (synthetic aperture) processing can also be permitted to be performed on the basis of US transmissions from the respective US vibrators (elements) (In the case, as a feature of SA processing, dynamic focusing can be permitted to be performed for synthesizing a transmission beam in addition to synthesizing a reception beam.). The generated US echo data frame can be permitted to be stored at the data storage unit 2 via the measurement control unit 3.

Regardless the way of reception beamforming, if the measurement control unit outputs a command to perform the displacement measurement, the displacement vector component (distributions or temporal series), one-directional displacement (distribution or temporal series), instantaneous phase change (distribution or temporal series), shear wave propagation speed or propagation direction (distributions or temporal series), shear wave vibration displacement (or velocity or acceleration), shear wave vibration amplitude, shear wave vibration frequency, shear wave vibration direction, shear wave phase (distributions or temporal series) etc. generated at an arbitrary temporal phase in the ROI 7 are calculated via performing below-mentioned processing on plural US echo data frames generated at different temporal phase. In the first case, the data processing unit 1 reads out the US echo data frame from the data storage unit 2 and subsequently performs the calculations. In the second case, the reception beamforming or the calculations can also be permitted to be performed via other data processing units.

The data processing unit 1 can also permit to calculate their temporal or spatial partial derivative distributions, i.e., strain (tensor components, distributions, temporal series), strain rate (tensor components, distributions, temporal series), acceleration (vector components, distributions, temporal series), velocity (vector components, distributions, temporal series) etc. That is, when the displacement (vector components, distributions, temporal series) generated in the ROI 7 are calculated, the strain (tensor components, distributions, temporal series) are calculated by implementing a 3D, 2D, or 1D spatial differential filter to the calculated displacement (vector components, distributions, temporal series). The cut-off frequencies of the filters used in the present invention can be set different values freely at each position and at each time in the respective spatial and temporal directions similarly to those used generally. The acceleration (vector components, distributions, temporal series) can be permitted to be calculated by implementing a temporal differential filter twice to the temporal series of calculated displacement (vector components, distributions). The strain rate (tensor components, distributions, temporal series) can be permitted to be calculated by implementing a spatial differential filter to the velocity (vector components, distributions, temporal series) calculated through the implementation of a temporal differential filter to the displacement (vector components, distributions, temporal series), or by implementing a temporal differential filter once to the temporal series of strain (tensor components, distributions). Also the shear wave propagation speed or propagation direction (distributions, temporal series) can be permitted to be calculated through the measurement of position have a change in an instantaneous phase. This is a simple method with a non-required time. However, the measurement accuracy is low in the sense that the spatial resolution is determined by the sampling intervals used etc. As an alternative method, the shear wave propagation direction (distribution) is accurately measured by calculating a shear wave distribution at respective times, or the shear wave propagation speed is accurately measured by calculating temporal series data of a shear wave distribution through accurate measurements of a shear wave vibration displacement (or velocity or acceleration), shear wave vibration amplitude, shear wave vibration frequency, shear wave vibration direction, shear wave phase (distributions or temporal series). a shear wave vibration displacement (or velocity or acceleration), shear wave vibration amplitude, shear wave vibration frequency, shear wave vibration direction, shear wave phase (distributions or temporal series). As a method for measuring the shear wave propagation speed at a time, the above-mentioned methods for measuring a displacement or a displacement vector can be applied to at least more than two shear wave distributions generated at different temporal phases including the time. A high intensity US applicator or a radiation force applicator, or displacement/strain sensor 5 also working as one of the applicators or both applicators can be permitted to be used to control a thermal source or a mechanical source in order to generate a shear wave propagating in a proper direction. In addition, by measuring shear wave propagation speed in proper plural directions, an anisotropic shear modulus (distribution) can be permitted to be estimated. Otherwise, with respect to the target deformed in a proper direction, measurements of strain (tensor) etc. can be permitted to be used for reconstructing of mechanical properties such as a shear modulus etc. as disclosed below. Strain (tensor) data measured at various directional deformations can be permitted to be used for measurement of isotropic or anisotropic physical properties.

Moreover, the data processing unit 1 can allow calculating a shear modulus distribution, a Poisson's ratio distribution, visco-shear modulus distribution, visco-Poisson's ratio, delay time distributions, relaxation time distributions, a density distribution, a viscosity distribution etc. from strain (tensor components, distribution, temporal series), strain rate (tensor components, distribution, temporal series), accelation (vector components, distribution, temporal series) etc. measured using the data processing unit 1 itself (for instance, patent documents 2 and 6; non-patent document 20). Otherwise, as mentioned above, the shear modulus distribution can also be permitted to be measured using the measured shear wave propagation speed. In the present invention, other physical properties such as a density, a bulk modulus, viscoelasticity constants, etc. required for the shear modulus measurement are set at measured or typical values. Occasionally, only the density can also be used approximately. The density can also be assumed to be a constant. Physical properties to be measured are isotropic or anisotropic. The calculation results can be permitted to be stored at the data storage unit 2.

The measurement control unit 3 can permit to control the data processing unit 1, the data storage unit 2, the position control units 4 and 4", and the driving/output control unit 5'. These position control units 4, 4' and 4" can also be permitted to be operated directly by a hand of measurer and the positions of the displacement/strain sensor 5 and the mechanical source 8 can be permitted to be determined. When the object 6 is spatially fixed, the position control unit 4' is not used. When the displacement/strain sensor 5 is an electronic scan type, the position control unit 4 is not always used. That is, according to the size of an ROT 7, it can be permitted to perform the measure without mechanical scanning.

The displacement/strain sensor 5 can be permitted to be contacted onto the object 6 or not. When performing the monitoring of treatment effectiveness with respect to the high intensity ultrasound, the displacement/strain sensor 5 and object 6 can be permitted to be dipped in or immersed in a water tank. As mechanical sources, in addition to a compressor, a vibrator (a transducer body can permit to work as the compressor or vibrator), other mechanical sources such as a high intensity ultrasound (a transducer can also permit to work as the high intensity ultrasound transmitter.), a radiated force (a transducer can also permit to work as the force radiator.) etc., and internal, uncontrollable mechanical sources (when observing living tissues, for instance, hear motion, respiratory, blood vessel, body motion etc. lung, air, blood vessel, blood etc. can also be permitted to be included in an ROI.) can also be permitted to be used. The high intensity ultrasound and radiation force can also be permitted to be generated to obtain both the effects simultaneously. Otherwise, control of a driving energy or a shape of the radiated signal wave can permit to change the operation mode.

The specific evaluation on a generated beam using the present invention disclosed below (a beam direction, a direction to a focus, a focus position, a position of beam crossing, a shape of sound pressure (1D, 2D or 3D sound pressure distribution), a beam shape etc.) is performed by the data processing unit 1. When performing the specific beam evaluation on a high intensity US treatment or a pressure radiation, a reception beamforming is performed similar to in the cases where the tissue displacement measurement or echo imaging. The echo signals obtained with respect to the high intensity US treatment or pressure radiation can also be permitted to be used for echo imaging or tissue displacement measurement for the displacement generated at that time. Optimization processing can be permitted to be performed by the data processing unit 1 for the above-mentioned displacement measurement, echo imaging, high intensity US treatment and pressure radiation.

Figure 2:
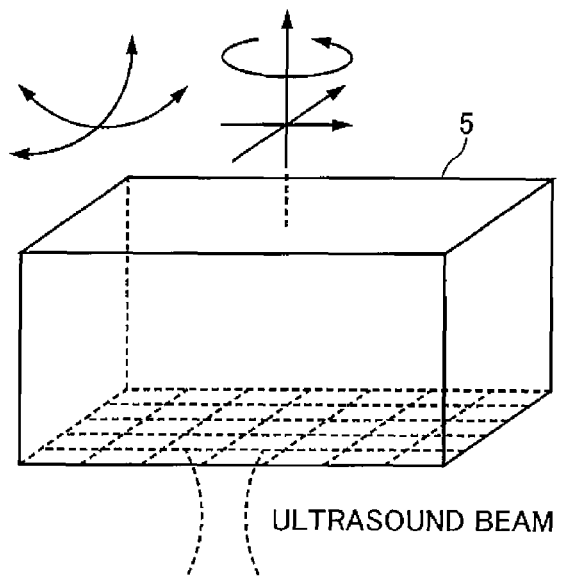
FIG. 2 shows illustration of mechanical scan movements of displacement/strain sensor.

FIG. 2 shows illustration of mechanical scan movements of displacement/strain sensor. The movement of displacement/strain sensor 5 includes a mechanical steering. For instance, regarding the position control unit 4 shown in FIG. 1, as shown in FIG. 2, the position control unit 4 can permit the mechanical movements such as vertical or horizontal rigid motion, turn and fan direction scan movements, which is mechanically or in a handy manner.

Referring to FIG. 1, the output of the driving/output control unit 5' is also stored at the data storage 2 in a temporally successive manner or with a preset time interval. The data processing unit 1 controls the driving/output control unit 5' via the measurement control unit 3, and acquires the echo's basic wave component (n=1) and n-th harmonic wave components (n=2 to N), or all the components in an ROI 7, and implements the above-mentioned data processing to the echo data in order to yield the displacement data, strain data, strain rate data, or acceleration data.

Figure 3:
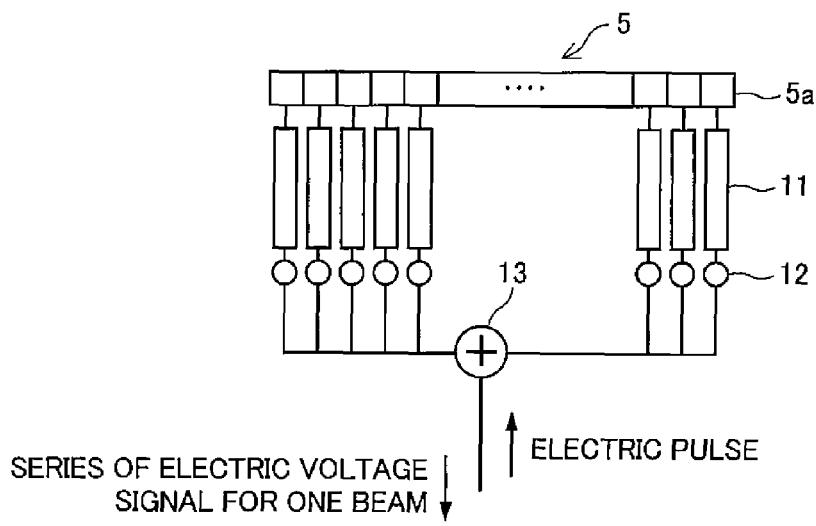
FIG. 3 shows illustration of components for realizing beamforming, i.e., apodization, switching, delay processing, phase matching, summation processing.

The driving/output control unit 5' and the data processing unit 1 obeys with respect to the commands outputted from the measurement control unit 3, and carry out beamforming with respect to the driving signals and echo signals, e.g., processing such as fixed focusing transmission, multiple fixed focusing transmission, dynamic focusing reception, etc. Furthermore, apodization can also be permitted to be carried out on the ultrasound intensity. For instance, the beamforming is performed with performing the weighting on ultrasounds transmitted/received by respective vibrators (elements) to sharpen the ultrasound beam (apodization), and the echo signals of 3D (2D or 1D) ROI are acquired. Such processing is permitted to be performed by functions such as apodization, switching, delay processing, phase matching, summation processing etc. installed in conventional US diagnosis apparatuses. FIG. 3 shows illustration of components for realizing the beamforming.

FIG. 3 shows illustration of components for realizing the beamforming, i.e., apodization, switching, delay processing, phase matching, and summation processing. The respective US vibrators (elements) 5a of the displacement/strain sensor 5 are connected to delay elements 11 via amplifiers, and the delay elements 11 are connected to apodization elements or switches 12. The apodization elements are comprised of amplifiers or attenuators etc., and the switches have the function for selecting on or off of the corresponding channels. The delay elements 11, and apodization elements or switches 12 are controlled via the measurement control unit 3 (FIG. 1). Plural apodization elements or switches 12 are connected to the summation unit 13.

When performing the reception of the US echo signals, plural echo signals outputted from plural US vibrators (elements) 5*a* via the amplifiers, delay elements 11, and apodization elements (multiplication or division can also be permitted to be performed using calculator.) or switches are summed by the summation unit 13. As the results, a received signal expressing the reception beam with reception focuses is generated. The signal is converted into the digital signal via an analogue-to-digital (A/D) convertor and a US echo data frame is generated.

When performing the transmission of a US beam, the driving signal is provided to the plural US vibrators (elements) 5*a* by the summation unit 13 via the apodization elements or switches 12, delay elements 11 and amplifiers etc. All the comprising elements 11 to 13 can also be permitted to be realized by the data processing unit 1 shown in FIG. 1, and partially the driving/output control unit 5' can also be permitted to be used to realize the comprising elements. The order of the comprising elements to be used can be permitted to be changed and the comprising can also be permitted to be various and other from the above-mentioned comprising.

On the present conduct form, these comprising elements generate the above-mentioned non-steered (frontal) beamforming (scanning), the above-mentioned multidirectional beamforming (scanning), the above-mentioned ASTA beamforming (scanning) etc. and if required, the object 6 can be scanned laterally (i.e., in a lateral direction with respect to the depth direction) using steered beams. Thus, echo data frames are generated. Otherwise, ultrasounds can be transmitted at the same time or at the same temporal phase with respect to a laterally large ROI with an arbitrary direction, or the synthetic aperture (SA) processing can also be performed to obtain echo data frames that can be obtained using such scanning methods. The respective positions in the object 6 are not always scanned in a parallel condition. When performing beam steering, the beamforming can be permitted to be performed such that a large steering angle or a crossing angle can be obtained at the respective positions in the ROI. When performing the synthetic aperture (SA) processing, the received signals filtered or amplified properly are converted to the digital signals via A/D convertors and all other processing can also be permitted to be performed using a calculator. The synthetic aperture can also be permitted to be performed on the combination of the use of a single vibrator and mechanical scanning etc.

Figure 4:
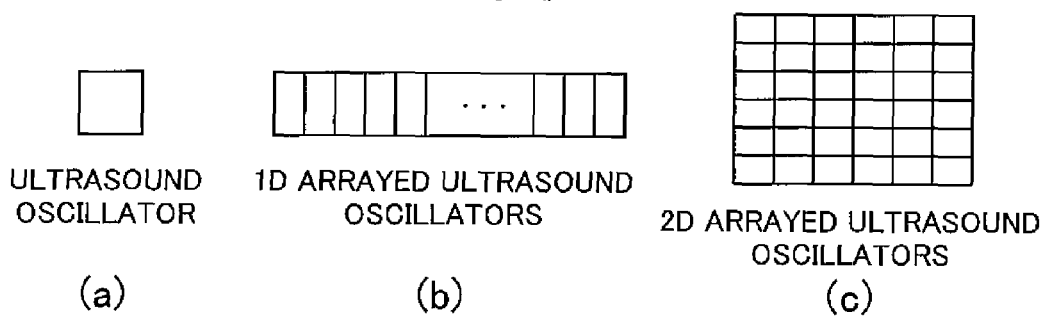
FIG. 4 shows illustration of displacement/strain sensors applicable to the present invention.

FIG. 4 shows illustration of displacement/strain sensors 5 applicable to the present invention. On this conduct form, as the displacement/strain sensor 5, the following type ultrasound transducers can be permitted to be utilized, i.e., 2D or 1D arrayed vibrators (elements) being electronic scanning possible, or 2D or 1D arrayed vibrators (elements) being mechanical scanning possible. A non-arrayed-typed transducer (sensor) possible with a mechanical scanning can also be permitted to be used. Otherwise, arbitrary transducers such as a sector-type transducer etc. can also be permitted to be used. When performing the beam steering, in order to increase the steering angle, the object 6 can be permitted to be mechanically scanned with such transducers (the signal-to-noise ratio of reception signals with respect to generated, steered beams decreases if the steering angle becomes out of the range of a directivity of the US vibrator (element) when the beam steering is performed only with electrical scanning.).

Figure 5:
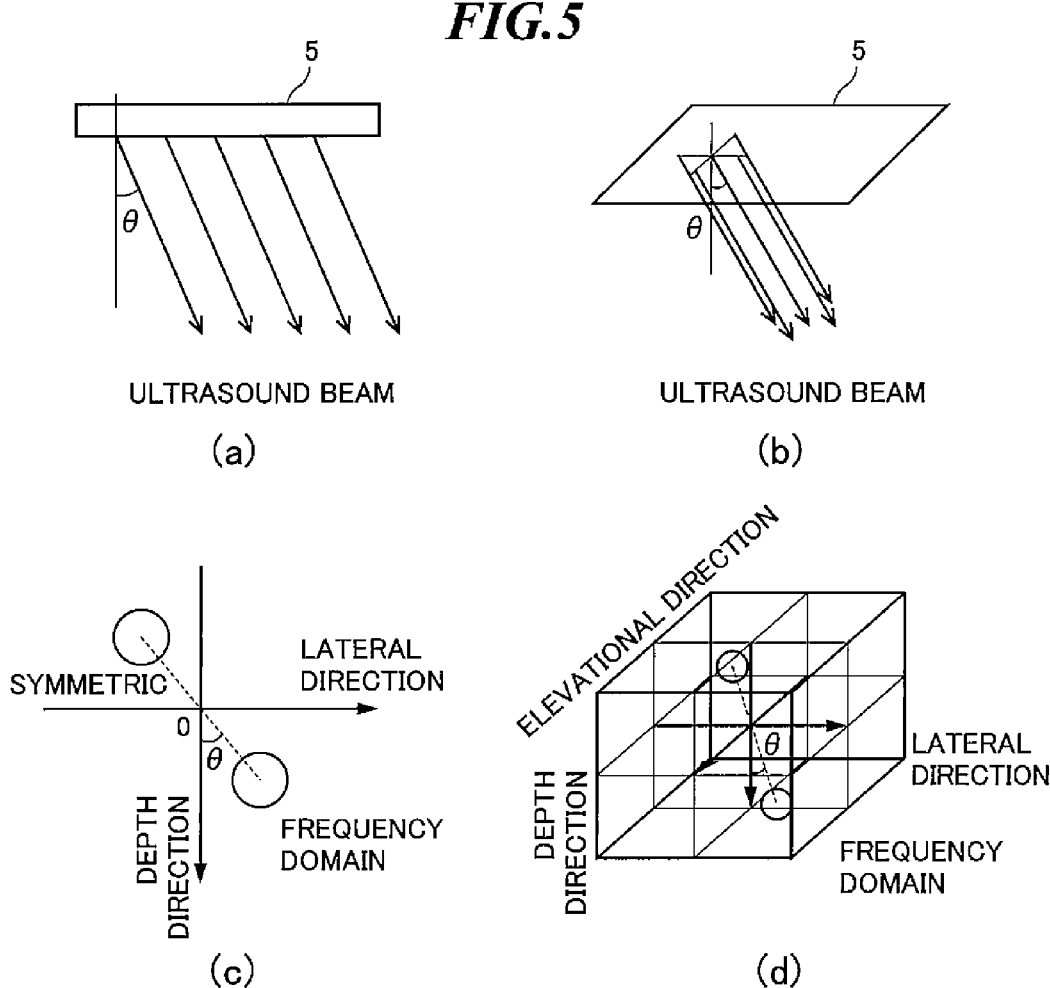
FIG. 5(a) and FIG. 5(b) respectively show illustrations of lateral scan using steered beams with a steering angle (ASTA) over 2-dimensional and 3-dimensional regions of interest.
FIG. 5(c) and FIG. 5(d) respectively show illustrations of the corresponding 2-dimensional and 3-dimensional spectra.
Figure 6:
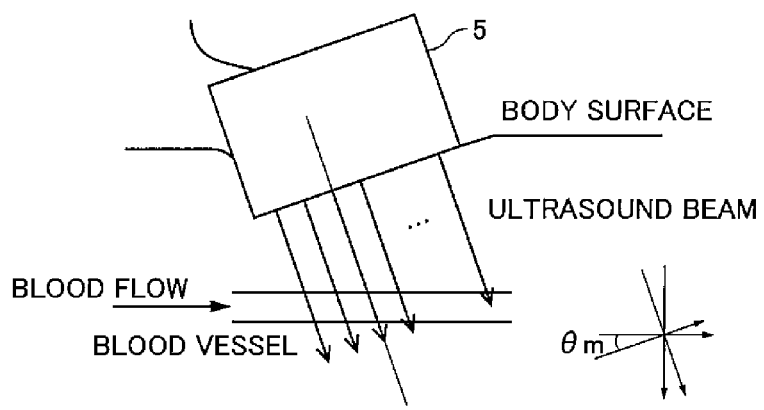
FIG. 6 shows illustration of beam steering using mechanical scan.

FIG. 5 shows an illustration of a lateral scan using steered beams with ASTA (the same single steering angle), in which $\theta$ expresses the steering angle ($0°<\theta<90°$). Non-steered beamforming (i.e., in a frontal direction with respect to a physical effective aperture) corresponds to that in a case with $\theta=0°$. FIG. 5(*a*) shows the scanning of a 2D region using a 1D array, whereas FIG. 5(*b*) shows the scanning of a 3D space using a 2D array. FIG. 6 shows illustration of beam steering using mechanical scanning, in which $\theta m$ shows the steering angle generated ($0°<\theta m<90°$). The beamforming in the depth direction corresponds to in the case with $\theta m=0°$. When generating the echo data frame or after generating the echo data frame, with respect to the object, a proper 3D orthogonal coordinate system involving the existence of three axes of a depth direction, and the lateral and elevational directions or a proper 2D orthogonal coordinate system involving the existence of two axes of a depth direction and the lateral direction can be permitted to be formed. Otherwise, an arbitrary coordinate system can also be permitted to be formed on the basis of an arbitrary axis. In the following explanation using expressions, the most basic Cartesian coordinate system of orthogonal coordinate systems is used. However, since the curvilinear orthogonal coordinate system can also be permitted to be used and then, the coordinate system is often used. The polar coordinate system with the largest curvilinear rate of those of all the curvilinear orthogonal coordinate systems is realized for the sector scanning or radial scanning using a catheter-type transducer for blood vessels etc. For the use of a catheter-type transducer, it is required that the radial direction corresponds to the depth direction, and the rotational direction corresponds to the lateral direction. Also for a convex-type transducer that realizes curvilinear orthogonal coordinate system with a small curvilinear rate, similarly the depth, lateral and elevational axes are properly set. Also for other transducers, on the basis of the physical aperture geometry, properly orthogonal coordinate systems are set. Also the ways for using other type coordinate systems are explained in detail in the paragraph [0033]. Ultrasounds can also be permitted to be transmitted in an arbitrary direction over a laterally wide ROI at the same time or at the same temporal phase, and the synthetic aperture (SA) processing can also be permitted to be performed.

One example of this conduct form, the ASTA beamforming (FIG. 5) or multidirectional beamforming (FIG. 7) on the basis of the ASTA beamforming (FIG. 7) is performed. On the multidirectional beamforming, as mentioned above, plural beams can be permitted to be transmitted and received at the same timing, or at other timing. The ASTA beamforming and the multidirectional beamforming can be permitted to include a non-steered beamforming (i.e., in a frontal direction with respect to a physical effective aperture). Other beams such as those of the harmonic echoes, those obtained for the use of contrast media and other useful beams etc. can also be permitted to be used. For such beamforming, high speed beamforming or synthetic aperture beamforming can also be permitted to be performed using ultrasound transmissions such as a plane wave or plane waves etc. in an arbitrary direction over a laterally wide region at the same time or at the same temporal phase etc.

As mentioned above, the beam steering can be permitted to be performed through the electronic beamforming (apodization, switching, delay processing, phase matching, summation etc.) itself, or through the slanting of the displacement/strain sensor 5 (the beams) by the mechanical scanning using the mechanical steering (FIG. 2 and FIG. 6). The electronic beamforming and mechanical scanning can also be permitted to be performed simultaneously. For such beamforming, high speed beamforming or synthetic aperture beamforming can also be permitted to be performed using ultrasound transmissions such as a plane wave or plane waves etc. in an arbitrary direction over a laterally wide region at the same time or at the same temporal phase etc. When performing the mechanical scanning, the steering angle ($\theta m$ shown in FIG. 6) generated by the mechanical scanning can be permitted to be detected using an arbitrary method or an arbitrary device, and correspondingly a coordinate system can be permitted to be set. A sensor for detecting the position or direction can also be permitted to be equipped with the displacement/strain sensor 5 and such sensor 5 can be permitted to be used. Otherwise, plural displacement/strain sensors can also be permitted to be used, and in such a case, a similar sensor can be permitted to be used.

Figure 8:
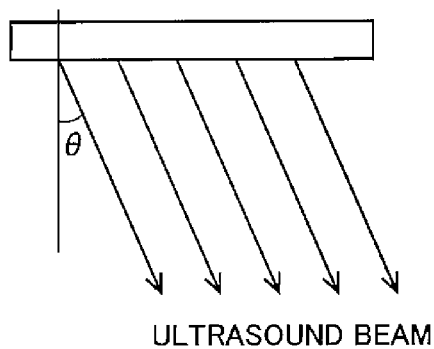
FIG. 8(a) shows illustration for explaining coordinate rotation of ultrasound echo data frame generated using steered beams.
FIG. 8(b) shows illustration for explaining the corresponding coordinate rotation in frequency domain.
Figure 8:
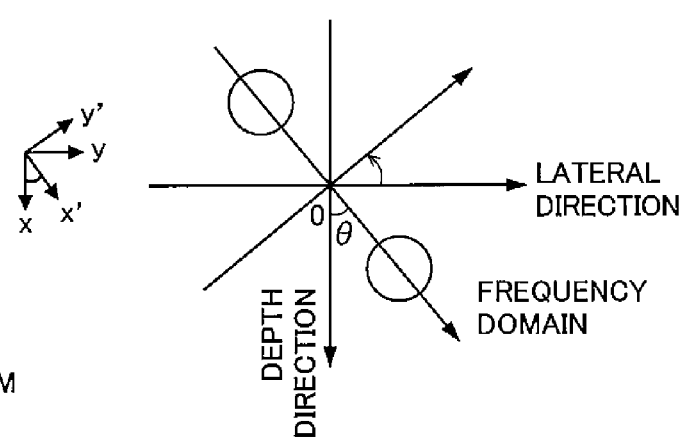

When generating the echo data frame or after generating the echo data frame, with respect to the object, a proper 3D orthogonal coordinate system involving the existence of three axes of a depth direction, and the lateral and elevational directions or a proper 2D orthogonal coordinate system involving the existence of two axes of a depth direction and the lateral direction can be permitted to be formed. Otherwise, an arbitrary coordinate system can also be permitted to be formed on the basis of an arbitrary different axis from the depth axis. In the following explanation using expressions, the most basic Cartesian coordinate system of orthogonal coordinate systems is used. However, since the curvilinear orthogonal coordinate system can also be permitted to be used and then, the coordinate system is often used. The polar coordinate system with the largest curvilinear rate of those of all the curvilinear orthogonal coordinate systems is realized for the sector scanning or radial scanning using a catheter-type transducer for blood vessels etc. For the use of a catheter-type transducer, it is required that the radial direction corresponds to the depth direction, and the rotational direction corresponds to the lateral direction. Also for a convex-type transducer that realizes curvilinear orthogonal coordinate system with a small curvilinear rate, similarly the depth, lateral and elevational axes are properly set. Also for other transducers, on the basis of the physical aperture geometry, properly orthogonal coordinate systems are set. Also the ways for using other type coordinate systems are explained in detail in the paragraph [0033]. Ultrasounds can also be permitted to be transmitted in an arbitrary direction over a laterally wide ROI at the same time or at the same temporal phase, and the synthetic aperture (SA) processing can also be permitted to be performed. In order to achieve the generation of an echo data frame, the rigid movement or coordinate rotation (FIG. 8) is required to be performed. Then, interpolation of echo data is required. In such a case, the phase rotation can be performed using a complex exponential in a frequency domain (patent document 1). Although the method yields no errors during the coordinate rotation if the Nyquist theorem is satisfied with, conventionally the calculation time is decreased by performing interpolation such as a linear interpolation etc. The interpolation can be performed in a space or in a frequency domain. However, because these calculations for the coordinate rotation can permit to realize non-real-time measurement, these methods should not be used if possible. High speed beamforming or synthetic aperture beamforming can also be permitted to be performed using ultrasound transmissions in an arbitrary direction over a laterally wide region at the same time or at the same temporal phase etc.

As shown in FIG. 6, when dealing with the object moves dominantly in a direction such as in a lateral direction etc., not the displacement vector measurement method but the one-directional displacement measurement method can be performed. In such a case, a single beam is used at least. The application of the one-directional displacement measurement is mainly performed for the conventionally difficult, high accuracy lateral displacement measurement. In contrast, the displacement vector measurement is useful, because the detection of a direction of dominant displacement is not required. For such a measurement, a single beam or plural beams are used.

For such a one-directional displacement measurement or a displacement vector measurement, in order to yield a high accuracy measurement of a displacement in a scanning direction, the carrier frequency in the scanning direction is set to a high frequency by increasing the steering angle (for instance, θ shown in FIG. 5 and FIG. 7) of steered beamforming achieved by the electric scanning or mechanical scanning. Such a high carrier frequency yields a high quality image and a high accuracy displacement measurement. High speed beamforming or synthetic aperture beamforming can also be permitted to be performed using ultrasound transmissions in an arbitrary direction over a laterally wide region at the same time or at the same temporal phase etc. However, if the electrically generated steering angle is made too large, a high echo SNR cannot be obtained. Then, if required, the combinational use of the electric and mechanical beam steering can also be permitted to be performed.

Figure 9:
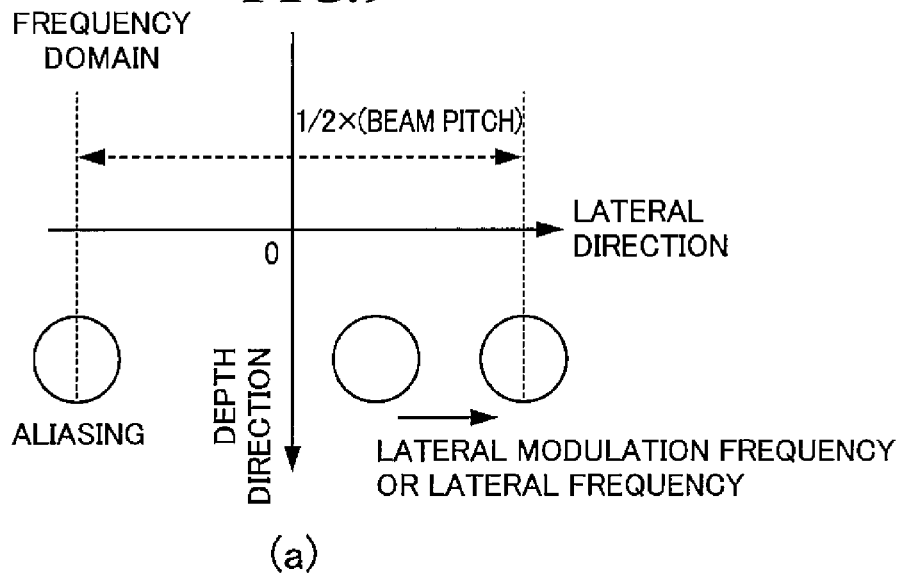
FIG. 9(a) shows illustration for explaining aliasing that occurs when failing in increasing lateral carrier frequency under coarse beam pitch by increasing steering angle (i.e., when Nyquist theorem is not satisfied with)
FIG. 9(b) shows illustration for explaining filtering out in frequency domain of side lobe or grating lobe generated by increasing steering angle.
FIG. 9(c) shows illustration for explaining method for increasing lateral bandwidth by padding zeros except for signal spectra in higher lateral frequency domain than lateral Nyquist frequency such that higher lateral carrier frequency than lateral Nyquist frequency can be achieved by increasing steering angle (i.e., interpolation of lateral sampling interval of coordinate system)
Figure 9:
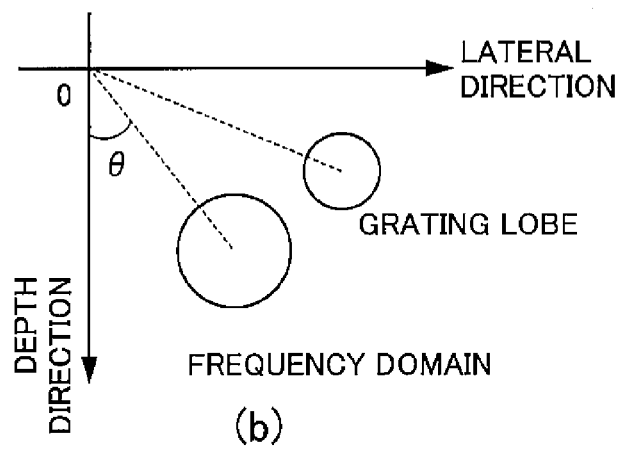
Figure 9:
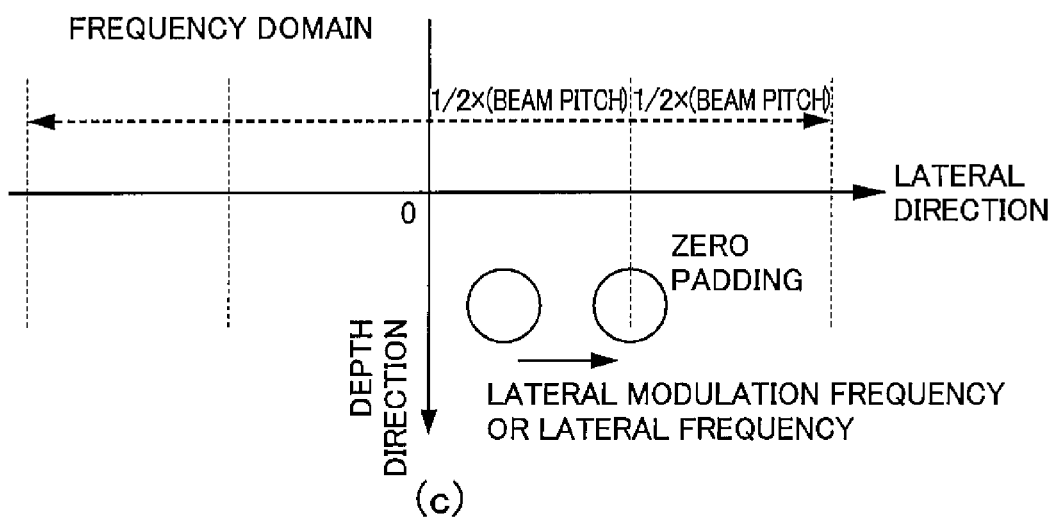

The carrier frequency of the scanning direction should be large. In accordance, the beam pitch should be small such that the aliasing phenomena [FIG. 9(a)] do not occur. That is, the highest frequency must become smaller than the half frequency determined by the beam pitch on the basis of the sampling theorem.

However, making the electric steering angle large grows the side lobes and grating lobes significantly. Thus, all the lobes are tried to be removed in a frequency domain by zero padding [FIG. 9(b)]. Alternatively, extracting spectra can permit to separate plural beams with different beam angles. Also the extracting spectra can permit to separate plural beams arrived from different directions. For instance, when plural beams are transmitted/received at the same timing for the multidirectional beamforming, the plural beams can be separated into those with different beam directions.

When it is possible to achieve a higher lateral carrier frequency than the highest frequency determined by the Nyquist theorem, padding zero spectra in higher frequencies than the Nyquist frequency permits an increase in a lateral bandwidth (i.e., interpolation of a lateral sampling interval of a coordinate system). Otherwise, in a spatial domain, the number of beams can be increased by spatial interpolation or beamforming can be performed with a dense beam pitch. Such processing is also effective when the present inventor's previously developed LM method (mentioned above) is applied to the present invention.

For the use of transducers, on the basis of the respective physical aperture geometries, properly orthogonal coordinate systems can be set (i.e., arbitrary orthogonal coordinate systems etc. set by the curvilinear rates of the respective transducers). Alternatively, including cases where a virtual source or a virtual receiver disclosed in the patent document 1 is used, although the limitation must be considered, an arbitrary directional and arbitrary shape beam or vision of field can be permitted to be generated through the delayed-and-summation processing and apodization processing regardless the aperture geometry of the transducer used. Accordingly, such beamforming can be permitted to be performed using an arbitrary orthogonal coordinate system. High speed beamforming or synthetic aperture beamforming can also be permitted to be performed using ultrasound transmissions in an arbitrary direction over a laterally wide region at the same time or at the same temporal phase etc.

When dealing with a spatial distribution as a measurement target, similarly these comprising elements generate the above-mentioned non-steered (frontal) beamforming (scanning), the above-mentioned multidirectional beamforming (scanning), the above-mentioned ASTA beamforming (scanning), the above-mentioned steered beamforming with a variable or invariant steering angle, the above-mentioned LM beamforming, the above-mentioned multidirectional beamforming and among others, and if required, the measurement target 6 is scanned laterally (i.e., in the direction orthogonal to the depth direction) with steered beams. The respective positions in the object 6 are not always scanned in a parallel condition. When performing beam steering, the beamforming can be permitted to be performed such that a large steering angle or a crossing angle can be obtained at the respective positions in the ROI. High speed beamforming or synthetic aperture beamforming can also be permitted to be performed using ultrasound transmissions in an arbitrary direction over a laterally wide region at the same time or at the same temporal phase etc. an echo data frame can also be permitted to be generated by the scanning and beamforming. These are similar below.

The data processing unit 1 can be permitted to perform echo imaging using US echo data frames obtained on the basis of the beamforming in a parallel manner or independently with respect to the displacement measurement. The data processing unit 1 implements the detection processing (quadrature detection, parabolic detection etc.) to the echo data obtained using the ASTA beams or multidirectional beams on an arbitrary orthogonal coordinate system. In such cases, echo data frames generated by coherent or incoherent superposition are converted into gray images (B-mode images comprising brightness data) or other images in other formats; measured data such as about displacements, velocities, strains etc. can also be permitted to be displayed solo or displayed by superposing the measured data on the echo images. Particularly, the displacement measurement can also be performed using the coherently superposed echo data (i.e., the coherent superposition method). The LM beamforming can be strictly interpreted as the superposition of plural crossed beams (non-patent document 21 disclosed by the present inventor), i.e., for 2D imaging and 2D displacement vector measurement, coherent superposition of two crossed beams; for 3D imaging and 3D displacement vector measurement, coherent superposition of three or four crossed beams. The generated beams can be permitted to be various as mentioned; and the timing of generations of plural beams can also be permitted to be various as mentioned above; and the timing of the superposition processing can also be permitted to be various. When using the multidimensional displacement vector measurement methods using complex analytic signals such as the multidimensional autocorrelation method, the multidimensional Doppler method etc., benefit features can be obtained. For instance, fewer calculations can be achieved by performing the Fourier's transform with respect to the echo data obtained after performing the superposition. Such LM beamforming (frequency) can also be permitted to be performed not only in the cases where the LM beamforming can be interpreted as the superposition of crossed beams (non-patent document 21) but also in the cases where such superposition of crossed beams is not used (i.e., above-mentioned other methods, for instance, non-patent document 8). Also in such a case, the displacement vector measurement method can be permitted to be used, and whenever the LM frequency is generated, the independent spectra and the corresponding crossed beams can be separated through the Fourier's transform (for instance, patent document 1; non-patent document 13). For instance, when spectra of the plural beams are overlapped in the frequency domain, the spectra frequency division method or stochastic evaluation etc. can also be permitted to be used to separate signals or beams; and when spectra overlap due to the occurrence of aliasing when making steering angles large, the stochastic evaluation etc. can also be permitted to be used to separate signals or beams. In this way, with respect to arbitrary waves (mechanical wave, electromagnetic wave, thermal wave etc.), when simultaneous transmissions of plural waves and corresponding reception of waves, or observing signals arrived from arbitrary directions is performed, the signals can be separated. Also global propagation direction or the distribution of the propagation directions with a spatial resolution can also be measured. Using the present invention, for instance, the separation of echo signals corresponding to plural differently directional beams can be performed with respect to echo signals generated through the superposition of beams; and shear waves propagating in the respective directions or arrived from the respective directions can also be measured globally or with a high spatial resolution from a measured, superposed shear wave distribution. Using the temporal series measured, as mentioned above, the shear wave propagation speed can also be measured with a high accuracy. It is also effective to use the reversibility of the Fourier's transform. In the present inventions, specific evaluation can also be performed on the separated beams or signals (for instance, crossing or focus position of crossed beams and many others.).

The coherent superposition can also permit to generate (synthesize) new beam properties. In such a case, new spatially continuous spectra such as single quadrant or single octant spectra, or 1D spectra can be generated to yield new plural beams. The frequencies and bandwidths in respective directions can be controlled. At least, the increase in a bandwidth can be achieved and then the increase in a spatial resolution can be obtained. For the superposition, proper combination of the following ultrasounds can be permitted to be used, i.e., plural steered beams with different steering angles (i.e., with different lateral frequencies including that of zero steering angles), ultrasounds with different US frequencies, ultrasounds with different depth or lateral bandwidths, ultrasounds with other different US parameters such as a F-number etc., a basic or 2nd order harmonic wave etc. The superposition can be permitted to be performed on respectively weighted echo data, i.e., with the same global echo data energy or with the same local echo data energy or power.

As mentioned above, the obtained coherent signals can be permitted to be detected and then used for echo imaging; otherwise, the respective signals can be permitted to be detected and then superposed.

(1) When a 1D, 2D or 3D complex analytic signal is expressed by $r+ji$ (r, real signal; I, imaginary signal; j, imaginary unit), the corresponding envelop-detected signal is calculated as $r^2+i^2$ or $\sqrt{(r^2+i^2)}$; or (2) when a 1D, 2D or 3D detected signals expressed by $a+jb$ (a, real signal; b, imaginary signal) is obtained by performing the inverse Fourier's transform on the following spectra after shifting the spectra to the direct current (DC) on the basis of the 1st spectral moments of the spectra or instantaneous frequencies, i.e., the spectra obtained by Fourier's transform of a 1D, 2D or 3D complex analytic signal or the corresponding real signal (or the corresponding imaginary signal, i.e., the signal with 90 degrees difference from the real signal), or the spectra obtained before calculating a 1D, 2D or 3D complex analytic signal using the inverse Fourier's transform, the corresponding envelop-detected signal is calculated as $a^2+b^2$ or $\sqrt{(a^2+b^2)}$; (3) with respect to the 1D, 2D or 3D complex analytic signal obtained by the inverse Fourier's transform of the spectra described in (2), the multiplication of a 1D, 2D or 3D complex analytic signal obtained by the inverse Fourier's transform of the spectra symmetric with respect to the origin (DC) is performed, or the root of the multiplication is calculated. The envelop detection can also be permitted to be performed in other manners (see patent documents 6 and 7 disclosed by the present inventor including the quadrature detection). These 1D, 2D or 3D complex analytic signals are ones corresponding to target spectra (i.e., to be dealt with) such as divided spectra (i.e., spectra frequency division) and the corresponding complex analytic signals (or the real or imaginary signals), superposed spectra and the corresponding complex analytic signals (or the real or imaginary signals), raw spectra (i.e., not any processed) and the corresponding complex analytic signals (or real or imaginary signals) etc. The superposition processing of coherent signals is performed on a 1D, 2D or 3D complex analytic signal, or the real or imaginary signals in spatial and temporal spaces or in a frequency domain. The real signals include raw 1D, 2D or 3D rf-signals.

The parabolic detection signals are obtained by calculating parabolic powers with respect to the real or imaginary signals of 1D, 2D or 3D complex analytic signals or by calculating the root of the powers. The real or imaginary signals of the 1D, 2D or 3D complex analytic signals are ones corresponding to target spectra (i.e., to be dealt with) such as divided spectra (i.e., spectra frequency division), superposed spectra, raw spectra (i.e., not any processed) etc. The superposition processing of coherent signals is performed on a 1D, 2D or 3D complex analytic signal, or the real or imaginary signals in spatial and temporal spaces or in a frequency domain. The real signals include raw 1D, 2D or 3D rf-signals. Instead of the parabolic detection, power detection using the higher order than 2nd order can also be permitted to be performed. Also in such cases, these signal processing can also be permitted to be performed similarly to the parabolic detection.

The superposition of coherent signals can be permitted to be performed with respect to the complex signals or real signals. The superposition of incoherent signals obtained through the detection as mentioned above etc. such as the dimension of echo signals, power of echo signals with 2nd order or with other higher orders, or log-compressed echo signals. For the coherent or incoherent superposition, echo signals with different dimensions can also be permitted to be used.

The superposition of incoherent signals has an effectiveness to reduce speckles. However, when performing the parabolic detection, if the number of the waves to be superposed is small, the oscillations of echo signals can be clearly confirmed and then, the incoherent superposition can also be permitted to be used for the imaging of oscillations. The imaging of the superposition of coherent signals is useful for confirming the oscillations of echo signals.

Using the spectra frequency division method, similarly the imaging can also be permitted to be performed, i.e., such coherent or incoherent superposition obtained on the multidimensional complex analytic signals or echo data calculated form the multidimensional spectra divided in the frequency domain can be displayed similarly. The incoherent superposition has effectiveness for the speckle reduction in an echo image. The echo data superposition can also be permitted to be performed on the weighted echo data. For instance, with respect to the respective echo data, i.e., the same global echo data energy or the same local echo data energy or power is generated. Particularly, the coherently superposed signals are used to generate new spectra for tissue displacement measurement. Various superposition can be permitted to be performed using various combinations of the following spectra, i.e., raw spectra obtained before being divided (i.e., no processed spectra), spectra obtained after being divided (for instance, as mentioned below, the spectra divided in the following directions, i.e., the vertical or horizontal direction, the beam direction, the direction orthogonal to the beam direction etc. or the spectra divided in plural different manners with respect to same spectra etc), new spectra obtained after being superposed (various combinations of spectra, for instance, combination of raw spectra, combination of raw spectra and divided spectra etc.) spectra obtained after being divided in different manners with respect to same spectra such obtained (for instance, as mentioned below, the spectra divided in the following directions, i.e., the vertical or horizontal direction, the beam direction, the direction orthogonal to the beam direction etc. or the spectra divided in plural different manners etc.). The spectra division can be permitted to be performed using a straight line or plane, or a curved line or plane.

Regarding the coherent superposition method of spectra, otherwise, on the basis of the evaluation of distribution of spectral SNRs (a central part of beam has a high SNR.), the positions or directions of superposition to be performed, the shapes of spectra to be used, the weighting, the bandwidths and the 1st spectral moments (instantaneous frequencies) obtained by the superposition can be permitted to be determined. For instance, the spectra, the 1st spectral moments (instantaneous frequencies) and shapes of the bandwidths etc. can be permitted to be controlled with the consideration about the SNRs such that the spectral SNRs to be obtained by the superposition becomes almost constants within the bandwidths; or spectra within high SNR bandwidths are amplified and those within other bandwidths are attenuated or filtered out; or the frequencies become as high as possible in order to achieve high accuracy measurement; or the spectral SNRs within low frequency bandwidths become high properly etc. Alternatively, the positions or directions of superposition to be performed, the shapes of spectra to be used, the weighting, the bandwidths and the 1st spectral moments (instantaneous frequencies) obtained by the superposition can be permitted to be determined by evaluating the 1st moments of spectra to be obtained; the independency of vectors comprising the matrix of system of equations (i.e., determined by the instantaneous frequencies of analytic signals obtained using the inverse Fourier' s transform) used by the multidimensional autocorrelation method or multidimensional Doppler method. They can also be permitted to be determined with the consideration about a spatial resolution, i.e., related to bandwidths of spectra and their shapes to be superposed (the spatial resolution increases by increasing the bandwidths.). The weighting processing corresponds to such superposition of spectra; processing using windows (amplified or attenuated, etc.); extracting etc. Such weighted spectra can be superposed. Such weighting or windows can also be permitted to be implemented after performing the superposition of spectra or signals.

Regarding the spectra frequency division method of spectra, otherwise, on the basis of the evaluation of an SNR distribution of spectra (a central part of beam has a high SNR.), the positions or directions of division to be performed, the shapes of spectra to be used, the weighting, the bandwidths and the 1st spectral moments (instantaneous frequencies) obtained by the division can be permitted to be determined. For instance, the spectra frequency division can be performed such that the SNRs of spectra to be obtained by the division become almost constants within the bandwidths; or spectra within high SNR bandwidths are amplified and those within other bandwidths are attenuated or filtered out; or the frequencies become as high as possible in order to achieve high accuracy measurement; or the SNRs of low frequency bandwidths become high properly etc. Alternatively, the positions or directions of division to be performed, the shapes of spectra to be used, the weighting, the bandwidths and the 1st spectral moments (instantaneous frequencies) obtained by the division can be permitted to be determined by evaluating the 1st moments of spectra to be obtained; the independency of vectors comprising the matrix of system of equations (i.e., determined by the instantaneous frequencies of analytic signals obtained using the inverse Fourier's transform) used by the multidimensional autocorrelation method or multidimensional Doppler method. They can also be permitted to be determined with the consideration about the spatial resolution, i.e., related to bandwidths of spectra and their shapes to be obtained by the division (the spatial resolution decreases.). The weighting processing corresponds to such division of spectra; processing using windows (amplified or attenuated, etc.); extracting etc.

For these coherent superposition and spectra frequency division, proper positions, directions, shapes, weighting, and bandwidths (including shapes) and spectral moments (instantaneous frequencies) depend on the direction of a target displacement and specifications about the transducer to be used as well as beamforming parameters and beams generated or to be generated (including beams generated such that the steering angle becomes 0 degrees.), and the superposition and division processing can also be permitted to be performed using databases on the proper positions, directions, shapes, weighting obtained from the results of analyses, simulations and experimental evaluations obtained with respect to samples in advance, or databases on the bandwidths and frequencies etc. obtained after performing the processing. In the present invention, there is a case where spectra (signals) obtained by the spectra frequency division can be permitted not to be used [for instance for non-steered beamforming (frontal beamforming), as mentioned below, lateral low frequency spectra with high SNRs are disregarded and in contrary, lateral high frequency spectra are regarded etc.]. Such using only spectra within particular bandwidths also corresponds to the extracting of spectra.

On the performing the superposition, division or extracting of spectra, by implementing a window (i.e., frequency response of a filter) to the spectra, the processing of weighting can be permitted to be performed as mentioned above. The estimate of a distribution of SNRs is used basically as mentioned above. When the weighting is performed by implementing a window with a spatially bias (frequency response of a filter), the window is not spatially symmetric (for instance, when amplifying or attenuating a high frequency spectra, etc.). The shape of bandwidth determined by such a window used or the spectra (magnitudes, bandwidths and shapes) obtained by the superposition and division can be permitted to be considered. The proper windows for such processing depend on the direction of a target displacement and specifications about the transducer to be used as well as beamforming parameters and beams generated or to be generated (including beams generated such that the steering angle becomes 0 degrees.), and the superposition and division processing can also be permitted to be performed using databases on the proper positions, directions, shapes, weighting obtained from the results of analyses, simulations and experimental evaluations obtained with respect to samples in advance, or databases on the bandwidths and frequencies etc. obtained after performing the processing.

For echo imaging, the shape of a beam or a speckle (sound pressure) is required to be considered. These depend on the beamforming parameters (a direction of a single aperture or an arrayed-type, physical aperture of a transducer, and for such an arrayed-type transducer, delays or aperture directions set on respective vibrators (elements), an aperture width, an F-number, an apodization, a pulse shape, a pulse sequence (series) and a wavenumber etc.), the transducer parameters (geometries and widths of arrayed elements, element pitches, element materials etc.) used for generating beams, parameters for the superposition processing (positions and directions of the superposition, and shapes, weighting, bandwidths (spectra and shapes) or the 1st spectral moments (instantaneous frequencies) of spectra to be obtained by the superposition etc.), parameters for the division processing (positions and directions of the division, and shapes, weighting, bandwidths (spectra and shapes) or the 1st spectral moments (instantaneous frequencies) of spectra to be obtained by the division etc.), windows to be used (frequency response such as cutoff frequencies and shapes of bandwidths etc.) etc. It is desirable that the beamforming parameters and transducer parameters for generating beams, and the parameters for the superposition and division required after generating the beams are properly designed in a combinational manner. As mentioned above, for the design, simulations and experiments are effective. Also the design is permitted to be performed using the optimization method mentioned above. For instance, through the setting a desirable point spread function (PSF) as a target, the optimization should be performed with respect to the US frequency, LM frequency, shape of envelop, bandwidths in the respective directions, wavenumbers etc.). The PSF desirable for echo signals (beams obtained as the results of the superposition processing or spectra frequency division processing) is basically selected by using the image quality quantitatively evaluated using the present invention or visually confirmed, the SNRs of echo signals to be generated, the contrast to be generated, the energies to be generated etc. as measures. When using the PSF for the displacement measurement as well, the measurement accuracy etc. can also be used as a measure (when performing only the displacement measurement, the evaluation of the image quality is not required.). The experimental data or simulation data can also be used as constraints for the above-mentioned optimization. As mentioned above, the optimization can also be performed directly using the echo SNR, measurement accuracy, contrast, image quality quantitatively evaluated using the present invention or visually confirmed, etc. The optimization can also be used for other beamforming, and with the coherent superposition processing and division processing or with no such processing.

The designs for the echo imaging and displacement measurement mentioned above can be permitted to be performed respectively or in a combinational manner by using same measures that are set under a proper control. Otherwise, the design can also be permitted to be performed such that both the original measures are satisfied with simultaneously. Thus, the same beamforming can be permitted to be performed for both purposes. These designs can also be permitted to be performed with trial and error. The respective PSFs required for the optimization mentioned above can be permitted to be ones properly set for the respective purposes, or in a combinational manner by using the same PSF that is set under a proper control. Otherwise, a PSF can also be permitted to be set by the optimization such that both the original measures for the purposes are satisfied with simultaneously. Thus, the same beamforming can be permitted to be performed for both purposes.

As mentioned above, the displacement measurement methods (i.e., methods for measuring the multidimensional displacement vector or one-directional displacement) use the phase of US echo signals acquired at more than two temporal phases as a measure. The echo signal used for generating an echo image can be permitted to be different from those used for measuring displacement etc.

The data processing unit 1 can permit to implement a spatial differential filter or a temporal differential filter to the measured displacement (vector components, distributions, temporal series) in order to calculate strain (tensor components, distributions, temporal series), strain rate (tensor components, distributions, temporal series), acceleration (vector components, distributions, temporal series), velocity (vector components, distributions, temporal series), instantaneous phase change, shear wave propagation speed or propagation speed (distributions, temporal series), shear wave vibration displacement (or vibration velocity or vibration acceleration) or shear wave amplitude, shear wave vibration frequency, shear wave vibration direction, shear wave phase (distributions, temporal series)

For these measurements, a basic wave component and harmonic wave components of US echo signal acquired for the 3D ROI, 2D ROI or 1D ROI primarily in the lateral direction. The harmonic wave components can permit to increase accuracy in axial displacement measurement due to having a high carrier frequency; and can also permit to increase accuracy in lateral displacement measurement due to having a larger lateral bandwidth (a laterally sharper beam) than the basic wave component. Because the harmonic wave components have small SNRs, all wave components can also be permitted to be used effectively. That is, echo imaging can be permitted to be performed using received echo signal, only the extracted basic wave (n=1), only the extracted n-th harmonic waves (n=2 to N) or the combination of these signals. As mentioned below, the measurements of a displacement vector and a one-directional displacement primarily in the lateral direction can also be permitted to be performed as mentioned below.

As explained above, apparatus for imaging and displacement measurement related to the present conduct form can permit to measure the displacement (vector components, distributions, temporal series), strain (tensor components, distributions, temporal series), strain rate (tensor components, distributions, temporal series), acceleration (vector components, distributions, temporal series), velocity (vector components, distributions, temporal series), instantaneous phase change, shear wave propagation speed or propagation speed (distributions, temporal series), shear wave vibration displacement (or vibration velocity or vibration acceleration) or shear wave amplitude, shear wave vibration frequency, shear wave vibration direction, shear wave phase (distributions, temporal series) etc. generated in the 3D or 2D ROI from US echo data frames measured over the 3D or 2D space. Echo imaging can also be permitted to be performed. In addition, occasionally, for instance, the echo imaging in the beam direction or the lateral direction etc. and measurement of a tissue displacement or displacement vector in an arbitrary direction can also be permitted to be performed.

This apparatus is comprising, the displacement/strain sensor 5 (the ultrasound transducer); mechanical control unit 4 of relative position with respect to the object 6, and vertical, horizontal, turn and fan-directional movements; the driving/output control unit 5' for generating driving signals to drive the displacement/strain sensor 5 as the transmitter or the ultrasound pulser, and for processing echo signals output from the displacement/strain sensor 5 as the receiver and the amplifier; the driving/output control unit 5' or the data processing unit 1 for performing prescribed beam steering (focusing processing such as the transmission-fixed focusing/reception dynamic focusing, multiple transmission-fixed focusing/reception dynamic focusing; high speed beamforming, i.e., transmission of one or plural laterally wide waves are performed in arbitrary directions at the same time or at the same temporal phase); apodization processing (processing for improving a US beam: weighting processing on US signals transmitted from the respective vibrators (elements) in order to sharpen the beam shape); the data storage 2 for storing the output of the displacement/strain sensor. For the synthetic aperture processing, the data storage 2 and the data processing unit 1 work mainly after the A/D conversion.

A data processing unit 1 works for measuring the displacement vector components (distributions, time series), one-directional displacement (distribution, time series), strain tensor components (distributions, time series), strain rate tensor components (distributions, series), acceleration vector components (distributions, series), velocity vector components (distributions, series), etc., whereas the data storage 2 also stores the calculated results. For echo data acquisition, a mechanical scan can be combined with the electric steering.

In this case, the data processing unit 1 has a feature for calculating a strain (tensor, distribution, temporal series) by implementing a spatial differential filter (a 3D, 2D or 1D spatial filter) with a limited bandwidth or a frequency response of the spatial differential filter with the limited bandwidth (3D, 2D or 1D frequency response) to the 3D or 2D displacement vector (distribution, temporal series) in the 3D ROI, the 2D displacement vector in the 2D ROI, the one-directional displacement component in the 3D, 2D or 1D ROI measured through the US data acquisition and signal processing.

The data processing unit 1 can also permit to calculate the strain rate (tensor, distribution, temporal series), acceleration (vector, distribution, temporal series) or velocity (vector, distribution, temporal series) by implementing a temporal differential filter with a limited bandwidth or a frequency response of the temporal differential filter with the limited bandwidth to these temporal series.

In order to generate at least more than a strain tensor field (a displacement vector field) in the 3D, 2D or 1D ROI in the object, a compressor or a vibrator, a radiation force can be permitted to be used as a mechanical source. Alternatively, the object 6 (tissue) motion (heartbeat, blood pulsation, respiratory etc.) can be permitted to be used as a mechanical source; and the strain (tensor field) or displacement (vector field) generated in the 3D, 2D or 1D ROI in a synchronized manner with respect the object motion can be permitted to be measured.

Moreover, via an inverse problem analysis, mechanical properties, stress tensor components, pressure or mechanical source etc. can be permitted to be calculated using these motion data or deformation data. As mentioned above, the propagation speed or propagation direction of the shear wave and further the shear modulus distribution can also be permitted to be measured (note that, however, the spatial resolution becomes lower than that obtained by the inverse analysis due to the long wavelength of a shear wave). Other physical properties (such as a density, a bulk modulus and visco-elastic constants) required for the calculation are set to the measured data or typical values. Approximately, a density can also be permitted to be used. Otherwise, the density can also be permitted to be assumed to be a constant.

The types of a US transducer can be permitted to be various as mentioned below. That is, as a displacement/strain sensor, a mechanical scan-type US vibrator, an electronic scan-type 2D US element array (being mechanical scanning possible), or an electronic scan-type 1D US array (being mechanical scanning possible) etc. are used; and prescribed beam steering is realized and echo signals are acquired. Ultrasounds can also be permitted to be transmitted in an arbitrary direction over a laterally wide ROI at the same time or at the same temporal phase, and the synthetic aperture (SA) processing can also be permitted to be performed. In the following explanation using expressions, the most basic Cartesian coordinate system of orthogonal coordinate systems is used. However, since the curvilinear orthogonal coordinate system can also be permitted to be used and then, the coordinate system is often used. The polar coordinate system with the largest curvilinear rate of those of all the curvilinear orthogonal coordinate systems is realized for the sector scanning or radial scanning using a catheter-type transducer for blood vessels etc. For the use of a catheter-type transducer, it is required that the radial direction corresponds to the depth direction, and the rotational direction corresponds to the lateral direction. Also for a convex-type transducer that realizes a curvilinear orthogonal coordinate system with a small curvilinear rate, similarly the depth, lateral and elevational axes are properly set. Also for other transducers, on the basis of the physical aperture geometry, properly orthogonal coordinate systems are set. Also the ways for using other type coordinate systems are explained in detail in the paragraph [0033].

When using these displacement/strain sensors in order to acquire echo signals, if the sensors can be contacted onto the object, the contact surface of the sensor can be a mechanical source such as a compressor or a vibrator. Moreover, for the high intensity US treatment, when the target tissues and the sensor are dipped in or immersed in a proper liquid, a non-contact measurement can also be achieved. As mechanical sources, in addition to such a compressor or a vibrator (a transducer body can permit to work as the compressor or vibrator), other mechanical sources such a high intensity US or a radiation force (a transducer can permit to work as the applicator and in such a case, the transducer can also be permitted to receive the correspondingly generated echo signals) etc. or uncontrollable mechanical sources in the object (for observing tissues, for instance, heartbeat, respiratory, blood pulsation, body motion etc.; lung, air, blood vessels, blood etc. can be permitted to be included in the ROI) can be used. The high intensity US or the radiation force can be permitted to be used in order to achieve both effects simultaneously. Otherwise, the control of the driving energy or shape of radiated signals can be permitted to exchange the effects each other. Echo signals obtained with respect to the high intensity US treatment or the force radiating can be permitted to be used for the simultaneous echo imaging or measuring the tissue displacements generated with respect to the high intensity US treatment or the force radiating.

In order to measure the distributions of elastic or visco-elastic constants, when the displacement/strain sensor (US transducer) is used as a contact-type compressor (a mechanical source), a reference material for measuring the elastic or visco-elastic constants can be permitted to be put between the sensor and object. Such a reference material can be fixed with or installed into the sensor (i.e., one body comprising the sensor and reference material.).

Basically, the 3D or 2D displacement vector (distribution, temporal series) in the 3D ROI, 2D displacement vector in the 2D ROI (distribution, temporal series), or one-directional displacement primarily in the lateral direction (or in the axial direction) in the 3D, 2D or 1D ROI is measured via prescribed data processing (signal processing) from US echo signals acquired in the 3D, 2D or 1D ROI via prescribed beam-steering using the displacement/strain sensor as mentioned above. Form the measured displacement data, calculated can be a strain (tensor, distribution, temporal series), a strain rate (tensor, distribution, temporal series), an acceleration (vector, distribution, temporal series), a velocity (vector, distribution, temporal series), an instantaneous phase change (distribution, temporal series), a shear wave propagation speed or direction (distribution, temporal series), a shear wave vibration displacement (or vibration velocity or vibration acceleration), a vibration amplitude, a vibration frequency, a vibration direction, a phase (distribution, temporal series).

The displacement measurement methods and echo imaging methods used in the data processing unit 1 are specifically explained below.

On the basis of the widely known Fourier's transform or Hilbert's transform etc. (for instance, non-patent document 3), single quadrant spectra [FIG. 5($c$)] and single octant spectra [FIG. 5($d$)] are respectively obtained from echo data expressed in the 2D and 3D ROIs. The angles 8 shown in the figures respectively equal to the steering angles [FIG. 5($a$) and FIG. 5($b$)] obtained when performing beam-steering with a steering angle (i.e., ASTA). For instance, the figures can also be applied to non-steered (frontal) beamforming with respect to the aperture ($\theta=0°$). In the respective figures in a frequency domain, there exist two single quadrant spectra and two single octant spectra, specifically the same spectra with symmetrical positions with respect to zero (a direct current). The inverse Fourier's transforms of the respective single quadrant or octant spectra yield 2D and 3D analytic signals, respectively (non-patent document 3).

Figure 7:
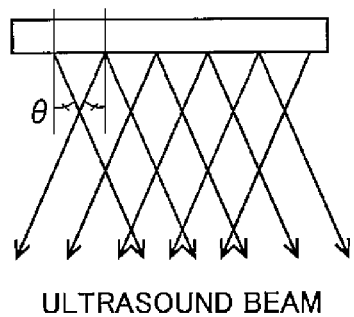
FIG. 7 shows for lateral modulation performed for 2-dimensional region of interest, crossing of steered beams [FIG. 7(a)] and the corresponding spectra [FIG. 7(b)]
Figure 7:
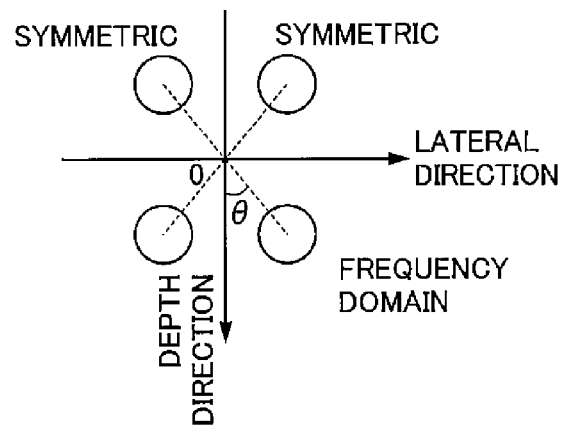

When performing the LM beamforming (non-patent document 3, 6, 7 etc.) or multidirectional beamforming, for instance, when dealing with the 2D ROI, spectra schematically shown in FIG. 7($b$) are obtained with respect to the performing of the beamforming schematically shown in FIG. 7($a$), of which two single quadrant spectra are independent. Further generation of the beam-steering with another steering angle yields more than three independent quadrant spectra.

When dealing with the 3D ROI, more than three independent single octant spectra [one single octant spectra schematically shown in FIG. 5($d$)] are obtained with respect to the using more than three different steering angles (non-patent document 3).

The above-mentioned coordinate rotation (FIG. 8) can permit to control the instantaneous frequency in the axial direction or the 1st spectral moment (patent document 1). In this case, the generated plural beams can be permitted to be symmetric or non-symmetric with respect to the axis in the frontal direction of the coordinate system. The plural beams can be permitted to include the non-steered (frontal) beam ($\theta=0°$). Plural transducers can also be permitted to be used simultaneously. The echo data movement such as the coordinate rotation etc. is implemented on large echo data such as those of a frame, or for a local displacement measurement (i.e., measurement of the displacement of a local region), rather small data of a searching region including the local region are processed.

(I) Beam-Directional Displacement Measurement or One-Directional Displacement Measurement First of all, the present invention permits a displacement measurement on the basis of the ASTA beamforming method, the non-steered (frontal) beamforming method, the beam steering method with a variable or invariable steering angle, the LM beamforming method, the multidirectional beamforming method or other beamforming methods, high accuracy measurement of a displacement component, a velocity component or a strain tensor component in a beam direction by considering the directivities of US vibrators (elements), directions of scattering and reflection, attenuation and their frequency modulations due to the physical phenomena, i.e., by calculating an actually generated beam direction at each position of interest with a high accuracy from echo data generated. On the below-disclosed methods (3) and (4), for the echo signals, divided spectra are used (for instance, vertical division, horizontal division, division in the beam direction or in the direction orthogonal to the beam direction etc., division using several different manners with respect same spectra etc.). For the methods (1) to (4) disclosed below, the following spectra can be permitted to be used, i.e., originally such divided spectra; non-divided (non-processed) spectra; newly synthesized spectra by superposition (i.e., a synthesized beam), signals obtained through division using plural different manners with respect to same spectra such obtained (for instance, vertical division, horizontal division, division in the beam direction or in the direction orthogonal to the beam direction etc.); superpositions with various combinations of such obtained spectra. For such measurements, an arbitrary orthogonal coordinate system is used. As mentioned above, echo data can be permitted to be obtained through synthetic aperture (SA) processing. For measurement and imaging of results, in order to obtain data to be displayed of the respective pixels, the measurement results can be permitted to be interpolated. Otherwise, displaying can be permitted to be performed according to the coordinate system of the performed measurements (i.e., the coordinate system can be permitted to be used for the display). The interpolation methods can be permitted to be above-mentioned proper ones etc.

The beam direction used in the present invention can be obtained with respect to each position of interest (x,y) expressed using the Cartesian coordinate system by calculating the 1st spectral moments of local spectra obtained for local echo data centered on the position (x,y), or by calculating instantaneous frequencies in the respective directions through multidimensional moving averaging on the basis of the multidimensional autocorrelation method or the multidimensional Doppler method (non-patent document 3). For instance, when performing 2D displacement vector measurement using 2D echo data frames, if a frequency vector is expressed as (fx, fy), the angle α in the beam direction at the position of interest is expressed by $\alpha = \tan^{-1}(fy/fx)$ in FIG. 10.

In this way, the beam direction actually generated can be calculated with a high spatial resolution through a 2D spectral analysis. Otherwise, although a spatial resolution decreases, the beam direction can also be calculated with respect to echo data of a finite region or space such as all echo data of an ROI, i.e., a global beam direction can also be calculated through the calculation of the 1st spectral moments of global spectra to be obtained. Even such a globally calculated beam angle is different from the beam angle designed (conventional one) using delays set on the respective arrayed US vibrators (elements), and due to the above-mentioned reason, the measurement accuracy increases.

With respect to arbitrary waves (mechanical waves, electromagnetic waves, thermal waves etc.), the similar analysis can also permit to measure the propagation direction (distribution). A spatial resolution can also be obtained by performing the analysis locally; and global analysis can also yield a global data. This is similarly applied to a shear wave.

The evaluation of spectra also permits to estimate bandwidths; and the inverses of the bandwidths in the beam direction and in the direction orthogonal to the beam direction permits to estimate a pulse length and a beam width. As mentioned above, being dependent on an effective aperture size apodization, a beam magnitude changes, for instance, a speckle shape and the speckle shape distribution changes. Bing dependent on a steering angle, a proper apodization function changes. For instance, the apodization function can be permitted to be determined using the optimization method disclosed in non-patent documents 10 and 11 etc. This is similarly applied to other applications as well as the echo imaging. Thus, by displaying the beam direction distribution using a vector line map, for instance, a boundary position can be detected by detecting reflection and refraction in an object; and a reflectivity, a refractivity or the ratio of an ultrasound speed can be calculated. Otherwise, by calculating spatial distributions of their bandwidths or the inverses and by displaying them in a gray scale or in a color scale etc., for instance, the position with a large lateral bandwidth (with a narrow beam width) can be detected; and then the position of focus or the direction to the focus position can be detected. That is, a sound pressure shape distribution or a beam shape etc. can be measured with a high accuracy and with a high spatial resolution. When performing the analysis with respect to the global spectra, for instance, a focus position, a direction to the focus position, a sound pressure shape distribution, a beam shape etc. as well as the above-mentioned beam direction can be detected globally. When generating newly spectra using the coherent superposition method, such evaluation is effective for the evaluation, design or optimization of the respective coherent signals to be superposed as well as the generated signals. Also for the spectra frequency division method, such evaluation can be used for the evaluation, design or optimization of divided spectra to be obtained.

Below, although the description is mainly performed about the displacement measurement, also for the purpose of echo imaging, the evaluation can be used for the design of beamforming parameters and transducer parameters; and also for realizing a desirable point spread function (PSF), the above-mentioned optimization methods (the steepest gradient method, the Newton-Raphson method, the linear programming method, the non-linear programing method, the dynamic programming method, the constrained optimization method etc.) can be performed on the beamforming parameters and transducer parameters using measured spectral data or databases (the database can be permitted to be made and used.) obtained with respect to the changes in beamforming parameters and transducer parameters. For instance, parameters etc. can be determined for high spatial resolution echo imaging. The present inventor previously clarified that for displacement measurement, the PSF envelop should have the shape of a function with short feet such as power functions rather than that of a function with long feet such as the Gaussian function to yield a high measurement accuracy; and then the optimization can be performed with respect to the apodization function to realize such a desirable PSF. Although it is possible to measure a sound pressure distribution in water using a hydrophone, for a practical object, the sound pressure distribution generated under the respective parameters can be obtained by performing the same local spectral analysis or by locally calculating autocorrelation functions that is equivalent to the corresponding local spectra. In this case, because the inhomogeneity of acoustical properties of a target tissue can be dealt with, the best echo imaging and the best tissue displacement measurement can be realized. For instance, on the evaluation about the apodization, the inhomogeneity of ultrasound speed in a tissue can be dealt with (patent document 3). Related to this, when performing the LM beamforming or multidirectional beamforming, the control of the crossing position of crossed beams or the focus positions of the respective beams can be permitted to be performed. Basically, as mentioned in advance, the PSF for displacement measurement is designed or optimized using an echo SNR, a measurement accuracy and a measurement error etc. as measures, whereas the PDF for echo imaging is designed or optimized using an echo SNR, a contrast, an image quality quantitatively evaluated using the present invention or visually confirmed, etc. as measures. The optimization can also be performed directly using the echo SNR, measurement accuracy, measurement error, contrast, image quality quantitatively evaluated using the present invention or visually confirmed, etc.

As mentioned above, for echo imaging, the beam shape and speckle reduction (sound pressure), is required to be considered. The beam shape and speckle reduction depend on the beamforming parameters (a direction of an aperture of a single aperture or arrayed-type transducer; for such an arrayed-type transducer, delays set on the respective US elements or the respective directions of the apertures of US elements; an aperture width; an F-number; an apodization; a pulse shape; a pulse sequence (series), wavenumber etc.) and the transducer parameters (geometries and widths of arrayed elements, element pitches, element materials etc.). When performing the coherent superposition and spectra frequency division, the respective parameters are as follows, (1) parameters for the coherent superposition: a position, a direction, a shape or weighting for the coherent superposition, a bandwidth (spectra and shape etc.) or the 1st spectral moments (instantaneous frequencies) to be obtained by the superposition, etc.

(2) parameters for the spectra frequency division: a position, a direction, a shape or weighting for the spectra frequency division, a bandwidth (spectra and shape etc.) or the 1st spectral moments (instantaneous frequencies) to be obtained, windows (of which frequency response should be designed including a cutoff frequency or a bandwidth shape etc.) to be used, etc.

Concretely, it is desirable that the beamforming parameters and transducer parameters for generating beams, and the parameters for the superposition and division required after generating the beams are properly designed in a combinational manner. As mentioned above, for the design, simulations and experiments are effective (the database can be permitted to be made and used.). Also the design is permitted to be performed using the optimization method mentioned above. For instance, through the setting a desirable point spread function (PSF) as a target, the optimization should be performed with respect to the US frequency, LM frequency, shape of envelop, bandwidths in the respective directions, wavenumbers etc.). The PSF desirable for echo signals (beams obtained as the results of the superposition processing or spectra frequency division processing) is basically selected by using the image quality quantitatively evaluated using the present invention or visually confirmed, the SNRs of echo signals to be generated, the contrast to be generated, the energies to be generated etc. as measures. When using the PSF for the displacement measurement as well, the measurement accuracy etc. can also be used as a measure (when performing only the displacement measurement, the evaluation of the image quality is not required.). The experimental data or simulation data can also be used as constraints for the above-mentioned optimization. The optimization can also be performed directly using the echo SNR, measurement accuracy, contrast, image quality quantitatively evaluated using the present invention or visually confirmed etc. as measures. The optimization can also be used for other beamforming, and with the coherent superposition processing and division processing or with no such processing.

The designs for the echo imaging and displacement measurement mentioned above (the designs can also be permitted to be performed with trial and error.) can be permitted to be performed respectively or in a combinational manner by using same measures that are set under a proper control. Otherwise, the design can also be permitted to be performed such that both the original measures are satisfied with simultaneously. Thus, the same beamforming can be permitted to be performed for both purposes. The respective PSFs required for the optimization mentioned above can be permitted to be ones properly set for the respective purposes, or in a combinational manner by using the same PSF that is set under a proper control. Otherwise, a PSF can also be permitted to be set by the optimization such that both the original measures for the purposes are satisfied with simultaneously. Thus, the same beamforming can be permitted to be performed for both purposes.

Also a thermal source for performing treatment using a high intensity ultrasound or a mechanical source for a radiation force imaging (e.g., imaging of generated shear wave propagation imaging etc.) can be permitted to be evaluated in detail similarly by performing the spectral analysis with respect to acquired echo signals (i.e., responses with respect to the transmission of a high intensity ultrasound or the radiation of a force) or by calculating a 2D autocorrelation function as mentioned above. Also same parameters can be permitted to be designed for both a thermal source and a mechanical source. As a representative application, a position of the thermal treatment (source) or a mechanical source can be detected with a high accuracy (the thermal source and mechanical source can be permitted to be generated simultaneously or successively.). In addition, the same optimization method can be permitted to be used such that a desirable position is heated in a desirable shape with a desirable power; and such that a mechanical source is generated at a desirable position in a desirable shape with a desirable intensity (when plural thermal sources or mechanical sources are generated, the respective of them can be permitted to be dealt with independently or the plural source are dealt with simultaneously.). Similarly to the above-mentioned applications, a beam direction, a direction to a focus position (there may be plural foci), a focus position, sound pressure shape distribution, a beam shape etc. can be measured with a high accuracy and with a high spatial resolution. Globally they can also be evaluated. For the high intensity ultrasound treatment or the generation of a mechanical source for generating a deformation or a shear wave, the present inventor has been also proposing to perform the LM (lateral modulation) that yields a frequency in the lateral direction orthogonal to the set axial direction (i.e., the axial direction can also be permitted to be steered) in order to obtain a high spatial resolution or to control the direction of deformation or shear wave propagation by controlling the mechanical source (there may exist plural sources), in which for the crossed beams used, similarly to the generation of echo data, the present invention can be used for obtaining a desirable position of focus or beam crossing, for instance (as mentioned above, the determination of parameters can be permitted to be performed using the optimization method or with trial and error). For the optimization, optimization can also be permitted to be performed directly with respect to the heating efficiency, temperature rising, heating effectiveness (degeneration), deformation, strain tensor, strain rate tensor, acceleration vector, displacement vector, velocity vector, propagation direction or propagation speed of shear wave etc. instead of the parameters relate to the sound pressure, thermal source or radiation force as a measure. When transmitting a high intensity ultrasound or radiating a force, echo imaging or tissue displacement measurement can be permitted to be performed using echo signals received with respect to the transmitting or radiating. In such a case, the specific evaluation about the generated beams, the designing and the optimization can be performed similarly as mentioned above, or if necessary, simultaneously performed as mentioned above.

Thus, in these applications, the present invention permits to specifically evaluate beams generated using the beamforming for achieving LM (lateral modulation) beamforming, multidirectional beamforming, ASTA (a steering angle) beamforming, non-steered (frontal) beamforming, steered beamforming with an invariant or variant steering angle, other beamforming; and then the present invention permits the effective use of the evaluation as mentioned above. The present invention can also be used for other beamforming not mentioned in the present invention.

For one-directional displacement measurement, the following method (1) to (4) can be used.

Method (1): The displacement component $d(x,y)$ in the beam direction shown in FIG. 12 (or a displacement of shear the wave propagation) can be calculated by dividing the temporal change in an instantaneous phase $\Delta\theta(x,y)$ between two frames, calculated at the position through implementation of the multidimensional moving-average processing similarly (non-patent document 3), by $(fx^2+fy^2)^{1/2}$ as follows, $$d(x,y)=\Delta\theta(x,y)/(fx^2+fy^2)^{1/2} \quad (A)$$

Figure 12:
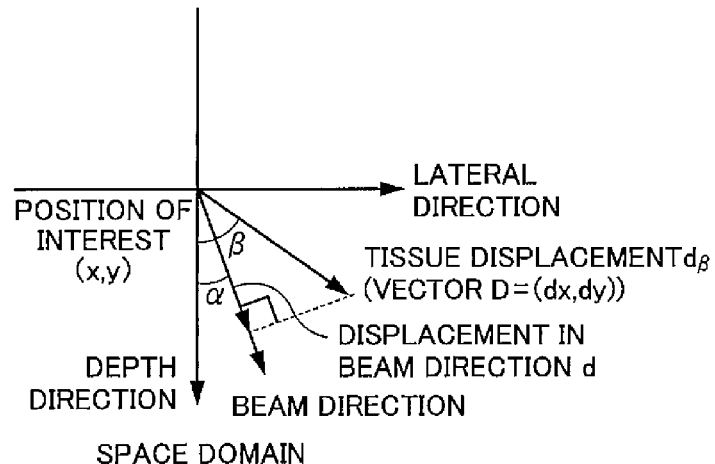
FIG. 12 shows for position of interest (x,y) in 2-dimensional measurement case, illustration for exhibiting displacement in beam direction d, tissue displacement $d_\beta$, beam angle (azimuth angle) α and angle of tissue displacement β and tissue displacement vector D.

Thus, for instance, if a tissue displacement can be confirmed from a US image or other morphological images etc. as an angle $\beta$ shown in FIG. 12, the displacement $d_\beta$ in the direction can be calculated as follows, $$d_\beta(x, y) = d(x, y)/\cos(\beta - \alpha)$$
$$= \Delta\theta(x, y)/(fx\cos\beta + fy\sin\beta), \ldots (A')$$

Figure 10:
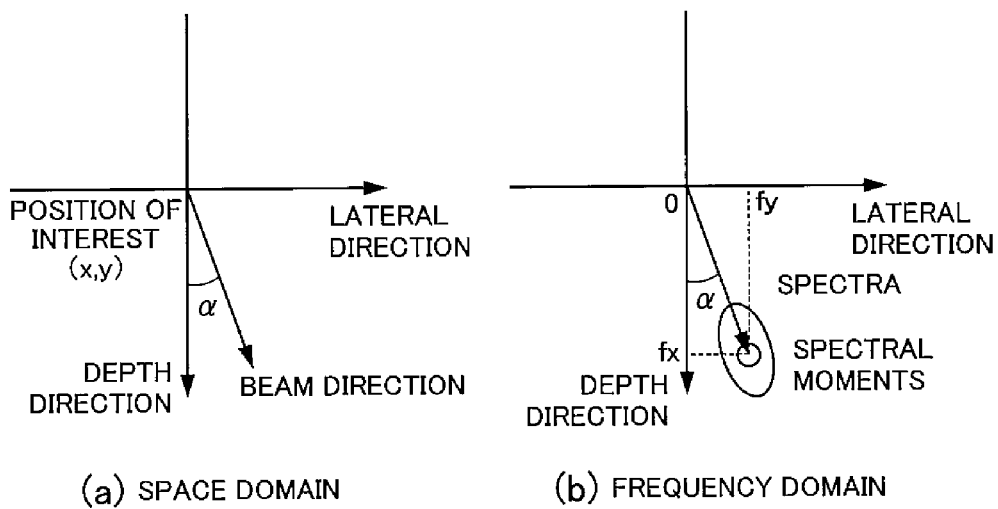
FIG. 10 shows illustrations for position of interest (x,y) in 2-dimensional measurement case, relation between beam angle α and 1st spectral moments (frequencies) and instantaneous frequencies (fx, fy) in space domain [FIG. 10(a)] and frequency domain [FIG. 10(b)]

In this way, such displacements can be measured in real-time without performing rotation of the coordinate system. Basically, when generating a steered beam electronically or mechanically, it is desired to direct the beam as in the direction of the tissue displacement as possible similarly to in a conventional measurement case. The calculations about the temporal change in an instantaneous phase and instantaneous frequencies in the respective directions are same as those used in the multidimensional autocorrelation and Doppler methods (non-patent document 3). It can be explained that the effectiveness of performing the multidimensional moving-average is same as that in a case where a one-directional displacement measurement method such as the conventional autocorrelation method or Doppler method is implemented to the respective directions of x and y axes (FIG. 10).

In a special case, the direction of a blood flow in a blood vessel running parallel to the body surface (for instance, a blood flow in the carotid) can be expressed using $\beta\approx90°$. In such a case, the tissue displacement is expressed as follows, $$d_\beta(x, y) = d(x, y)/\sin\alpha$$
$$= \Delta\theta(x, y)/fy,$$

and the displacement $dx(x,y)$ in the depth direction is $dx(x,y)=0$ or $dx(x,y)\approx0$. That is, the tissue displacement $d_\beta(x,y)\approx dy(x,y)$ (the lateral displacement). Thus, in this case, Method (1) is equivalent to the lateral Doppler method (patent document 1) that the present inventor developed. In this way, Method (1) can include the lateral Doppler method, and note that being different from in the lateral Doppler method, in Method 1 the lateral axis is not required to be set in the direction of such a lateral displacement. Also not that Method 1 permits measurement of a displacement in an arbitrary direction. A measurement method using the expression (A) can also be used for an arbitrary beam angle $\alpha$. When using a transducer with an arbitrary aperture geometry, and a beam is generated in a frontal direction with respect to the aperture without performing beam steering ($\alpha=0°$), Method (1) can also be permitted to be used. However, in this case, $\beta=90°$ should not be dealt with as a measurement target.

Figure 11:
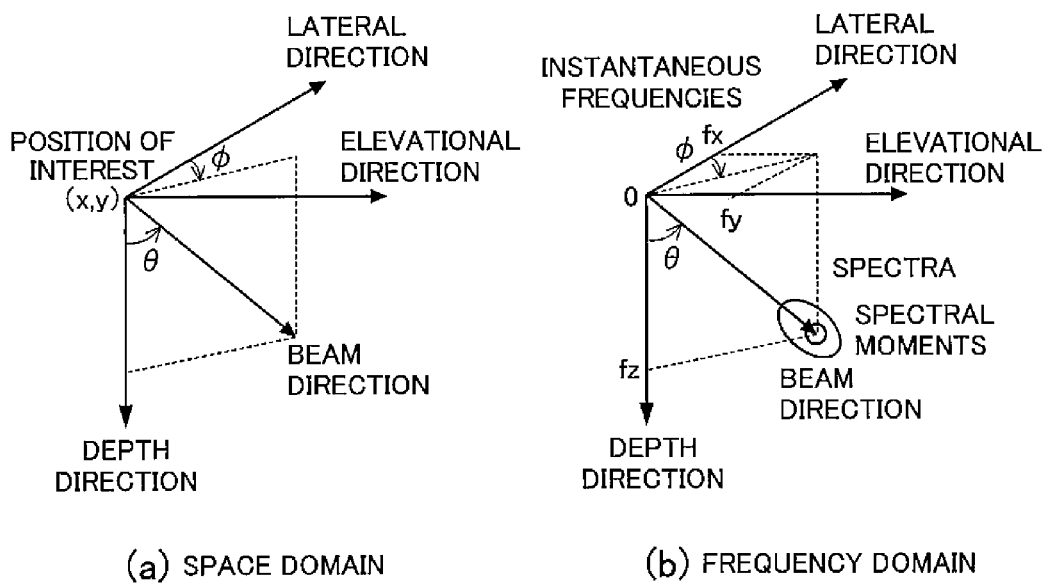
FIG. 11 shows for position of interest (x,y,z) in 3-dimensional measurement case, relations among beam angle φ (azimuth angle), θ (polar angle), 1st spectral moments (frequencies), and instantaneous frequencies (fx,fy,fz) in space domain [FIG. 11(a)] and frequency domain [FIG. 11(b)]

In a 3D measurement case shown in FIG. 11, the displacement component $d(x,y,z)$ in the beam direction at the position of interest $(x,y,z)$ expressed by the Cartesian coordinate system can be calculated by dividing the temporal change in an instantaneous phase $\Delta\theta(x,y,z)$ between two frames, calculated at the position through implementation of the multidimensional moving-average processing similarly (non-patent document 3), by $(fx^2+fy^2+fz^2)^{1/2}$ as follows, $$d(x,y,z)=\Delta\theta(x,y,z)/(fx^2+fy^2+fz^2)^{1/2}$$

and the respective azimuth angle $\phi$ and polar angle $\theta$ can be calculated as follows, $$\tan\phi=fy/fx$$

$$\cos\theta=fz/(fx^2+fy^2+fz^2)^{1/2}$$

The evaluation of the generated beams in a 3D space can be permitted to be carried out by performing this 3D spectral analysis (in addition to the frequencies, the bandwidths and spectra distribution etc., are evaluated) or by dealing with the 3D autocorrelation function equivalent to the 3D spectra (the 3D autocorrelation function being different from a 2D one, there also exists an elevational direction.). The direction of a beam generated or a focus position, focus position, sound pressure shape distribution etc. can be measured with a high accuracy and with a high spatial resolution. These can also be permitted to be measured globally. In addition to a 2D case, such a specific evaluation can be used for echo imaging, tissue displacement measurement, high intensity ultrasound treatment, radiation force imaging etc.

When the direction of tissue displacement $d_\beta$ can be obtained, the tissue displacement $d_\beta$ can be calculated similarly in a 2D case.

Figure 13:
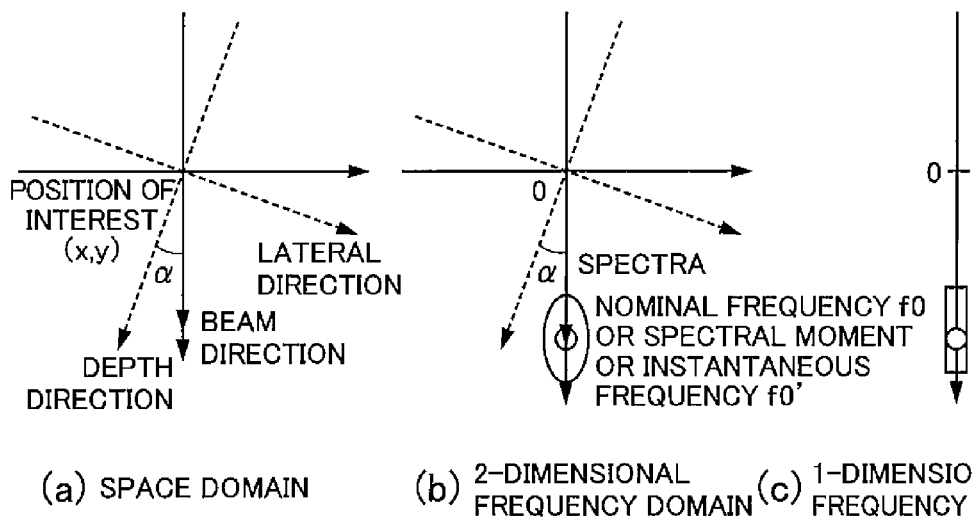
FIG. 13 shows for position of interest (x,y) in 2-dimensional measurement case, illustration for exhibiting space domain obtained after rotating coordinate system by angle −α [FIG. 13(a)]; 2-dimensional frequency domain [FIG. 13(b)]; 1-dimensional frequency domain [FIG. 13(c)]

Conventional one-directional displacement measurement method: When using a one-directional displacement measurement method, the displacement $d(x,y)$ in a direction expressed using an inaccurate beam angle data $\alpha'$ (i.e., a beam angle $\alpha'$ set at performing beamforming) is calculated using the nominal frequency $f_0$ of a transducer, or the 1st spectral moments of spectra estimated through the local 2D or 1D Fourier's transform etc. of echo data with abeam-direction axis obtained by rotating the coordinate system by an inaccurate angle data $-\alpha'$ or the instantaneous frequencies $f_0'$ (above-explained) estimated from the rotated echo data (FIG. 13) (the moving-average to be performed should be multidimensional.) as follows, $$d(x,y)=\Delta\theta(x,y)/f_0 \text{ or } d(x,y)=\Delta\theta(x,y)/f_0'$$

and the tissue displacement $d_\beta(x,y)$ in a direction with an angle $\beta$ is calculated using the inaccurate angle data $\alpha'$ as follows, $$d_\beta(x,y)=d(x,y)/\cos(\beta-\alpha')$$

In a real-world processing, when performing beamforming in a frontal direction with respect to the physical effective aperture, measurement is widely performed under the condition that α' and fy are zeros, and in such a case, the tissue displacement $d_\beta(x,y)$ is calculated as follows, $$d_\beta(x, y) = d(x, y)/\cos\beta$$

$$= \Delta\theta(x, y)/fx\cos\beta$$

However, in Method(1), $\Delta\theta(x,y)$ is divided by $(fx\cos\beta+fy\sin\beta)$ and then, if measurement is performed on the beam direction with a spatial resolution, such a measurement error due to non-zero $fy\sin\beta$ is not generated. Thus, below-disclosed method can also be obtained.

Method (2): When performing the rotation of a coordinate system, it is also effective to obtain a spatial resolution and an accuracy in beam angle data. In this case, it is also effective to use a beam angle estimated globally from the 1st spectral moments of spectra estimated with respect to echo data in an ROI, although the beam angle data has no spatial resolution and a lower accuracy than that with a spatial resolution. That is, using the accurately obtained beam angle data α, the echo data can be permitted to be rotated by −α. In the former processing, echo data is required to be rotated locally at the respective position of interest in an ROI, whereas in the latter processing, echo data in an ROI can be permitted to be rotated globally and then, although the accuracy becomes lower than the former processing, the calculations are remarkably fewer. The frequency required for the displacement measurement can be set to the nominal frequency $f_0$ of a transducer, or the 1st spectral moments of spectra estimated through the local or global 2D or 1D Fourier's transform etc. of echo data with a beam-direction axis or the above-explained instantaneous frequencies $f_0'$ (the moving-average to be performed should be multidimensional.). The rotation of a coordinate system can be performed in a space domain or in a frequency domain as mentioned. The displacement $d(x,y)$ in the beam direction can be accurately measured, and the further calculations can also be performed similarly as mentioned above.

In a 3D measurement case, similarly a coordinate system can be permitted to be rotated using accurately measured azimuth angle $\phi$ and polar angle $\theta$. The frequency required for the displacement measurement can be set to the nominal frequency $f_0$ of a transducer, or the 1st spectral moments of spectra estimated through the local or global 3D, 2D or 1D Fourier's transform etc. of echo data with a beam-direction axis or the above-explained instantaneous frequencies $f_0'$ (the moving-average to be performed should be multidimensional.). The displacement $d(x,y,z)$ in the beam direction can be accurately measured, and the further calculations can also be performed similarly as mentioned above.

However, note that for the 2D and 3D measurement cases, similarly to the conventional one-directional displacement measurement, however, being different from Method (1), it requires time to carry out the coordinate rotation and then real-time measurement cannot be obtained. Moreover, when using approximate calculations on the coordinate rotation, measurement errors are generated.

Figure 14:
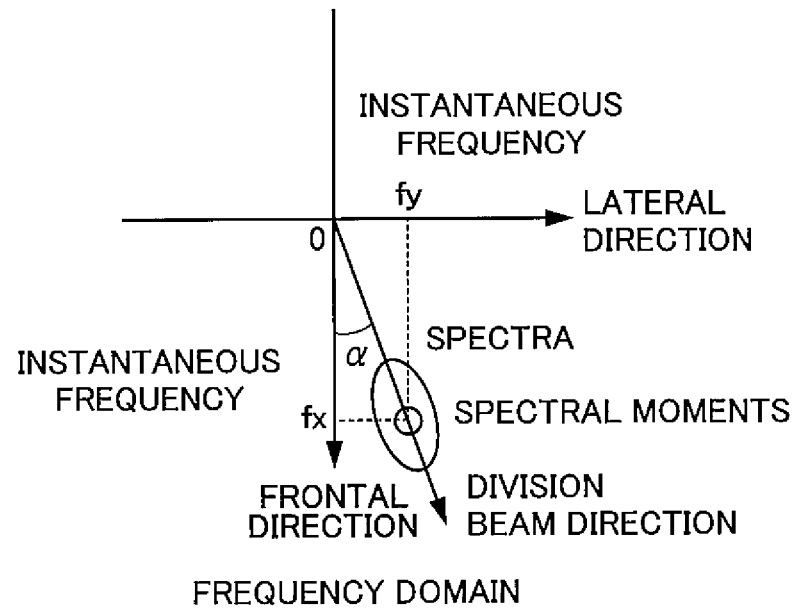
FIG. 14 shows for use of spectra frequency division method in 2-dimensional measurement case, illustration for exhibiting spectra division and 1st spectral moments (frequencies) and instantaneous frequencies (fx,fy)

Method (3): When using the spectra frequency division method for a displacement vector measurement, i.e., when the multidimensional autocorrelation or Doppler method is implemented on echo data obtained through scanning with a single beam, by dividing spectra in an arbitrary direction such as in a beam direction similarly, accurately measured at the respective positions of interest (FIG. 14), simultaneous equations comprising Doppler equations, required for the multidimensional autocorrelation or Doppler method, derived from the respective parts of divided spectra, are solved. In a 2D displacement vector measurement case, when obtaining more than three parts of divided spectra (≥3) through the application of the above-mentioned spectra frequency division, simultaneous equations derived are solved through the least squares method or the regularization method. Being dependent on SNRs of the respective parts of divided spectra, confidences about measurement results, other data such as a phase or a frequency etc. (that can be determined a priori or a posteriori through stochastic evaluations etc.), etc., errors of such simultaneous equations can be permitted to be least-squared with being weighted (i.e., application of the so-called weighted least squares method). Such processing can be performed with respect to other measurements mentioned below. Otherwise, solutions of the Doppler equations can be permitted to be additionally averaged by summation processing to obtain a measurement result. In this case, being dependent on SNRs of the respective parts of divided spectra, confidences about measurement results, other data such as a phase or a frequency etc. (that can be determined a priori or a posteriori through stochastic evaluations etc.), etc., the corresponding solutions to be additionally averaged can be permitted to be weighted. Such processing can also be performed with respect to other measurements mentioned below. Thus, the displacement component $d(x,y)$ in a beam direction can be calculated with a high accuracy, and similarly to other methods mentioned above, the tissue displacement $d_\beta(x,y)$ can also be calculated with a high accuracy.

Similarly, in a 3D measurement case, by dividing spectra into three or four, or more parts of divided spectra using arbitrary planes such as planes including the axis of a beam direction accurately measured, simultaneous equations comprising Doppler equations, required for the multidimensional autocorrelation or Doppler method, derived from the respective parts of divided spectra are solved to obtain a 3D displacement vector measurement. When obtaining more than four parts of divided spectra (≥4) through the application of the spectra frequency division, simultaneous equations derived are solved through the least squares method or the regularization method. Being dependent on SNRs of the respective parts of divided spectra, confidences about measurement results, other data such as a phase or a frequency etc. (that can be determined a priori or a posteriori through stochastic evaluations etc.), etc., errors of such simultaneous equations can be permitted to be least-squared with being weighted (i.e., application of the so-called weighted least squares method). Otherwise, solutions of the Doppler equations can be permitted to be additionally averaged by summation processing to obtain a measurement result. In this case, being dependent on SNRs of the respective parts of divided spectra, confidences about measurement results, other data such as a phase or a frequency etc. (that can be determined a priori or a posteriori through stochastic evaluations etc.), etc., the corresponding solutions to be additionally averaged can be permitted to be weighted. Thus, the displacement component $d(x,y,z)$ in a beam direction can be calculated with a high accuracy, and similarly the further calculations can be performed as mentioned above.

As mentioned above, for the spectra frequency division, extracting of spectra etc., windows (or frequency responses of filters) can be permitted to be properly used.

Method (4): In the case where the same spectra frequency division method is used, the present inventor previously confirmed that for spectra centered on the frontal axis in a frequency domain similarly shown in FIG. 13 (i.e., directly obtainable when performing frontal beamforming or non-steered beamforming), and the combination of dividing the spectra into two parts by the central axis and the use of the multidimensional autocorrelation or Doppler method yields a higher accuracy on the measurement of a beam-directional displacement component than the conventional autocorrelation or Doppler method (for instance, non-patent document 5). These measurements are equivalent to ones using the multidimensional autocorrelation or Doppler method with no lateral modulation (i.e., beamforming with no steering). Therefore, when the beam angle data a measured with a high accuracy and with a spatial resolution can be used, similarly to in Method (2), the coordinate rotation is performed at the respective positions of interest, and a high accuracy measurement can also be achieved, although real-time measurement cannot be obtained because it takes time to carry out the coordinate rotation. A simultaneously obtained displacement components in the directions orthogonal to the beam direction can be permitted not to be used. Also, similarly in Method (2), for the coordinate rotation, it is effective to use the beam angle data globally estimated from the 1st spectral moments of spectra corresponding echo data in an ROI. Although the measurement accuracy becomes lower than that obtained with the spatial resolution in beam angle data, the calculations decrease significantly. The frequency required for the displacement measurement can be set to the nominal frequency $f_0$ of a transducer, or the 1st spectral moments of spectra estimated through the local or global 2D or 1D Fourier's transform etc. of echo data with a beam-direction axis or the above-explained instantaneous frequencies $f_0'$. The rotation of a coordinate system can be performed in a space domain or in a frequency domain as mentioned. When obtaining more than three parts of divided spectra ($\geq 3$) through the application of the spectra frequency division, simultaneous equations derived are solved through the least squares method or the regularization method. Being dependent on SNRs of the respective parts of divided spectra, confidences about measurement results, other data such as a phase or a frequency etc. (that can be determined a priori or a posteriori through stochastic evaluations etc.), etc., errors of such simultaneous equations can be permitted to be least-squared with weighting (i.e., application of the so-called weighted least squares method). Otherwise, solutions of the Doppler equations can be permitted to be additionally averaged by summation processing to obtain a measurement result. In this case, being dependent on SNRs of the respective parts of divided spectra, confidences about measurement results, other data such as a phase or a frequency etc. (that can be determined a priori or a posteriori through stochastic evaluations etc.), etc., the corresponding solutions to be additionally averaged can be permitted to be weighted. Thus, the displacement component $d(x,y)$ in a beam direction can be calculated with a high accuracy, and further calculations can be performed similarly. That is, similarly to other methods mentioned above, the tissue displacement $d_\beta(x,y)$ can also be calculated with a high accuracy. When approximate calculations are performed on the coordinate rotation, measurement errors are generated.

Also in a 3D measurement case, similarly a coordinate system can be permitted to be rotated using accurately measured azimuth angle $\phi$ and polar angle $\theta$ such that spectra become centered on the frontal axis in a frequency domain, and in such a case, three octant spectra of four octant spectra (i.e., four parts of divided spectra) or all the four octant spectra, or three, four or more parts of divided spectra using an arbitrary planes such as planes including the axis of a beam direction accurately measured, simultaneous equations comprising Doppler equations, required for the multidimensional autocorrelation or Doppler method, derived from the respective parts of divided spectra are solved to obtain a 3D displacement vector measurement. When obtaining more than four parts of divided spectra ($\geq 4$) through the application of the spectra frequency division, simultaneous equations derived are solved through the least squares method or the regularization method. Being dependent on SNRs of the respective parts of divided spectra, confidences about measurement results, other data such as a phase or a frequency etc. (that can be determined a priori or a posteriori through stochastic evaluations etc.), etc., errors of such simultaneous equations can be permitted to be least-squared with weighting (i.e., application of the so-called weighted least squares method). Otherwise, solutions of the Doppler equations can be permitted to be additionally averaged by summation processing to obtain a measurement result. In this case, being dependent on SNRs of the respective parts of divided spectra, confidences about measurement results, other data such as a phase or a frequency etc. (that can be determined a priori or a posteriori through stochastic evaluations etc.), etc., the corresponding solutions to be additionally averaged can be permitted to be weighted. Thus, the displacement component $d(x,y,z)$ in a beam direction most accurately measured of all there displacement components can obtained, and the displacement $d(x,y,z)$ can be used for the further calculations mentioned above.

As mentioned above, for the spectra frequency division, extracting of spectra tec., windows (or frequency responses of filters) can be permitted to be properly used.

In Methods (3) and (4), according to the confidences or SNRs of the respective echoes corresponding to the parts of divided spectra, the simultaneous equations can be permitted to be solved with being weighted. The least squares method or the regularization method can be permitted to be used. The methods are disclosed, for instance, in patent documents 2, 4, 6, 7 etc. The multidimensional autocorrelation or Doppler method is a displacement vector measurement method that does not directly require such beam angle data about plural beams generated. Alternatively, Methods (1) to (4) that use high accuracy beam angle data about the generated beams can be used to obtained high accuracy beam-directional displacements corresponding the respective generated beams, which realizes another accurate displacement vector measurement method, i.e., in the method, the accurately measured beam-directional displacements are synthesized to yield an accurate displacement vector measurement. When using Methods (3) and (4), the parts of divided spectra to be obtained corresponds to spectra of quasi-beams generated through the spectra division processing, and then, similarly the generated quasi-beams can also be specifically evaluated such as beam directions of the quasi-beams generated. Below, these are specifically disclosed. Another displacement vector measurement method is disclosed from the paragraph [0106].

In Methods (1) and (2) in addition to Methods (3) and (4), when the number of parts of divided spectra and/or raw spectra (possibly including ones obtained at a different time) to be used becomes larger than the number of unknown tissue displacement vector components, for instance, for the one-directional displacement component measurement, simultaneous equations comprising more than two equations derived from two spectral parts can be solved using the least squares method (being dependent on SNRs of the respective parts of divided spectra or raw spectra, confidences about measurement results, other data such as a phase or a frequency etc. (that can be determined a priori or a posteriori through stochastic evaluations etc.), etc., errors of the simultaneous equations can be permitted to be least-squared with being weighted.), or plural solutions obtained from the equations can be additionally averaged (being dependent on SNRs of the respective parts of divided spectra or raw spectra, confidences about measurement results, other data such as a phase or a frequency etc. (that can be determined a priori or a posteriori through stochastic evaluations etc.), etc., the corresponding solutions to be additionally averaged can be permitted to be weighted.).

As mentioned above, the plural spectra can permit to include raw spectra obtained before being divided (i.e., no processed spectra), spectra obtained after being divided (for instance, as mentioned below, the spectra divided in the following directions, i.e., the vertical or horizontal direction, the beam direction, the direction orthogonal to the beam direction etc. or the spectra divided in plural different manners with respect to same spectra etc.), new spectra obtained using the coherent superposition method (various combinations can be permitted to be performed using plural steered beams with different steering angles, ultrasounds with different US frequencies, ultrasounds with different depth or lateral bandwidths, ultrasounds with other different US parameters such as a F-number etc., a basic or 2nd order harmonic wave, etc.), spectra obtained after being divided in different manners with respect to same spectra such obtained (for instance, as mentioned above, vertical division, horizontal division, division in the beam direction or in the direction orthogonal to the beam direction etc.), superpositions with various combinations of spectra such obtained.

For echo imaging, the respective spectra (complex analytic signals) obtained through the above-mentioned coherent superposition or spectra frequency division can be permitted to be used. The respective spectra or signals are superposed with being weighted to be displayed (non-use of spectra within some bandwidth is equivalent to being weighted by zero.). The superposition can also be permitted to be performed in a combination with complex analytic signals obtained with no being divided. On such superpositions, superposition can be performed after detecting the respective signals (i.e., incoherent detection) or before detecting the respective signals (i.e., the detection can be performed on the coherently superposed signals). This is similar to the lateral modulation (LM).

For Methods (1) to (4), as mentioned above, if necessary, the mechanical steering angle θm (FIG. 6) can be permitted to be detected using a sensor, and if necessary, the display can be permitted to be touched or traced using a pen etc. as an interface to input angle data to be used for setting a coordinate system or angle correction of a coordinate system. If necessary, at performing beamforming or after performing beamforming, in order to determine an angle α or β, or a coordinate system properly, angle correction data about the electronic steering angle (FIG. 5) or mechanical steering angle (FIG. 6) can be permitted to be displayed, and during performing the angle correction, the angle can be permitted to be displayed on a polar coordinate system etc. such that the observer can visually confirm if the angle correction is proper or not. If necessary, angle correction can be permitted to be automatically performed using such angle correction data by the electronic steering (the synthetic aperture can be permitted to be performed.) or mechanical steering. The direction of a tissue displacement can be permitted to be automatically obtained from a displayed ultrasound image or other medical images (morphological images) obtained simultaneously or at the same temporal phase, for instance, on the basis of the information about tissue structures such as a blood vessel. Otherwise, the direction of a tissue displacement can be permitted to be evaluated by touching or tracing the tissue structures visualized on the display. Also angle correction data can be permitted to be automatically obtained on the basis of the measurement results on a tissue displacement. Thus, an arbitrary method or device can be permitted to be used. These are useful for performing image matching between other medical images such as X-ray CT or MRI.

Figure 20:
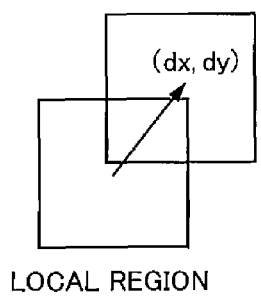
FIG. 20 shows illustration for assuming rigid displacement of local region in 2-dimensional region of interest.

For Methods (1) to (4), the above-mentioned, the present inventor's previously developed multidimensional phase matching method is effective (non-patent documents 1 to 5). The multidimensional phase matching prevents the measurement from phase aliasing due to a large displacement in the beam direction, and increases the measurement accuracy in all displacement vector components by increasing a correlation or a coherency between the pre- and post-deformed echo signals obtained from target tissues by performing a coarse matching of the echo signals in a multidimensional space (i.e., including lateral and/or elevational direction) using the coarse displacement estimates obtained using a block matching method such as the multidimensional cross-correlation method or multidimensional cross-spectrum phase gradient method etc. before performing fine measurement of the target beam-directional displacement with respect to the same echo signals using Method (1) to (4). For the coarse and fine measurements performed with respect to the phase matching, echo data can be permitted to be same signals received (beamformed), signals generated via different beamforming, or signals generated from different received (beamformed). The phase matching can be permitted to be performed using displacement measurement results obtained in advance in the neighborhood of the position of interest in an ROI. FIG. 20 shows schematics for a 2D ROI, the use of two displacement components. For a 3D ROI, similarly the phase matching can be performed.

As other phase matching methods, the correlation method or SAD (Sum Absolute Difference) method can be used and are also used as a displacement measurement method for compression of a dynamic image. However, when these measurement methods are used to the tissue displacement measurement, the corresponding displacement vector components can only be estimated as the multiples of the sampling intervals of digital rf-echo signals (i.e., digital values of displacements can be obtained.). Thus, although the methods cannot be used for the fine measurement, the above-mentioned coarse measurement can be performed by the methods.

In Methods (2) and (4), the coordinate rotation is performed. At least, echo data within a searching region of which size is determined by the magnitude of a tissue displacement are rotated. The timing of performing the phase matching can be obtained as follows, (i) after completing the coordinate rotation, the coarse and fine measurements are performed successively via the phase matching processing; (ii) before performing the coordinate rotation, the coarse measurement and the phase matching processing are completed, and after performing the coordinate rotation, the fine measurement is performed; and (iii) before performing the coordinate rotation, the coarse measurement is completed and obtained coarse displacement measurement data are re-expressed as those expressed on the coordinate system obtained after the coordinate rotation and the re-expressed coarse displacement data are used for the phase matching processing on the rotated coordinate system and then, the fine measurement is performed.

(II) Displacement Vector Measurement

When using the multidirectional beamforming method, as mentioned above, the respective beam angles with respect to the generated beams are measured at the respective positions of interest with a high accuracy, and by applying one of Methods (1) to (4) to the respective beams, the respective beam-directional displacements are measured with a high accuracy; and then, by synthesizing the measured beam-directional displacements, an arbitrary directional displacement vector can be measured with a high accuracy.

Figure 15:
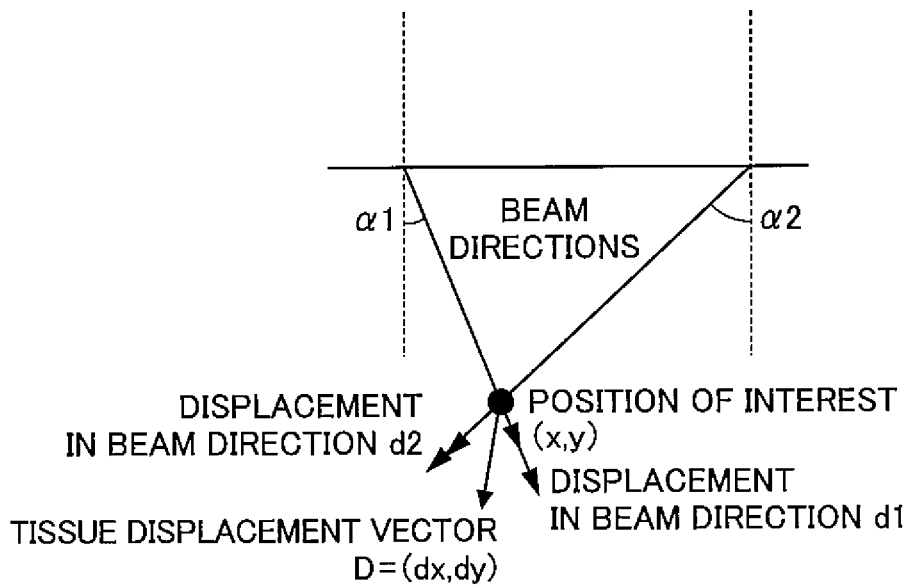
FIG. 15 shows for use of multidirectional beamforming method for position of interest (x,y) in 2-dimensional measurement case, illustration for exhibiting beam angles $\alpha_1$ and $\alpha_2$, displacements measured in the respective directions $d_1$ and $d_2$, and target displacement vector D.

For instance, when 2D displacement vector measurement is performed using one of the above-mentioned Methods (1) to (4), as shown in FIG. 15, plural beams with different directions are crossed at the position of interest (x,y). The measured two beam angles are expressed by $\alpha_1$ and $\alpha_2$, respectively, and the measured displacements in the respective beam directions are expressed by $d_1$ and $d_2$, respectively, the tissue displacement vector D=(dx,dy) can be calculated by solving the following simultaneous equations, $\cos \alpha_1 dx + \sin \alpha_1 dy = d_1$ $\cos \alpha_2 dx - \sin \alpha_2 dy = d_2$ (B)

That is, the tissue displacement vector D=(dx,dy) can be obtained as follows, $dx = (\sin \alpha_2 d_1 + \sin \alpha_1 d_2)/(\sin \alpha_2 \cos \alpha_1 + \sin \alpha_1 \cos \alpha_2)$ $dy = (\cos \alpha_2 d_1 - \cos \alpha_1 d_2)/(\sin \alpha_2 \cos \alpha_1 + \sin \alpha_1 \cos \alpha_2)$.

Particularly when there exist no obstacles such as a bone etc. laterally symmetrically steered beams can be permitted to be used (i.e., $\alpha_1 = \alpha_2$). When generating more than three beams with different beam angles (beams with different properties such as steered beams etc. or beams synthesized through division or superposition etc.), the 2D displacement vector can be calculated on the basis of the least squares method. Being dependent on SNRs of the respective spectra, confidences about measurement results, other data such as a phase or a frequency etc. (that can be determined a priori or a posteriori through stochastic evaluations etc.), etc., errors of such simultaneous equations can be permitted to be least-squared with being weighted. In such a case, a Doppler equation with respect to an unknown one-directional displacement derived using a single beam can be permitted to be used simultaneously. Otherwise, a calculated displacement vector data can be additionally averaged with a displacement data calculated using a single beam or some combination of equations. In this case, being dependent on SNRs of the respective spectra, confidences about measurement results, other data such as a phase or a frequency etc. (that can be determined a priori or a posteriori through stochastic evaluations etc.), etc., the corresponding solutions to be additionally averaged can be permitted to be weighted.

Here, for the same echo data, assume that the multidimensional autocorrelation or Doppler method is used at the same position of interest (x,y) and then, the Doppler equation with respect to the beam with a beam angle $\alpha_1$ holds as follows, $fx_1 dx + fy_1 dy = \Delta\theta_1$, where $fx_1$ and $fy_1$ are, at the same position (x,y), the instantaneous frequencies in the depth and lateral directions, respectively, which have a relation with the beam angle $\alpha_1$ as follows, $\alpha_1 = \tan^{-1}(fy_1/fx_1)$ and $\Delta\theta_1$ is, at the same position (x,y), the temporal change in an instantaneous phase. By dividing the equation by $fx^2+fy^2)^{1/2}$, an equation equivalent to the 1st equation of equations (B) can be obtained as follows, $(fx_1/(fx^2+fy^2)^{1/2})dx + (fy_1/(fx^2+fy^2)^{1/2})dy = d_1$ Similarly, with respect to another beam with a beam angle $\alpha_2$, an equation equivalent to the 2nd equation of equations (B) can be derived. Thus, it can be confirmed that the use of Method (1) in the multidirectional beamforming method is equivalent to the lateral modulation (LM) method.

Methods (3) and (4) of one-directional displacement measurement methods [(I)] were specifically disclosed above as the beam-directional displacement measurement methods on the basis of a displacement vector measurement. Quasi-beams can be obtained correspondingly to the single quadrant or octant spectra, or the 1D spectra through the spectra frequency division of a single quadrant or octant spectra, or a 1D spectra. For Methods (3) and (4), the multidimensional autocorrelation or Doppler method is used to measure a displacement vector. Also in this case, beam angles of the quasi-beams generated are similarly calculated, and on the basis of equations (B), a displacement vector can be calculated. As mentioned above, although the multidimensional autocorrelation or Doppler method does not directly require to calculate beam angles of the plural beam generated, Methods (1) to (4) using accurate data of beam angles generated can also yield an accurate displacement vector measurement through synthesizing using the accurately measured beam-directional displacements. The position of beam crossing can also be evaluated similarly to in the LM methods.

When 3D displacement vector measurement is performed using one of the above-mentioned Methods (1) to (4), at least three or more beams with different directions are crossed at the position of interest (x,y,z). For instance, the measured three beam angles are expressed by ($\phi 1, \theta 1$), ($\phi 2, \theta 2$) and ($\phi 3, \theta 3$), respectively, and the measured displacements in the respective beam directions are expressed by $d_1$, $d_2$ and $d_3$, respectively, the tissue displacement vector D=(dx,dy,dz) can be calculated by solving the following simultaneous equations, $\sin \theta_1 \cos \phi_1 dx + \sin \theta_1 \sin \phi_1 dy + \cos \theta_1 dz = d_1$ $\sin \theta_2 \cos \phi_2 dx + \sin \theta_2 \sin \phi_2 dy + \cos \theta_2 dz = d_2$ $\sin \theta_3 \cos \phi_3 dx + \sin \theta_3 \sin \phi_3 dy + \cos \theta_3 dz = d_3$ Here, note that being different from the angles $\alpha_1$ and $\alpha_2$ shown in FIG. 15 for the 2D displacement vector measurement case (i.e., the positive directions of the angles of the two beams are inverted), all the angles with respect to the three beams have the same positive directions as those shown in FIG. 11. Also recall that not a single angle but two angles (azimuth and polar angles) are used to express a beam direction in a 3D coordinate system. It can also be confirm that in this 3D displacement vector measurement, similarly to 2D displacement vector measurement, the method is equivalent to the LM.

When generating more than four beams with different beam angles (beams with different properties such as steered beams etc. or beams synthesized through division or superposition etc.), the 3D displacement vector can be calculated on the basis of the least squares method. Being dependent on SNRs of the respective spectra, confidences about measurement results, other data such as a phase or a frequency etc. (that can be determined a priori or a posteriori through stochastic evaluations etc.), etc., errors of such simultaneous equations can be permitted to be least-squared with being weighted. In such a case, a Doppler equation with respect to an unknown one-directional displacement derived using a single beam or simultaneous equations with respect to unknown two displacement components derived using two beams can be permitted to be simultaneously used. Otherwise, a calculated displacement vector data can be additionally averaged with a displacement data calculated using a single beam or some combination of equations. In this case, being dependent on SNRs of the respective spectra, confidences about measurement results, other data such as a phase or a frequency etc. (that can be determined a priori or a posteriori through stochastic evaluations etc.), etc., the corresponding solutions to be additionally averaged can be permitted to be weighted.

Similarly in 2D displacement vector measurement, the spectra frequency division methods [i.e., Methods (3) and (4)] of one-directional displacement measurement methods [(I)] can also be used.

Particularly when there exist no obstacles such as a bone etc. symmetrically steered beams can be permitted to be used. The above-mentioned steered beams can permit to include a non-steered (frontal) beam instead. When generating more than four beams with different beam angles, the 3D displacement vector can be calculated on the basis of the least squares method.

Similarly in one-directional displacement measurement, if required, the mechanical steering angle θm (FIG. 6) can be permitted to be performed. Similarly, the phase matching is also performed. In the case, the coarse measurement can be permitted to be performed with respect to echo data obtained as the superposition of echo data acquired using the multidirectional steered beams. Otherwise, echo data obtained with respect to the respective steering can also be permitted to be used. In addition, for instance, echo data obtained by performing other beamforming such as the non-steered (frontal) beamforming etc. can also be permitted to be used.

As the displacement measurement method for evaluating shear waves generated, not the one-directional displacement measurement but the multidimensional displacement vector measurement should be performed in that measurement of all the displacement vector components as well as a high accuracy can be achieved. Although both the measurement methods permit real-time measurement, the one-direction displacement measurement method can be effective in decreasing the beamforming processing and completing the measurement more in a high speed. Concretely, the shear wave propagation speed, shear wave propagation direction, shear wave vibration displacement, shear wave vibration velocity, shear wave vibration acceleration, shear wave vibration amplitude, shear wave vibration frequency, shear wave vibration direction, shear wave phase etc. can be measured.

The reconstruction (differential-type inverse analysis) of an anisotropic elastic moduli using strain (tensor), for instance is disclosed in detail in patent document 2 and 6, and non-patent document 20 etc. disclosed by the present inventor. There are also disclosed documents for the reconstruction (inverse analysis) of an isotropic shear modulus (for instance, non-patent document 19, 23 etc. and many others), in which the reconstruction is performed by approximating the dynamic motion equations by the Helmholtz equations under the assumptions of a local homogeneity of shear modulus (the spatial derivatives are zeros.), a constant density (a typical value is used.), no mechanical sources in an ROI etc. By using an assumption about a density, the propagation speed can also be estimated. The present invention permits to properly generate a thermal source or a mechanical source (plural sources can also be generated.), and also to control the propagation directions of low frequency elastic waves (shear waves). Thus, generating plural propagation directions and implementing the same inverse analysis processing in the respective directions permit to estimate the respective shear moduli in the respective directions, and then an anisotropic shear modulus can be estimated by measuring the same or larger number of shear wave propagations as that of unknown (anisotropic) shear moduli. That is, the (anisotropic) shear moduli can be calculated by solving simultaneous equation derived on the basis of the expressions about the shear modulus tensor with respect to the coordinate rotation (i.e., relations between the anisotropic shear moduli before and after the coordinate rotation on the basis of the tensor calculation, mathematically, basic expressions about a tensor with 4th rank). The expressions are also described in detail in a text book about a solid mechanics (non-patent document 24). If required, the simultaneous equations can also be permitted to be solved using the least squares method or performing additional averaging of the solutions (i.e., in an over-determined case).

When calculating the shear moduli under the above-mentioned assumptions, the spatial resolutions of the reconstruction results decrease. On the other hand, the reconstruction methods (differential types) disclosed in documents 2 and 6, and non-document 20 etc. are useful also in that a mechanical source can exist in an ROI. However, note that when directly performing measurement of the shear wave propagation speed, inherent to the reason that the wavelength of shear wave is long, because the estimation of a shear modulus (or moduli) is performed under the same assumptions, the spatial resolution as well as the reconstruction accuracy is low. However, such a measurement can also permit to be useful clinically.

(III) New Lateral Modulation Processing and Imaging

Regarding echo imaging, when the lateral modulation (LM) is one of operation modes, although the above-mentioned several methods for generating LM echo data, such LM echo data can also be generated simple in a short time on the basis of a conventional non-steered (frontal) beamforming or the steered beamforming with a steering angle (ASTA).

As shown in FIG. 16(a), when performing transmission of a beam in a frontal direction, and spectra are obtained as shown in FIG. 16(b), although lateral low frequency spectra has high SNRs, disregarding the lateral low frequency spectra by padding zero spectra can generate a lateral cosine modulation. That is, after performing the beamforming, the processing can be permitted to be performed via the spectral analysis. Such LM imaging is useful in that the conventional imaging is also permitted to be performed. When a beam is steered, disregarding laterally partial spectra in a neighborhood of the steered-beam direction, modulation in the lateral direction orthogonal to the beam direction can be achieved. In this modulation, for instance, a rectangular function can be effectively used as an apodization function in order to obtain a wide lateral bandwidth. For the detection processing, the method is optional such as the envelop detection method, the parabolic detection method, etc. For imaging of ultrasound frequencies or the effectiveness of LMs realized by the present invention, rf-echo signals can also be directly used, and when the dynamic range of target echo signals is large, the respective positive and negative values of the signals can be effectively log-compressed (for instance, gray-scaled imaging, negative or positive imaging are effective.). Otherwise, it is also effective to display the parabolically detected, superposed rf-signals as well as the superposition of parabolically detected rf-signals. The latter imaging has a feature that reflection or strong scattering is displayed more brightly and also, speckle reduction can be obtained with respect to such plural spectra obtained through the spectra frequency division. When the speckle shape is an observing target, or for the speckle reduction, the envelop detection can be permitted to be performed. Regarding the speckle reduction performed by such superposition of incoherent signals has a long history, to the present inventor's knowledge, in addition to a case where plural beams with different US frequencies are used and a case where plural steered beams with different steering angles are used (inmost cases, the above-mentioned envelop detection is performed.), there also exists a case where new methods on the basis of the spectra frequency division method that the present inventor previously developed (patent document 1). For the spectra frequency division, for instance, as mentioned above, the spectra can be divided in the following directions, i.e., the vertical or horizontal direction, the beam direction, the direction orthogonal to the beam direction etc. or the spectra can be divided in plural different manners with respect to same spectra etc. The spectra obtained through simultaneous or respective divisions can be effectively used not only for the tissue displacement measurement but also the speckle reduction.

Although the disregarding low lateral frequency spectra decreases the spatial resolution of echo signals, because a higher accuracy measurement can be achieved using a higher frequency of echo signals as the present inventor previously clarified (for instance, non-patent document 3), the new disregarding processing is effective for increasing the measurement accuracy of a lateral displacement, particularly when such a decrease in a spatial resolution becomes no problem, i.e., when the displacement of the object has a low frequency distribution. However, it is also cautious that the extra disregarding of spectra leads to a decrease in an echo SNR and decrease in a measurement accuracy as well as the decrease in a spatial resolution. The cutoff frequency can be determined by evaluating the quasi-steered beams generated on the basis of the present invention; the cutoff frequency can also be determined optimally in advance with respect to the transducer parameters or beamforming parameters through actual measurement or simulation (the database can be permitted to be made and used.); and then the design or optimization of the parameters can also be permitted to be performed. Similarly, for the displacement measurement in a beam direction, the disregarding low axial frequency spectra also permits to increase the measurement accuracy by increasing an axial frequency of the echo signals. However, it is also cautious for the axial displacement measurement to perform extra disregarding of spectra. Also similarly, such parameters can be designed or optimized to achieve high accuracy measurement.

For echo imaging, the shape of a beam or a speckle (sound pressure) is required to be considered. These depend on the beamforming parameters and the transducer parameters used for generating beams, parameters for the division processing (positions and directions of the division, and shapes, weighting, bandwidths (spectra and shapes) or the 1st spectral moments (instantaneous frequencies) of spectra to be obtained by the division etc.), the cutoff frequencies and filters (frequency responses, shapes of bandwidths, above-mentioned windows etc.) etc. It is desirable that in addition to such filtering parameters used after beamforming, the beamforming parameters and transducer parameters for generating beams, and the parameters for the division required after generating the beams are properly designed in a combinational manner. As mentioned above, for the design, simulations and experiments are effective (the database can be permitted to be made and used.). Also the design is permitted to be performed using the optimization method mentioned above. For instance, through the setting a desirable point spread function (PSF) as a target, the optimization should be performed with respect to the US frequency, LM frequency, shape of envelop, bandwidths in the respective directions, wavenumbers etc.). The PSF desirable for echo signals is basically selected by using the image quality quantitatively evaluated using the present invention or visually confirmed, the SNRs of echo signals to be generated, the contrast to be generated, the energies to be generated etc. as measures. When using the PSF for the displacement measurement as well, the measurement accuracy etc. can also be used as a measure (when performing only the displacement measurement, the evaluation of the image quality is not required.). The experimental data or simulation data can also be used as constraints for the above-mentioned optimization. As mentioned above, the optimization can also be performed directly using the echo SNR, measurement accuracy, contrast, image quality quantitatively evaluated using the present invention or visually confirmed, etc. The optimization can also be used for other beamforming, and with the coherent superposition processing and division processing or with no such processing.

The designs for the echo imaging and displacement measurement mentioned above can be permitted to be performed respectively or in a combinational manner by using same measures that are set under a proper control. Otherwise, the design can also be permitted to be performed such that both the original measures are satisfied with simultaneously. Thus, the same beamforming can be permitted to be performed for both purposes. These designs can also be permitted to be performed with trial and error. The respective PSFs required for the optimization mentioned above can permit to be ones properly set for the respective purposes, or in a combinational manner by using the same PSF that is set under a proper control. Otherwise, a PSF can also be permitted to be set by the optimization such that both the original measures for the purposes are satisfied with simultaneously. Thus, the same beamforming can be permitted to be performed for both purposes.

Figure 16:
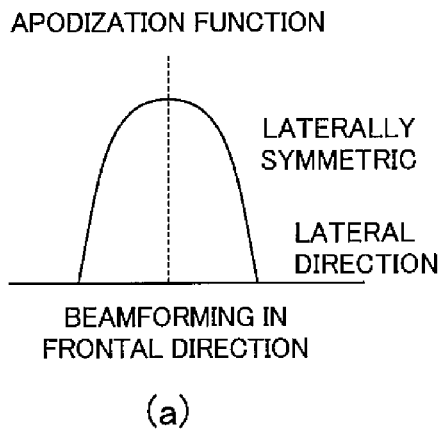
FIG. 16(a) and FIG. 16(b) show for 2-dimensional measurement case, illustration for explaining lateral modulation processing to be performed after non-steered (frontal) beamforming.
FIG. 16(c) and FIG. 16(d) shows for 2-dimensional measurement case, illustration for explaining interchangeability of lateral cosine and sine modulations.
Figure 16:
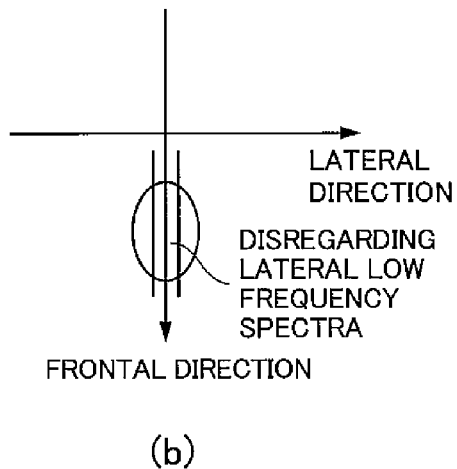
Figure 16:
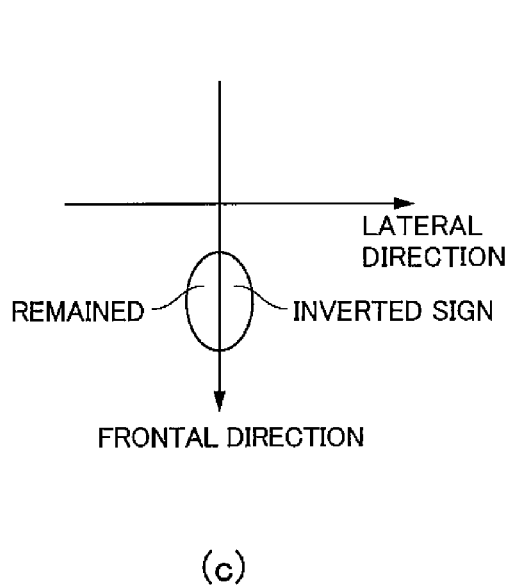
Figure 16:
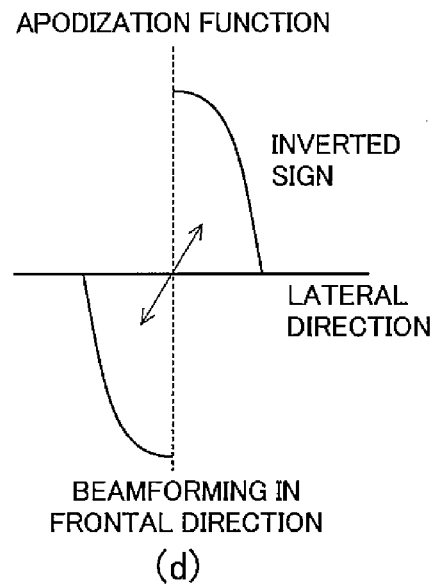

As shown in FIG. 16($c$), after performing the spectral analysis, inverting signs of spectra existing in either one of two quadrants yields the lateral sine modulation that is obtainable using the apodization function as shown in FIG. 16($d$). Thus, when performing the lateral sine modulation using the apodization as shown in FIG. 16($d$), after performing the spectral analysis, the inverting the signs of such spectra yields an echo image that is obtainable using the apodization. shown FIG. 16($a$). And then, if the lateral low frequency spectra are disregarded, sine modulation can be exchanged by cosine modulation. Also for sine modulation performed, disregarding low frequency spectra permits to control a lateral modulation frequency. Thus, mathematically the exchangeability of lateral cosine modulation and lateral sine modulation for each other can be confirmed. In an engineering, such a signal processing has not been applied anywhere. When using a lateral same cutoff frequency, the sine modulation yields a slightly higher lateral modulation frequency than the cosine modulation (particularly when the cutoff frequency has approximately a zero., the difference in a lateral modulation frequency is large.), and then the lateral sine modulation suitable to the displacement measurement rather than the lateral cosine modulation. The sine modulation is not always used for the displacement measurement; and although the cosine modulation is suitable to the echo imaging rather than the sine modulation (particularly, the parabolic detection can be effectively used), also such a desirable cosine imaging is not always performed. In order to decrease the processing, the same modulation can be permitted to be used for both the echo imaging and the displacement measurement.

Such processing is performed for echo imaging and tissue displacement measurement. However, such processing can also be performed on the above-mentioned received signals obtained with respect to performing the high intensity thermal treatment and radiation force imaging (or shear wave propagation imaging), and then in a similar manner, the above-mentioned echo imaging processing and displacement measurement processing. Thus, similarly in the above-mentioned treatment case, the evaluation, design or optimization about the above-mentioned beamforming parameters and transducer parameters can be performed respectively; and also when the above-mentioned various other functions are performed simultaneously, similarly the design and optimization can be permitted to be properly performed.

Figure 17:
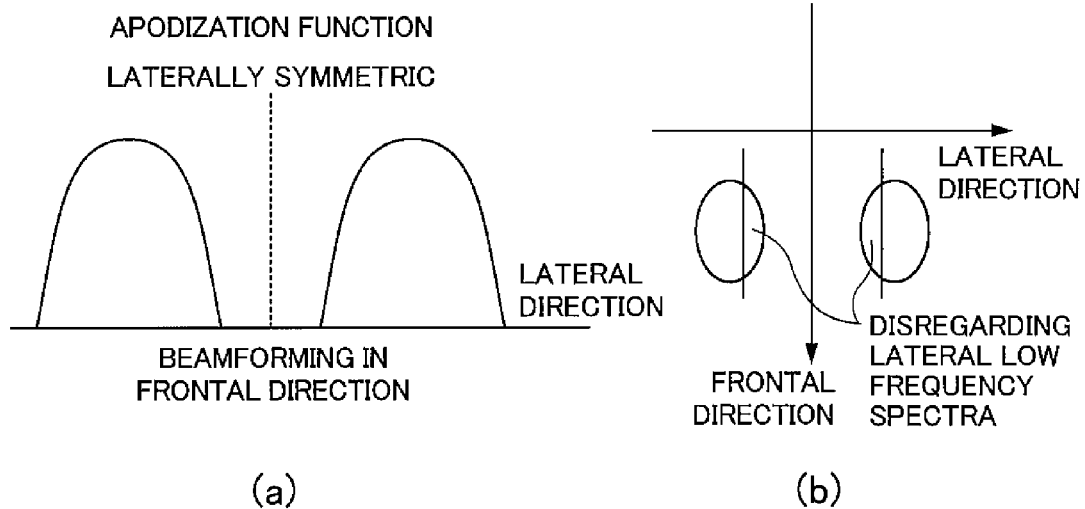
FIG. 17(a) and FIG. 17(b) shows for 2-dimensional measurement case, illustration for explaining lateral cosine modulation and lateral cosine modulation with disregarding lateral low frequency spectra.
FIG. 17(c) and FIG. 17(d) shows for 2-dimensional measurement case, illustration for explaining interchangeability of lateral cosine and sine modulations.
Figure 17:
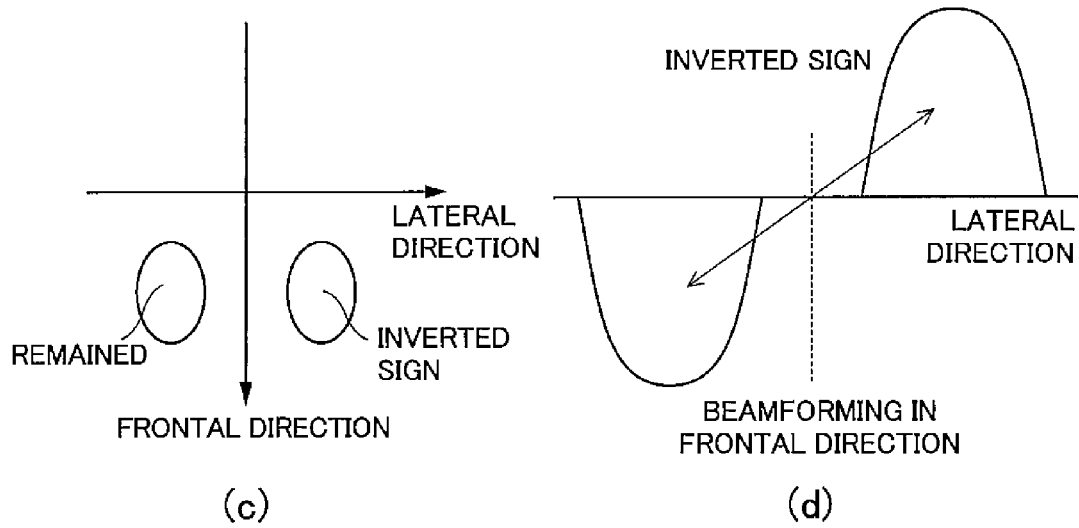

Such processing can also be applied to the above-mentioned lateral cosine modulation (non-patent document 3, 6, 7, etc., FIG. 17(*a*)) or lateral sine modulation (FIG. 17(*d*)) that the present inventor developed, i.e., similarly the processing for increasing instantaneous frequencies through disregarding low frequency spectra (a beam width become large; a bandwidth becomes small, FIG. 17(*b*)) and the processing for exchanging the lateral cosine modulation and lateral sine modulation (FIG. 17) for each other can be per formed. For instance, when using an apodization function expressed using two rectangular windows is used for performing the lateral modulation (LM) for 2D echo imaging, a beam with a lateral large bandwidth can be generated. However, if the lateral modulation frequency is small, the lateral waves become not to be confirmed in the corresponding point spread function (PSF). In such a case, the use of such a sine modulation is effective for obtaining lateral waves etc.

Figure 18:
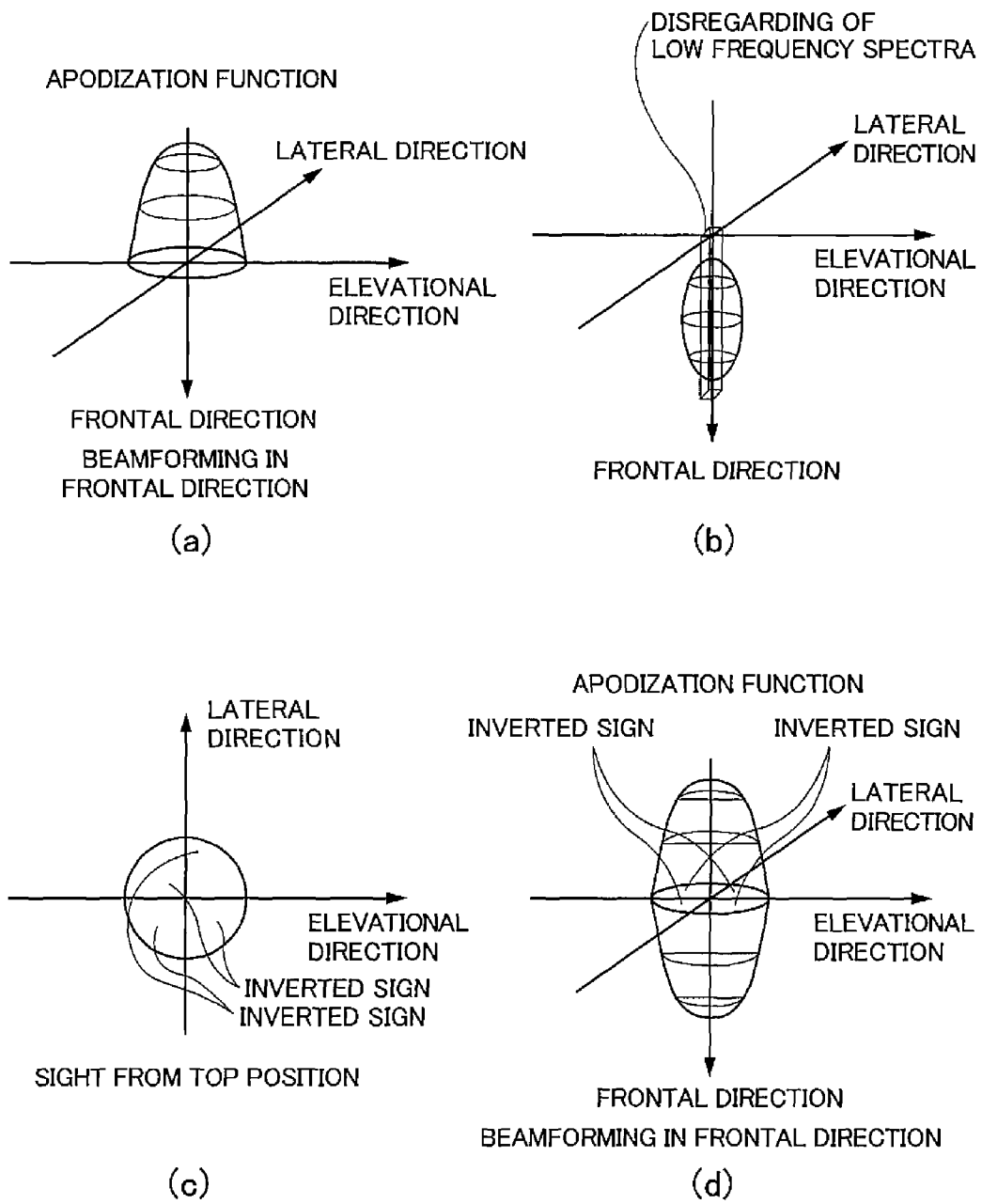
FIG. 18(a) and FIG. 18(b) shows for 3-dimensional measurement case, illustration for explaining lateral modulation processing to be performed after non-steered (frontal) beamforming.
FIG. 18(c) and FIG. 18(d) shows for 3-dimensional measurement case, illustration for explaining interchangeability of lateral cosine and sine modulations.
Figure 19:
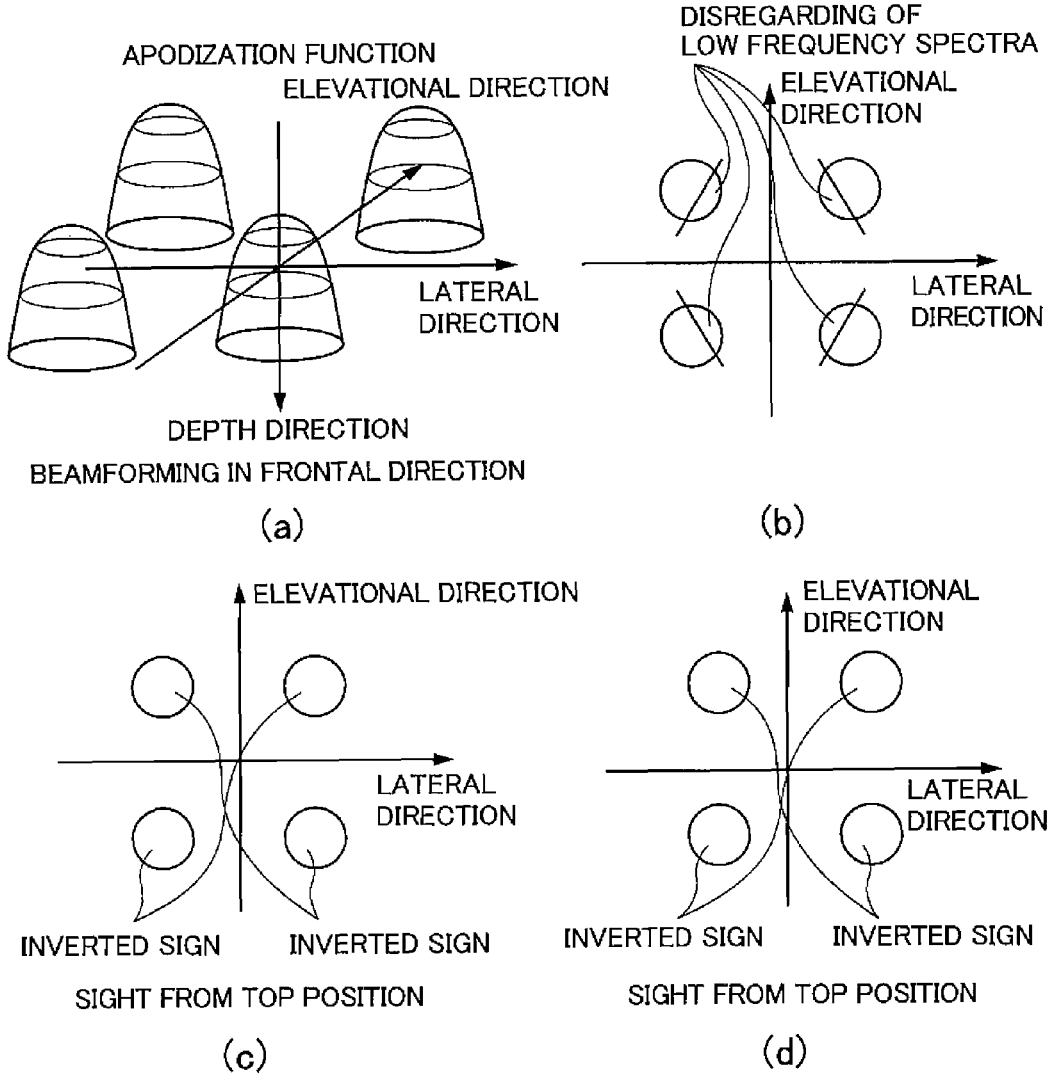
FIGS. 19(a) and 19(b) shows for 3-dimensional measurement case, illustration for explaining lateral cosine modulation and lateral cosine modulation with disregarding lateral low frequency spectra.
FIG. 19(c) and FIG. 19(d) shows for 3-dimensional measurement case, illustration for explaining interchangeability of lateral cosine and sine modulations.

Also in a 3D space, the frontal beamforming (FIG. 18) and plural steered beamforming (FIG. 19) can be performed. Then, also when performing such beamforming, after performing the beamforming, the disregarding low frequency spectra (for instance, lateral low frequency spectra or spectra in the neighborhood of steered beam direction) and the exchanging the lateral sine modulation and the lateral cosine modulation can be performed for the respective purposes. In cases including the above-mentioned 2D case, the exchanging sine and cosine modulations for each other can be performed by inverting in a frequency domain signs of spectra existing in either one of two quadrants or two octants symmetric with respect to a frequency axis corresponding to the depth direction after performing such beamforming. Respective FIG. 18 and FIG. 19 show for a 3D case, illustration about the processing for such beamforming.

The modulation can be applied to echo imaging, and tissue displacement measurement and tissue displacement vector measurement. Generally, the respective cosine and sine modulations are suitable to the echo imaging and tissue displacement measurement, and the present invention permits to perform the exchanging the cosine and sine modulations for each other. However, when a proper lateral modulation can be performed using parabolic functions etc.,. the performing the lateral sine modulation is not always more effective than the lateral cosine modulation. However, the respective sine modulation and cosine modulation obtained through such processing can be permitted to be used for the echo imaging and displacement measurement instead of performing the respective beamforming (the new processing decrease calculations significantly). For the displacement measurement, other methods from those of the present invention can be permitted to be used. The present invention can also be used in cases where a central direction with respect to single quadrant or octant spectra or plural quadrant or octant spectra is steered as well as not steered (i.e., in a frontal direction). Also in a 3D space, all the imaging can be performed similarly.

The above-mentioned detection methods used for the single beam scanning can also be used, and then the imaging can be permitted to be performed. Also speckle reduction can be performed (more than the beams theoretically required for performing the modulation are used, or the spectra frequency division can be permitted to be used to obtain plural quasi-beams in such a case.). Also for the displacement vector measurement, the spectra frequency division method can be used. Similarly, it is effective to regard high frequency spectra properly. The cutoff frequency can be determined by evaluating the quasi-steered beams generated on the basis of the present invention; the cutoff frequency can also be determined optimally in advance with respect to the transducer parameters or beamforming parameters through actual measurement or simulation (the database can be permitted to be made and used.); and then the design or optimization of the parameters can also be permitted to be performed. For echo imaging, the shape of a beam or a speckle (sound pressure) is required to be considered. It is desirable that in addition to filtering parameters used after beamforming (the cutoff frequencies and filters (frequency responses, shapes of bandwidths, above-mentioned windows etc.), the beamforming parameters and transducer parameters for generating beams, and the parameters for the division required after generating the beams (positions and directions of the division, and shapes, weighting, bandwidths (spectra and shapes) or the 1st spectral moments (instantaneous frequencies) of spectra to be obtained by the division) are properly designed in a combinational manner. Similarly, the optimization is also effective. This is also for displacement measurement. These can also be applied to other beamforming, and with the coherent superposition processing (parameters: positions and directions of the superposition, and shapes, weighting, bandwidths (spectra and shapes) or the 1st spectral moments (instantaneous frequencies), etc.) and division processing or with no such processing.

The designs for the echo imaging and displacement measurement mentioned above can be permitted to be performed respectively or in a combinational manner by using same measures that are set under a proper control. Otherwise, the design can also be permitted to be performed such that both the original measures are satisfied with simultaneously. Thus, the same beamforming can be permitted to be performed for both purposes. These designs can also be permitted to be performed with trial and error. The respective PSFs required for the optimization mentioned above can permit to be ones properly set for the respective purposes, or in a combinational manner by using the same PSF that is set under a proper control. Otherwise, a PSF can also be permitted to be set by the optimization such that both the original measures for the purposes are satisfied with simultaneously. Thus, the same beamforming can be permitted to be performed for both purposes.

Such processing can also be performed on the above-mentioned received signals obtained with respect to performing the high intensity thermal treatment and radiation force imaging (or shear wave propagation imaging), and then in a similar manner, the above-mentioned echo imaging processing and displacement measurement processing. Thus, similarly in the above-mentioned treatment case, the evaluation, design or optimization about the above-mentioned beamforming parameters and transducer parameters can be performed respectively; and also when the above-mentioned various other functions are performed simultaneously, similarly the design and optimization can be permitted to be properly performed.

Thus, the present invention permits to evaluate the generated ultrasound (US) beams in detail, and then using data obtained, the ultrasound imaging with a high spatial resolution in a lateral direction, the displacement measurement with a high accuracy, the change in an instantaneous phase, the shear wave vibration displacement, the shear wave vibration velocity, the shear wave vibration acceleration, the shear wave amplitude, the shear wave vibration frequency, the shear wave vibration direction, the shear wave phase etc. can be measured. The beam direction, the direction to a focus, the focus position, the crossing position of beams, the sound pressure shape distribution (1D, 2D or 3D distribution), the beam shape etc. can be measured with a high accuracy or if required, with a high spatial resolution. The present invention can also be used for echo imaging. In this manner, high quality imaging and high accuracy tissue displacement (vector) can be permitted to be performed. Such evaluation can be performed on various beamforming as mentioned above. Regarding echo imaging, on simple frontal beamforming performed by a conventional ultrasound diagnosis apparatus, the lateral modulations that the present inventor previously developed can be realized through the signal processing after performing the beamforming. Whenever such lateral modulation is performed, regardless the lateral modulation methods, the cosine and sine modulations can be exchanged for each other. Regarding the tissue displacement measurement, through the calculation of a beam direction at position of interest with a high accuracy, high accuracy measurement can also be performed on the one-directional displacement (for instance, a lateral displacement) and the displacement vector as well as the conventional Doppler measurement (i.e., an axial displacement). Because the methods of the present invention do not always yield the best measurement and imaging, a function that other various beamforming possibly performed using the same hardware components can be permitted to be used with a function for selecting other displacement measurement methods. For instance, if there exists no obstacles and no problem about the target tissue motion during generation of plural beams, and lateral modulation with a high lateral frequency can be performed from the beginning, the original lateral modulation should be selected rather than the lateral modulation achieved through the frontal beamforming. Thus, the imaging and displacement measurement apparatus related to the present conduct form can permit to have a function/method (including an automatic function) for selecting the proper combination of a beamforming method and a displacement measurement method via the measurement control unit 3 or the data processing unit 1 etc. Also the present invention can be permitted to be installed into other apparatus such as other ultrasound diagnosis apparatus equipped with other functions, a nuclear magnetic resonance diagnosis apparatus, various optical diagnosis apparatuses etc. That is, an arbitrary apparatus using wave propagation can be permitted to be used.

According to the present invention, for the echo imaging and the displacement measurement, the direction to a focus, the focus position, the crossing position of beams, the sound pressure shape distribution (1D, 2D or 3D distribution), the beam shape etc. can be measured with a high accuracy and if required, with a high spatial resolution, and then for the respective or both purposes, properly the beamforming parameters and the transducer parameters can be evaluated. On the basis of the evaluation, the parameters can also be designed or optimized to obtain high quality imaging (for instance, with a high spatial resolution, with a large contrast, with a high lateral frequency, with reduced speckles effectively etc.) and high accuracy tissue displacement (vector) can be permitted to be performed. The apparatus can also be permitted to be equipped with the function for performing the high intensity ultrasound treatment or shear wave propagation imaging using a radiation force etc. and also in such a case, the present invention is used (plural mechanical and thermal sources can also be permitted to be generated through successive or simultaneous radiation.). Echo data obtained with respect to the generated beams using such a function can also be permitted to be used for the echo imaging and the displacement measurement. And then, as mentioned above, the parameters can be permitted to be designed or optimized with a consideration about the change in a temperature, degeneration, deformation or wave propagation etc. Thus, the specific evaluation of beams via the present invention is effective to properly perform the evaluation, design and optimization of the beamforming parameters and the transducer parameters. Not only the apparatus to be yielded via the present invention can be permitted to be equipped with various functions properly but also perform various functions simultaneously.

The present invention can be applied to an apparatus that uses an arbitrary wave such as other mechanical waves, electromagnetic waves, thermal waves etc. in addition to the ultrasound echo signals, shear waves. Instead of an echo wave, a transmission wave can also be permitted to be used.

The data processing unit 1 can also permit to have a feature for calculating the strain tensor components or the strain by convolving a spatial differential filter with a limited bandwidth (a 3D, 2D or 1D spatial filter) or multiplying the frequency response of spatial differential filter with a limited bandwidth (3D, 2D or 1D frequency response) to the 3D or 2D displacement vector in a 3D ROI, the 2D displacement vector in a 2D ROI, the one-directional displacement component in a 3D, 2D or 1D ROI measured via the data processing unit 1. Similarly, the strain (tensor components, distribution, temporal series), strain rate (tensor components, distribution, temporal series), acceleration (vector components, distribution, temporal series), velocity (vector components, distribution, temporal series) can also be permitted to be calculated from the measured displacement (vector components, distribution, temporal series) or strain (tensor components, distribution, temporal series) by implementing a temporal differential filter with a limited bandwidth. Also, the detection or the measurement of an instantaneous phase change can also be permitted to be performed, and the shear wave propagation wave speed or the shear wave propagation direction (distribution or temporal series) can also be permitted to be measured.

A display unit 10 (FIG. 1) such as CRT etc. can also be permitted to be configured to display at least one of measurement results such as displacement vector components or a displacement, strain tensor components or a strain, strain rate tensor components or a strain rate, acceleration vector components or an acceleration, velocity vector components or a velocity, distributions thereof, temporal series thereof, or a B-mode image obtained through the detection such as the envelop detection or the parabolic detection etc. of an ultrasound echo data frame at the same temporal phase, which is used for the measurements or not (for instance, one obtained with different beamforming), an ultrasound echo data frame almost at the same temporal phase, an ultrasound echo data frame at different temporal phases to be superposed (for instance, one obtained with a synchronized to a heartbeat etc.). From tensor quantities, principle strains or principle strain rates can also be calculated and these can also be permitted to be displayed. If necessary, the measured distributions can be displayed in a color on the B-mode (gray) image similarly to so-called color Doppler, a kind of Elastography. All the imaging methods with a spatial resolution about a spatial position, a direction, a magnitude can be permitted to be used. Vectors, principle strains or principle strain rates can also be permitted to be displayed using a vector line map. Moreover, these can also be permitted to be superposed each other and displayed.

The measured change in an instantaneous phase or the position having the change in an instantaneous phase (distribution, temporal series), shear wave propagation (propagation speed, propagation direction, vibration displacement, vibration velocity, vibration acceleration, vibration amplitude, vibration frequency, vibration direction, phase etc., the distributions thereof, the temporal series thereof. etc.) etc. can be permitted to be displayed similarly. These results can also be permitted to be displayed with superposition on the nuclear magnetic resonance images. When the measurements of a displacement (vector) or a phase is performed on the basis of the nuclear magnetic resonance signals, the measurement results obtained can be permitted to be displayed with superposition on the nuclear magnetic resonance image or other medical images. This can also be applied to cases using other diagnosis apparatuses.

On the basis of the measured strain tensor distribution data calculated from the displacement vector distribution data measured by the present conduct form, the shear modulus distribution can be permitted to be calculated. For the calculation or measurement, a material of a known shear modulus should be used as a reference material. Such a reference region is included in an ROI. The reference region is a region of a known absolute shear modulus, or one with a shear modulus estimated in advance. In order to achieve a stable measurement of a shear modulus distribution, the reference region should exist widely in the direction that (orthogonally) crosses with the direction of a dominant deformation direction. Thus, when using an ultrasound transducer is used as a mechanical compressor for compressing the object, such a reference material can be permitted to be put between the transducer and the object. In this case, the reference material can be permitted to be fixed with or installed into the transducer. The stress tensor distribution or the pressure distribution, or the mechanical source distribution can also be permitted to be calculated. Although the spatial resolution is low, such mechanical properties can also be permitted to be calculated form the shear wave propagation speed or the shear wave propagation direction etc.

Measurement of the shear wave distribution, the shear wave propagation direction (distribution) or the temporal series data of the shear modulus distribution etc. also permits accurate measurement of the shear wave propagation speed. Also the permitting the control of a mechanical source generated by a radiation force or a thermal source generated by a high intensity ultrasound allows the generation of shear wave propagating in an arbitrary direction, and then the measurement of shear wave propagation speeds in plural directions allows the estimation of an anisotropic shear modulus (distribution). Otherwise, the observing with a high accuracy the shear waves or deformations generated in proper directions also permits the high accuracy measurement of shear modulus (isotropic or anisotropic) on the basis of the strain tensor-measurement-based shear modulus reconstruction. Acquiring data on shear wave propagating in proper plural directions or strain (tensor) for deformations generated in proper plural directions permits to increase the measurement accuracy.

This is similar to the cases of other diagnosis apparatuses used.

The purposes of measuring the displacement vector distribution, the strain tensor distribution, the shear modulus distribution, viscosity distribution are to perform the non-destructive evaluation of properties or examination about objects, substances and materials related to a static or dynamic mechanics, or non-invasive diagnosis or examination about living things. For instance, when dealing with human soft tissues, the present inventor focuses the tissue low frequency elastic properties that changes with the progress of disease or changes in tissue characteristics. Instead of vibrating tissues externally, or performing a compression, the radiation force or a heartbeat, blood pulsation etc. can also be permitted to be used as a mechanical source for generating the tissue deformations, and the measured shear modulus values or the distributions (morphology) thereof calculated from the measured tissue deformations can be permitted to be used for a differential diagnosis of the tissues. Also the fluid properties of body fluids such as a blood etc. can be permitted to be performed similarly. The measurement results obtained in this manner can be permitted to be displayed similarly with the display unit 10 (i.e., distributions and values).

The imaging and displacement measurement apparatus related to the present conduct form can be permitted to be used for monitoring the treatment effectiveness (including a temperature change: for instance, non-patent documents 17 and 18) of the high intensity ultrasound treatment, the radiotherapy, the laser therapy, the electromagnetic rf-wave or micro radiation therapies, etc. In this case, the imaging and displacement measurement apparatus can permit to display, before, during or after such treatments, images of measured mechanical property distributions such as of shear modulus using the display unit 10 in order to control the treatments, and also permit to display using imaging such as static, dynamic or temporal change (difference or subtraction) imaging, etc. or values or temporal changes in values (graph) of an arbitrary position etc. with respect to the measurement results obtained by the respective conduct forms of the present invention such as a displacement vector distribution, displacement vector component distributions, strain tensor component distributions, gradient distributions of strain tensor components, a stress tensor distribution, a pressure distribution, a mechanical source distribution, an instantaneous phase change distribution, a shear wave propagation (propagation speed, propagation direction, vibration displacement, vibration velocity, vibration acceleration, vibration amplitude, vibration frequency, vibration directions, phase etc.) etc. Thus, the present invention permits, for the high intensity ultrasound treatment and the force radiation, the high accuracy measurement of the beam direction, the direction to a focus, the focus position, the crossing position of beams, the sound pressure shape distribution (1D, 2D or 3D distribution), the beam shape etc. and if required, with a high spatial resolution. Then, the control of the temperature change or the treatment effectiveness, or deformations or wave propagations etc. permits the high accuracy treatment (minimum-invasive treatment) or the high accuracy shear modulus imaging. The echo imaging or the tissue displacement measurement performed on the high intensity ultrasound treatment or the force radiation can be permitted to be performed. Moreover, tissue mechanical or thermal properties can also be permitted to be estimated from such measurements. The specific evaluation about beams by the present invention is useful for the evaluation, the design and the optimization of the proper beamforming parameters and transducer parameters. The apparatus can be permitted to be equipped with plural functions properly. As mentioned above, the transducer, the high intensity ultrasound applicator, the pressure applicator, the vibrator (for generating a wave or a deformation, a motion etc.), the compressor can be permitted to be realized by one device. When the sensor elements or the applicator elements are realized such that plural functions can be achieved using the same elements, generally proper driving signals should be provided to the elements according to the respective purposes. In the present invention, such driving signals can be permitted to be used. In addition, in the present invention, the properly obtained same driving signals can also be permitted to be provided to the elements instead as mentioned above. The elements for the respective purposes can also be permitted to be installed into one sensor or applicator properly. Also the elements for the respective purposes can be permitted to be installed into the respective sensors or applicators, and then in such a case, the plural sensors or applicators can also be permitted to be used simultaneously. Also the plural sensors or applicators for the same purposes can be permitted to be used simultaneously. When using such plural sensors or applicators, they can also be permitted to be installed into plural apparatuses. According to the applications or selection of functions, automatically the processing for generating the driving signals or other processing can be set, and the apparatus works properly.

The present invention can be applied to a treatment apparatus and/or a diagnosis apparatus using an arbitrary wave such as other mechanical waves, electromagnetic waves, thermal waves etc. in addition to ultrasound echo signals, shear waves etc. Instead of an echo wave, a transmission wave can also be permitted to be used.

The imaging and displacement measurement apparatus can permit to simultaneously use a function of ultrasound imaging, i.e., real-time imaging and measurement of spatially varying of a bulk modulus and density, and then the measurement results obtained using the present invention can be displayed with superposition on such ultrasound data or images; the measurement results to be used for the superposition, the static, dynamic or temporal change (difference or subtraction) image, etc. of a displacement vector distribution, displacement vector component distributions, strain tensor component distributions, gradient distributions of strain tensor components, a stress tensor distribution, a pressure distribution, a mechanical source distribution, an instantaneous phase change distribution, a shear wave propagation (propagation speed, propagation direction, vibration displacement, vibration velocity, vibration acceleration, vibration amplitude, vibration frequency, vibration directions, phase etc.) etc. Regarding the displacement vector distribution or the shear wave propagation, the measurement results can be permitted to be displayed in a vector line map. When performing the temperature measurements mentioned above, thermal property distributions can be permitted to be calculated and then, the planning of treatment can be permitted to be performed. When the measurements of a displacement (vector) or a temperature is performed on the basis of the nuclear magnetic resonance signals, the measurement results obtained can be permitted to be displayed with superposition on the nuclear magnetic resonance image or other medical images. This can also be applied to cases using other diagnosis or treatment apparatuses.

For other treatments such as an interstitial radiotherapy (radiotherapy, high intensity ultrasound radiation, laser radiation, electromagnetic rf-wave or microwave radiation etc.), similarly the imaging and displacement measurement apparatus, and treatment apparatus can be used for the monitoring of the treatment effectiveness (including a temperature change), the control of the treatment and performing the planning of the treatment. Also for the use of anti-cancer drug, similarly the imaging and displacement measurement apparatus, and treatment apparatus can be used for the monitoring of the treatment effectiveness (including a temperature change), the control of the treatment and performing the planning of the treatment.

On the monitoring of effectiveness of these treatments, when these exists no mechanical sources or such mechanical sources are generated, the imaging and displacement measurement apparatus can be used for detecting the tissue degeneration, the tissue expansion or shrink, the change in a temperature etc. through the measurement of a displacement vector and a strain tensor. Also for the electromagnetic or thermal treatments, if there exist no mechanical sources, similarly the present invention can be used.

The imaging and displacement measurement apparatus can also be used as non-destructive examination for living things, objects, substances, materials (also during generating or growing process) etc. through the measurement or monitoring of mechanical quantities such as a displacement vector distribution, strain tensor distribution etc. and mechanical properties such as a shear modulus distribution. The measurement of complex tissue motion such as of a heart etc. and various blood flows such as in the lateral direction parallel to the body surface and complex flows in a heart etc. can also be permitted to be measured. The measurements of mechanical properties and thermal properties etc. can be permitted to be performed to develop materials such as contrast media for the blood flow imaging and the thermal treatment. Thus, the applications are various. Well known contrast media can also be dealt with, and then the increase in a measurement accuracy of peripheral blood flow can be expected.

The invention claimed is:

1. A displacement measurement apparatus comprising:
an ultrasound transducer having at least one vibrator configured to transmit ultrasounds according to at least one driving signal and receive ultrasound echoes to output at least one received signal;
a driving/output control unit configured to generate the at least one driving signal and process the at least one received signal;
a measurement control unit configured to control respective units to set for a measurement object, one of (i) a three-dimensional orthogonal coordinate system having three axes in a depth direction, a lateral direction orthogonal to the depth direction, and an elevational direction orthogonal to the depth direction and the lateral direction, and (ii) a two-dimensional orthogonal coordinate system having two axes in a depth direction and a lateral direction orthogonal to the depth direction, and generate one of three-dimensional ultrasound echo data frames and two-dimensional ultrasound echo data frames on said one of the coordinate systems through scanning the object in at least one of the lateral and elevational directions with an ultrasound steered beam having one steering angle;
a data processing unit configured to obtain, with respect to said one of the three-dimensional ultrasound echo data frames and the two-dimensional ultrasound echo data frames generated at plural different temporal phases, both a beam direction and a frequency in said beam direction based on one of (i) an azimuth angle $\phi=\tan^{-1}(fy/fx)$, a polar angle $\theta=\cos^{-1}[fz/(fx^2+fy^2+fz^2)^{1/2}]$, and a frequency $(fx^2+fy^2+fz^2)^{1/2}$ in a case where instantaneous frequencies in respective axes calculated at each position of interest within a region of interest from at least one multidimensional analytic signal or first spectral moments in respective axes calculated from spectra corresponding to ultrasound echo data within a local region including said position of interest are expressed by a three-dimensional frequency vector (fx, fy, fz), and in a case where first spectral moments in respective axes calculated from global spectra corresponding to ultrasound echo data within the region of interest are expressed by a three-dimensional frequency vector (fx, fy, fz), and (ii) an azimuth angle $\phi=\tan^{-1}(fy/fx)$ and a frequency $(fx^2+fy^2)^{1/2}$ in a case where the instantaneous frequencies or the first spectral moments are expressed by a two-dimensional frequency vector (fx, fy), and configured to calculate a displacement component in said beam direction at each position of interest generated between the plural different temporal phases.

2. The displacement measurement apparatus according to claim 1, wherein said measurement control unit is configured to perform mechanical or electrical steering and beamforming, and detect, when performing mechanical steering, a mechanical steering angle, and configured to set said orthogonal coordinate system at or after performing beamforming.

3. The displacement measurement apparatus according to claim 1, wherein said data processing unit is configured to calculate a displacement component in said beam direction by dividing a change in an instantaneous phase, generated between the plural different temporal phases, by the frequency in said beam direction.

4. The displacement measurement apparatus according to claim 1, wherein said data processing unit is configured to rotate ultrasound echo data, which includes ultrasound echo data from the position of interest, based on said beam direction, and to calculate a displacement component in said beam direction on a new orthogonal coordinate system in which said beam direction is a frontal direction with respect to a physical aperture of said ultrasound transducer.

5. The displacement measurement apparatus according to claim 1, wherein said data processing unit is configured to globally rotate ultrasound echo data within the region of interest based on said beam direction, and to calculate a displacement component in said beam direction on a new orthogonal coordinate system in which said beam direction is a frontal direction with respect to a physical aperture of said ultrasound transducer.

6. The displacement measurement apparatus according to claim 1, wherein said measurement control unit is configured to generate an ultrasound steered beam the steering angle of which is set at zero degrees.

7. The displacement measurement apparatus according to claim 1, wherein said data processing unit is configured to divide, based on said beam direction, multidimensional spectra corresponding to ultrasound echo data including ultrasound echo data from the position of interest, and to calculate a displacement component in said beam direction from a displacement vector calculated by solving simultaneous equations comprising Doppler equations derived from one of multidimensional analytic signals and echo data frames respectively obtained from the divided multidimensional spectra.

8. The displacement measurement apparatus according to claim 7, wherein said data processing unit is configured to solve said simultaneous equations for displacement vector components via one of weighted least squared solution, weighted regularized solution, and weighted mean solution, where weight is statistically determined by using at least one of a confidence of calculated frequencies and instantaneous phase change.

9. The displacement measurement apparatus according to claim 1, wherein said data processing unit is configured to further calculate, at each position of interest, a displacement in a direction of displacement by using said beam direction, the displacement in said beam direction, and the direction of displacement.

10. The displacement measurement apparatus according to claim 9, wherein said data processing unit is configured to use the direction of displacement estimated by using at least one of ultrasound images and other medical images.

11. The displacement measurement apparatus according to claim 1, wherein:
said measurement control unit is configured to generate, at the plural different temporal phases, said one of three-dimensional ultrasound echo data frames and two-dimensional ultrasound echo data frames through scanning the measurement object in at least one of the lateral and elevational directions with ultrasound steered beams having same plural steering angles; and
said data processing unit is configured to obtain both plural beam directions and frequencies in said plural beam directions with respect to the ultrasound echo data frames generated at the plural different temporal phases and the respective ultrasound steered beams having the same steering angles, and to calculate, at each position of interest, a displacement vector by synthesizing displacement components in said plural beam directions.

12. The displacement measurement apparatus according to claim 1, wherein said measurement control unit is configured to manually or automatically select, with respect to beamforming to be performed, one type of beamforming in a combination with a displacement measurement method depending on decision of the measurement object, from among three types of beamforming respectively using (i) an ultrasound beam in a frontal direction with respect to a physical aperture of said ultrasound transducer, (ii) an ultrasound steered beam having one steering angle, (iii) an ultrasound steered beam having a variable steering angle, and (iv) ultrasound steered beams in plural directions generated based on use of said ultrasound steered beam having one steering angle and said ultrasound steered beam having a variable steering angle.

13. The displacement measurement apparatus according to claim 11, wherein said measurement control unit is configured to generate, at the respective temporal phases, said one of three-dimensional ultrasound echo data frames and two-dimensional ultrasound echo data frames through simultaneously or non-simultaneously scanning the measurement object with ultrasound steered beams having said at least one set of same plural beamforming parameters.

14. The displacement measurement apparatus according to claim 12, wherein said measurement control unit is configured to perform, when selecting a type of beamforming using one of (i), (ii), and (iii), modulation in at least one of the lateral and elevational directions orthogonal to said beam direction by disregarding with respect to single quadrant or octant spectra, lateral or elevational low frequency spectra, or laterally or elevationally partial spectra in a neighborhood of said steered beam direction after the beamforming is completed by said data processing unit, and increase, when selecting a type of beamforming using (iv), at least one of a lateral frequency and an elevational frequency in a direction orthogonal to a central direction with respect to plural quadrant or octant spectra by disregarding with respect to the plural quadrant or octant spectra, laterally or elevationally partial spectra with sides of said central direction after the beamforming is completed by said data processing unit.

15. The displacement measurement apparatus according to claim 1, wherein said data processing unit is configured to exchange cosine and sine modulations for each other with respect to at least one of the lateral and elevational modulations by inverting in a frequency domain signs of spectra existing in either one of two quadrants or two octants symmetric with respect to a frequency axis corresponding to the depth direction after the beamforming is completed by said data processing unit.

16. The displacement measurement apparatus according to claim 1, wherein said data processing unit is configured to use harmonic signals of ultrasound echo signals.

17. The displacement measurement apparatus according to claim 1, wherein said data processing unit is configured to use ultrasound echo signals from contrast media.

18. The displacement measurement apparatus according to claim 1, wherein said data processing unit is configured to calculate at least one of strain tensor components or a strain, strain rate tensor components or a strain rate, acceleration vector components or an acceleration, velocity vector components or a velocity, distributions thereof, and temporal series thereof by implementing one of a spatial differential filter and a temporal differential filter to at least one of measured displacement vector components or a displacement, distributions thereof, and temporal series thereof.

19. The displacement measurement apparatus according to claim 1, further comprising:
a display unit configured to display measurement results outputted from said data processing unit based on at least one of calculated displacement vector components or a displacement, strain tensor components or a strain, strain rate tensor components or a strain rate, principle strains or principle strain rates, acceleration vector components or an acceleration, velocity vector components or a velocity, an ultrasound propagation direction, an instantaneous frequency, a change in an instantaneous phase, a shear wave propagation speed, a shear wave propagation direction, a shear wave vibration displacement, a shear wave vibration velocity, a shear wave vibration acceleration, a shear wave vibration amplitude, a shear wave vibration direction, a shear wave vibration frequency, a shear wave phase, distributions thereof, temporal series thereof, an ultrasound echo data frame, signals obtained by detecting superposition of ultrasound echo data frames, signals obtained by superposing detected echo data frames, and data superposed of different images thereof.

20. The displacement measurement apparatus according to claim 19, wherein said display unit is configured to display at least one of an ultrasound echo data frame, signals obtained by detecting superposition of ultrasound echo data frames, and signals obtained by superposing detected echo data frames in one of a negative mode and a usual positive mode.

21. The displacement measurement apparatus according to claim 1, further comprising a detector configured to detect at least one of a nuclear magnetic resonance signal, an electromagnetic wave, light, and a thermal wave.

22. The displacement measurement apparatus according to claim 1, wherein said orthogonal coordinate system includes one of (i) a Cartesian coordinate system, (ii) a curvilinear coordinate system including a polar coordinate system, and (iii) one of an orthogonal coordinate system suitable for an aperture shape and an orthogonal coordinate system unrelated to an aperture shape.

23. The displacement measurement apparatus according to claim 1, wherein:
said measurement control unit is configured to generate, at the plural different temporal phases, said one of three-dimensional ultrasound echo data frames and two-dimensional ultrasound echo data frames through scanning the measurement object in at least one of the lateral and elevational directions with ultrasound steered beams having at least one set of same plural beamforming parameters consisting of same plural steering angles, same plural ultrasound frequencies, same plural lateral frequencies, same plural pulse shapes, same plural wavenumbers, same plural bandwidths, same plural aperture widths, same plural F-numbers, same plural delays, same plural apodizations, same plural focus positions, same plural ultrasound intensities, same plural acoustic pressure distributions, and same plural beam shapes; and
said data processing unit is configured to superpose, at the plural different temporal phases, the ultrasound echo data frames, to obtain both said beam direction and a frequency in said beam direction with respect to the superposed ultrasound echo data frames, and to calculate a displacement component in said beam direction at each position of interest generated between the plural different temporal phases.

24. The displacement measurement apparatus according to claim 23, wherein said measurement control unit is configured to generate, at the respective temporal phases, said one of three-dimensional ultrasound echo data frames and two-dimensional ultrasound echo data frames through simultaneously or non-simultaneously scanning the measurement object with ultrasound steered beams having said at least one set of same plural beamforming parameters.

25. The displacement measurement apparatus according to claim 23, wherein said data processing unit is configured to solve said simultaneous equations for displacement vector components via one of weighted least squared solution, weighted regularized solution, and weighted mean solution, where weight is statistically determined by using at least one of a confidence of calculated frequencies and instantaneous phase change.

26. The displacement measurement apparatus according to claim 1, wherein said ultrasound transducer is configured to transmit laterally or elevationally wide waves.

27. The displacement measurement apparatus according to claim 1, wherein said data processing unit is configured to specifically examine at least one of the generated ultrasound echo data frames and the ultrasound steered beams in terms of, in addition to said beam direction and a frequency in the beam direction, at least one of a directivity of a transducer or a vibrator, a reflection position, a reflection direction, a refraction position, a refraction direction, a boundary, a scattering, an attenuation, a reflectivity, a refractive index or a propagation speed of acoustic wave or other waves, point spread function, spectra, one of properties of said other waves consisting of a propagation direction, a frequency in the propagation direction, a focus position, an intensity, a bandwidth, a spatial resolution, and a wave shape, and one of beamforming parameters consisting of a steering angle, a bandwidth, a spatial resolution, a focus position, a crossing position of beams or waves, an ultrasound intensity, an ultrasound energy, an acoustic pressure distribution, and a beam shape.

28. The displacement measurement apparatus according to claim 27, wherein said data processing unit is configured to further optimize one of beamforming parameters consisting of said beam direction, a frequency in said beam direction, a bandwidth, a focus position, a crossing position of beams or waves, an ultrasound intensity, an ultrasound energy, an acoustic pressure distribution and a beam shape, one of radiation force parameters, one of high intensity focus ultrasound parameters, one of transducer parameters consisting of an element shape, an element width, an element pitch, and an element materials, one of superposition or division parameters of spectra consisting of a position, a direction, a shape and a weight or a window or a filter, and a weight or a window or a filter for changing spectra, in terms of at least one of an echo SNR (signal-to-noise ratio), an echo contrast, an image quality, a measurement accuracy of displacement, temperature or shear wave, a generated deformation, a generated motion, a mechanical source, an intensity of radiation force, a heat source, an efficiency of heat generation, a temperature rising, a degeneration, said beamforming parameters, said radiation force parameters, and said high intensity focus ultrasound parameters, a wave propagation direction, a frequency in said beam direction and other wave properties, by using an estimated point spread function or spectra.

29. The displacement measurement apparatus according to claim 27, further comprising:
a display unit configured to display examined results of said data processing unit as images.

30. The displacement measurement apparatus according to claim 1, further comprising:
at least one of a high intensity focus ultrasound applicator and a radiation force applicator;
wherein said ultrasound transducer is also used to detect echo signals with respect to driving said at least one of the high intensity focus ultrasound applicator and the radiation force applicator.

31. The displacement measurement apparatus according to claim 30, wherein said data processing unit is configured to weight, superpose, or divide spectra of echo data frames obtained at the plural different temporal phases for respective purposes of echo imaging, displacement measurement, generation of a mechanical source, and thermal treatment.

32. The displacement measurement apparatus according to claim 1, wherein:
said ultrasound transducer is also used as at least one of a high intensity focus ultrasound applicator and a radiation force applicator; and
said ultrasound transducer is also used to detect echo signals with respect to driving said at least one of the high intensity focus ultrasound applicator and the radiation force applicator.

33. The displacement measurement apparatus according to claim 32, wherein said data processing unit is configured to weight, superpose, or divide spectra of echo data frames obtained at the plural different temporal phases for respective purposes of echo imaging, displacement measurement, and thermal treatment.

34. The displacement measurement apparatus according to claim 1, further comprising:
plural different mechanical sources or radiated forces configured to generate plural different deformation fields or shear wave propagation fields.

35. The displacement measurement apparatus according to claim 34, wherein said data processing unit is configured to superpose independently generated deformation fields or shear wave propagation fields, or echo data frames generated with respect to respectively generated deformation fields or shear wave propagation fields, in order to control a new deformation field or a new shear wave propagation field.

36. The displacement measurement apparatus according to claim 34, wherein said data processing unit is configured to calculate an anisotropy shear modulus by using generated deformation fields or shear wave propagation fields.

37. The displacement measurement apparatus according to claim 1, further comprising:
plural different mechanical sources or radiated forces configured to generate a deformation field or a shear wave propagation field.

38. The displacement measurement apparatus according to claim 1, wherein said data processing unit is configured to further calculate at least one of a shear wave propagation speed, a shear wave propagation direction, a shear wave vibration displacement, a shear wave vibration velocity, a shear wave vibration acceleration, a shear wave vibration amplitude, a shear wave vibration direction, a shear wave vibration frequency, a shear wave phase, distributions thereof, and temporal series thereof from at least one of measured shear wave displacement vector components or a shear wave displacement, distributions thereof, and temporal series thereof.

39. The displacement measurement apparatus according to claim 38, wherein said data processing unit is configured to use an instantaneous frequency in a shear wave propagation direction and a shear wave propagation direction at respective points of interest or globally calculated shear wave frequency and shear wave propagation direction.

40. The displacement measurement apparatus according to claim 38, wherein said data processing unit is configured to use at least one of a displacement measurement method and a displacement vector measurement method.

* * * * *